United States Patent
Koether et al.

(10) Patent No.: US 6,525,001 B1
(45) Date of Patent: Feb. 25, 2003

(54) SUBSTITUTED PYRIMIDINE AND PYRIDINE HERBICIDES

(75) Inventors: Gerard Michael Koether, Bear, DE (US); Thomas Paul Selby, Wilmington, DE (US); Thomas Martin Stevenson, Newark, DE (US)

(73) Assignee: Mid-American Commercialization Corporation, Manhatten, KS (US)

( * ) Notice: Subject to any disclaimer, the term of this patent is extended or adjusted under 35 U.S.C. 154(b) by 0 days.

(21) Appl. No.: 09/555,746

(22) PCT Filed: Oct. 20, 1998

(86) PCT No.: PCT/US98/22088

§ 371 (c)(1),
(2), (4) Date: Jun. 2, 2000

(87) PCT Pub. No.: WO99/28301

PCT Pub. Date: Jun. 10, 1999

Related U.S. Application Data

(60) Provisional application No. 60/068,432, filed on Dec. 22, 1997, and provisional application No. 60/067,418, filed on Dec. 3, 1997.

(51) Int. Cl.$^7$ .................... C07D 239/26; C07D 401/04; C07D 403/04; A01N 43/54
(52) U.S. Cl. ................... 504/239; 544/242; 544/333; 544/334; 544/335
(58) Field of Search ................ 544/242, 333, 544/334, 335; 504/239

(56) References Cited

U.S. PATENT DOCUMENTS 5,075,316 A * 12/1991 Hubele ................ 514/275

FOREIGN PATENT DOCUMENTS

| EP | 0459662 | 12/1991 | ......... C07D/401/04 |
|---|---|---|---|
| EP | 0723960 | 7/1996 | ......... C07D/213/00 |
| JP | 3-169802 | * 7/1991 | |
| JP | 5-213878 | 8/1993 | ......... C07D/213/53 |

* cited by examiner

Primary Examiner—Deepak Rao
(74) Attorney, Agent, or Firm—Hovey Williams LLP

(57) ABSTRACT

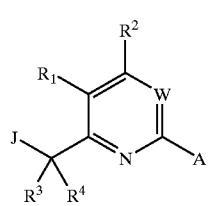

(I)

-continued

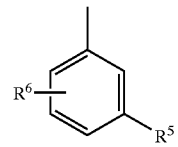 (J-1)

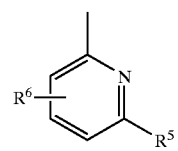

(J-2)

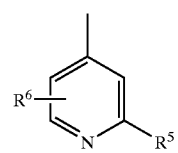

(J-3)

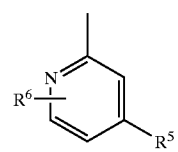

(J-4)

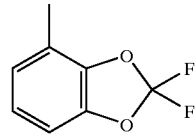

(J-5)

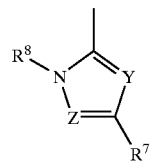

(J-6)

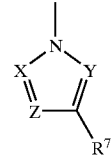

(J-7)

Compounds of formula (I), and their N-oxides and agriculturally suitable salts, are disclosed which are useful for controlling undesired vegetation, wherein J is (J-1), (J-2), (J-3), (J-4), (J-5), (J-6) or (J-7); and J, W, X, Y, Z, A, $R^1$–$R^8$ are as defined in the disclosure. Also disclosed are compositions containing the compounds of formula (I) and a method for controlling undesired vegetation which involves contacting the vegetation or its environment with an effective amount of a compound of formula (I).

9 Claims, No Drawings

SUBSTITUTED PYRIMIDINE AND PYRIDINE HERBICIDES

CROSS REFERENCE TO RELATED APPLICATIONS

This application was filed under 35 U.S.C. 371 from International Application PCT/US98/22088 filed Oct. 20, 1998 which claims priority benefit from Provisional Application No. 60/067,418 filed Dec. 3, 1997 and Provisional Application No. 60/068,432 filed Dec. 22, 1997.

BACKGROUND OF THE INVENTION

This invention relates to certain pyrimidines and pyridines, their N-oxides, agriculturally suitable salts, compositions thereof, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

EP 723,960 discloses herbicidal substituted pyrimidines and pyridines of Formula i:

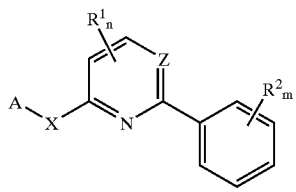

i wherein, inter alia,

A is an optionally substituted aryl or 5- or 6-membered nitrogen containing heteroaromatic group;

X is oxygen or sulfur;

Z is nitrogen or CH;

$R^1$ and $R^2$ are independently hydrogen, halogen, alkyl, haloalkyl, nitro or cyano;

n is 0, 1 or 2; and m is 0 to 5.

The pyrimidines and pyridines of the present invention are not disclosed in this reference.

SUMMARY OF THE INVENTION

This invention is directed to compounds of Formula I including all geometric and stereoisomers, N-oxides, and agriculturally suitable salts thereof, as well as agricultural compositions containing them and a method of their use for controlling undesirable vegetation:

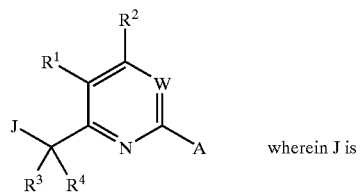

I wherein J is

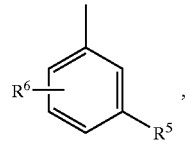

J-1

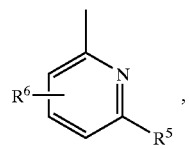

J-2

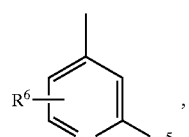

J-3

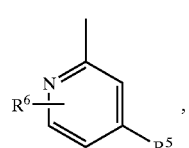

J-4

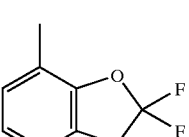

J-5

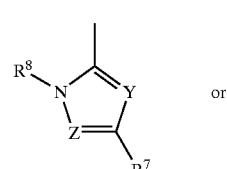

J-6

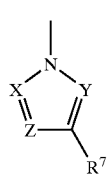

J-7 or

A is

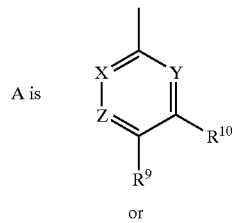

A-1 or

-continued

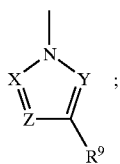

A-2

W is N or CR$^{11}$;

X, Y and Z are independently N or CR$^{12}$;

R$^1$ and R$^2$ are independently H, halogen, cyano, C$_1$–C$_4$ alkoxy, C$_1$–C$_4$ haloalkoxy, C$_2$–C$_4$ alkoxyalkyl, C$_1$–C$_4$ alkyl, C$_1$–C$_4$ haloalkyl, C$_2$–C$_4$ alkoxyalkyl, C$_2$–C$_4$ alkenyl, C$_2$–C$_4$ alkynyl, C$_3$–C$_4$ alkenyloxy, C$_3$–C$_4$ alkynyloxy, S(O)$_n$R$^{13}$, C$_2$–C$_4$ alkylthioalkyl, C$_2$–C$_4$ alkylsulfonylalkyl, C$_1$–C$_4$ alkylamino or C$_2$–C$_4$ dialkylamino;

R$^3$ is H, F, Cl, Br, cyano, C$_1$–C$_4$ alkyl, C$_1$–C$_4$ haloalkyl or CO$_2$R$^{14}$;

R$^4$ is H, F, C$_1$–C$_4$ alkyl, OH or OR$^{14}$;

R$^3$ and R$^4$ can be taken together with the carbon to which they are attached to form C(=O) or C(=NOR$^{14}$);

R$^5$ is halogen, cyano, SF$_5$, C$_1$–C$_4$ alkyl, C$_1$–C$_4$ haloalkyl, C$_1$–C$_4$ alkoxy, C$_{1-4}$ haloalkoxy or S(O)$_n$R$^{13}$;

R$^6$ and R$^{10}$ are independently H, halogen, cyano, C$_1$–C$_4$ alkyl, C$_1$–C$_4$ haloalkyl, C$_1$–C$_4$ alkoxy, C$_1$–C$_4$ haloalkoxy or S(O)$_n$R$^{13}$;

R$^7$ is halogen, cyano, SF$_5$, C$_1$–C$_4$ alkyl, C$_1$–C$_4$ haloalkyl, C$_1$–C$_4$ alkoxy, C$_1$–C$_4$ haloalkoxy or S(O)$_n$R$^{13}$;

R$^8$ is C$_1$–C$_4$ alkyl or C$_1$–C$_4$ haloalkyl;

R$^9$ is H, halogen, cyano, SF$_5$, C$_1$–C$_4$ alkoxy, C$_1$–C$_4$ haloalkoxy, C$_1$–C$_4$ alkyl, C$_1$–C$_4$ haloalkyl, C$_2$–C$_4$ alkenyl, C$_2$–C$_4$ alkynyl, C$_3$–C$_4$ alkenyloxy, C$_3$–C$_4$ alkynyloxy or S(O)$_n$R$^{13}$;

R$^{11}$ is H, halogen, cyano, C$_1$–C$_4$ alkyl, C$_1$–C$_4$ haloalkyl, C$_1$–C$_4$ alkoxy, C$_1$–C$_4$ haloalkoxy or S(O)$_n$R$^{13}$;

R$^{12}$ is H, halogen, cyano, C$_1$–C$_4$ alkyl, C$_1$–C$_4$ haloalkyl, C$_1$–C$_4$ alkoxy, C$_1$–C$_4$ haloalkoxy or S(O)$_n$R$^{13}$;

each R$^{13}$ is independently C$_1$–C$_4$ alkyl or C$_1$–C$_4$ haloalkyl;

each R$^{14}$ is independently C$_1$–C$_4$ alkyl; and each n is independently 0, 1 or 2.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1-2 alkyl" indicates that one or two of the available positions for that substituent may be alkyl which are independently selected. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkenyloxy" includes straight-chain or branched alkenyloxy moieties. Examples of "alkenyloxy" include H$_2$C=CHCH$_2$O, (CH$_3$)$_2$C=CHCH$_2$O, (CH$_3$)CH=CHCH$_2$O, (CH$_3$)CH=C(CH$_3$)CH$_2$O and CH$_2$=CHCH$_2$CH$_2$O. "Alkynyloxy" includes straight-chain or branched alkynyloxy moieties. Examples of "alkynyloxy" include HC≡CCH$_2$O, CH$_3$C≡CCH$_2$O and CH$_3$C≡CCH$_2$CH$_2$O. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include CH$_3$SCH$_2$, CH$_3$SCH$_2$CH$_2$, CH$_3$CH$_2$SCH$_2$, CH$_3$CH$_2$CH$_2$CH$_2$SCH$_2$ and CH$_3$CH$_2$SCH$_2$CH$_2$. "Alkylsulfinyl" includes both enantiomers of an alkylsulfinyl group. Examples of "alkylsulfinyl" include CH$_3$S(O), CH$_3$CH$_2$S(O), CH$_3$CH$_2$CH$_2$S(O), (CH$_3$)$_2$CHS(O) and the different butylsulfinyl, pentylsulfinyl and hexylsulfinyl isomers. Examples of "alkylsulfonyl" include CH$_3$S(O)$_2$, CH$_3$CH$_2$S(O)$_2$, CH$_3$CH$_2$CH$_2$S(O)$_2$, (CH$_3$)$_2$CHS(O)$_2$ and the different butylsulfonyl, pentylsulfonyl and hexylsulfonyl isomers. "Alkylamino", "dialkylamino", "alkenylthio", "alkenylsulfinyl", "alkenylsulfonyl", "alkynylthio", "allynylsulfinyl", "alkynylsulfonyl", and the like, are defined analogously to the above examples. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748–750, S. V. Ley, Ed., Pergamon Press; M. Tisler and B. Stanovnik in *Comprehensive Heterocyclic Chemistry*, vol. 3, pp 18–20, A. J. Boulton and A. McKillop, Eds., Pergamon Press; M. R. Grimmett and B. R. T. Keene in *Advances in Heterocyclic Chemistry*, vol. 43, pp 149–161, A. R. Katritzky, Ed., Academic Press; M. Tisler and B. Stanovnik in *Advances in Heterocyclic Chemistry*, vol. 9, pp 285–291, A. R. Katritzky and A. J. Boulton, Eds., Academic Press; and G. W. H. Cheeseman and E. S. G. Werstiuk in *Advances in Heterocyclic Chemistry*, vol. 22, pp 390–392, A. R. Katritzky and A. J. Boulton, Eds., Academic Press.

The term "halogen", either alone or in compound words such as "haloalkyl", includes fluorine, chlorine, bromine or iodine. The term "1-2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include F$_3$C, ClCH$_2$, CF$_3$CH$_2$ and CF$_3$CCl$_2$. Examples of "haloalkoxy" include CF$_3$O, CCl$_3$CH$_2$O, HCF$_2$CH$_2$CH$_2$O and CF$_3$CH$_2$O.

The total number of carbon atoms in a substituent group is indicated by the "C$_i$–C$_j$" prefix where i and j are numbers from 1 to 4. For example, C$_1$–C$_3$ alkylsulfonyl designates methylsulfonyl through propylsulfonyl; C$_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a group contains a substituent which can be hydrogen, for example $R^9$, then, when this substituent is taken as hydrogen, it is recognized that this is equivalent to said group being unsubstituted.

The compounds of this invention thus include compounds of Formula I, geometric and stereoisomers thereof, N-oxides thereof, and agriculturally suitable salts thereof. The compound of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Preferred compounds of the invention for reasons of better activity and/or ease of synthesis are:

Preferred 1. Compounds of Formula I above, geometric or stereoisomers thereof, N-oxides thereof and agriculturally-suitable salts thereof, wherein $R^1$ and $R^2$ are independently H, $C_1$–$C_4$ alkyl or $C_1$–$C_4$ alkoxy;

$R^5$ and $R^7$ are independently halogen, $C_1$–$C_4$ haloalkyl, $C_1$–$C_4$ haloalkoxy or $S(O)_nR^{13}$;

$R^6$ is H or F;

$R^8$ is $C_1$–$C_4$ alkyl;

$R^9$ is halogen, cyano, $C_1$–$C_4$ alkoxy, $C_1$–$C_4$ haloalkoxy, $C_1$–$C_4$ alkyl, $C_1$–$C_4$ haloalkyl or $S(O)_nR^{13}$;

$R^{10}$ is H, halogen, cyano or $C_1$–$C_4$ haloalkyl;

$R^{11}$ is H, halogen, cyano or $C_1$–$C_4$ haloalkyl;

$R^{12}$ is H, halogen, cyano or $C_1$–$C_4$ haloalkyl; and n is 0.

Preferred 2. Compounds of Preferred 1 wherein

W is N;

$R^5$ and $R^7$ are independently $C_1$–$C_4$ haloalkyl or $C_1$–$C_4$ haloalkoxy; and $R^9$ is halogen, $C_1$–$C_4$ haloalkoxy, $C_1$–$C_4$ haloalkyl or $S(O)_nR^{13}$.

Preferred 3. Compounds of Preferred 2 wherein $R^1$ is $C_1$–$C_4$ alkyl or $C_1$–$C_4$ alkoxy;

$R^2$ is H;

$R^3$ and $R^4$ are independently H, F or methyl;

$R^5$ and $R^7$ are independently $C_1$–$C_2$ haloalkyl or $C_1$–$C_2$ haloalkoxy; and $R^9$ is $C_1$–$C_2$ haloalkoxy, $C_1$–$C_2$ haloalkyl or $S(O)_nR^{13}$.

Preferred 4. Compounds of Preferred 3 wherein

J is J-1, J-5 or J-7.

Preferred 5. Compounds of Preferred 2 wherein $R^3$ and $R^4$ can be taken together with the carbon to which they are attached to form $C(=O)$.

Preferred 6. Compounds of Preferred 5 wherein $R^1$ is $C_1$–$C_4$ alkyl or $C_1$–$C_4$ alkoxy;

$R^2$ is H;

$R^5$ and $R^7$ are independently $C_1$–$C_2$ haloalkyl or $C_1$–$C_2$ haloalkoxy; and $R^9$ is $C_1$–$C_2$ haloalkoxy, $C_1$–$C_2$ haloalkyl or $S(O)_nR^{13}$.

Preferred 7. Compounds of Preferred 5 wherein

J is J-1 or J-5.

Most preferred is the compound of Formula I selected from the group consisting of:

(a) 5-ethyl-4-[[3-(trifluoromethoxy)phenyl]methyl]-2-[3-(trifluoromethyl)-1H-pyrazol-1-yl]pyrimidine;

(b) 5-ethyl-4-[[3-(trifluoromethyl)phenyl]methyl]-2-[3-(trifluoromethyl)-1H-pyrazol-1-yl]pyrimidine;

(c) 5-methyl-2-[4-(trifluoromethyl)phenyl]-4-[[3-(trifluoromethyl)phenyl]methyl]pyrimidine;

(d) 5-methyl-4-[[3-(trifluoromethoxy)phenyl]methyl]-2-[4-(trifluoromethyl)phenyl]pyrimidine;

(e) 5-methyl-4-[[3-(trifluoromethoxy)phenyl]methyl]-2-[3-(trifluoromethyl)-1H-pyrazol-1-yl]pyrimidine;

(f) [5-methyl-2-[4-(trifluoromethyl)phenyl]-4-pyrimidinyl][3-(trifluoromethyl)phenyl]methanone;

(g) [5-methyl-2-[3-(trifluoromethyl)-1H-pyrazol-1-yl]-4-pyrimidinyl][3-(trifluoromethyl)phenyl]methanone; and (h) 5-methyl-4-[[3-(trifluoromethyl)phenyl]methyl]-2-[3-(trifluoromethyl)-1H-pyrazol-1-yl]pyrimidine.

This invention also relates to herbicidal compositions comprising herbicidally effective amounts of the compounds of the invention and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of the invention (e.g., as a composition described herein). The preferred methods of use are those involving the above preferred compounds.

DETAILS OF THE INVENTION

The compounds of Formula I can be prepared by one or more of the following methods and variations as described in Schemes 1–12. The definitions of J, A, W, X, Y, Z, $R^1$, $R^2$, $R^3$, $R^4$, $R^9$, $R^{10}$, and $R^{14}$ in the compounds of Formulae 1–16 below are as defined above in the Summary of the Invention. Compounds of Formulae Ia–Ic are various subsets of the compounds of Formula I, and all substituents for Formulae Ia–Ic are as defined above for Formula I.

Scheme 1 illustrates the preparation of compounds of Formula Ia (Formula I wherein A is A-1). Substituted heterocycles of Formula 1 (where $L^1$ is halogen) can be coupled with metalated aryls or heteroaryls of Formula 2 (where Met is $Sn(alkyl)_3$, $B(OH)_2$ or $Zn(L^1)_2$) in the presence of a palladium(0) catalyst such as tetrakis (triphenylphosphine)palladium(O) or in the presence of a palladium(II) catalyst such as dichlorobis(triphenylphosphine)palladium(II) to provide compounds of Formula Ia. Palladium(II) catalysts are generally used with a suitable base such as aqueous sodium bicarbonate or sodium carbonate. Suitable solvents for this coupling include N,N-dimethylformamide, dimethoxyethane, acetonitrile or tetrahydrofuran. Reaction temperatures range from 20° C. to 130° C.

Scheme 1

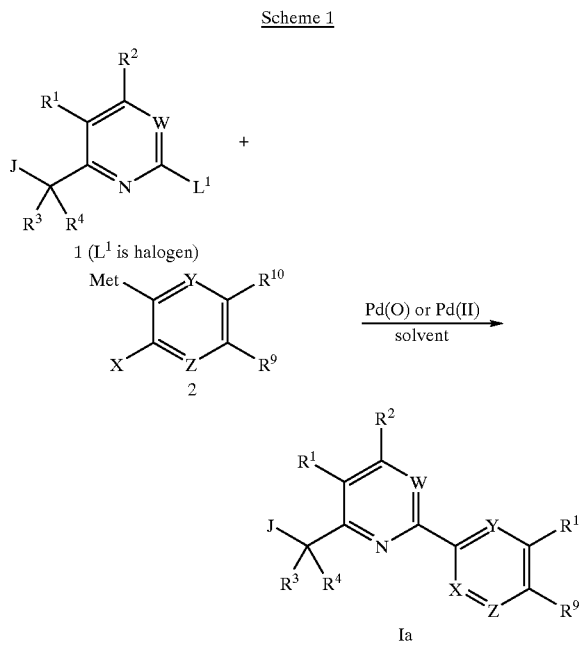

Scheme 2 illustrates the preparation of compounds of Formula Ib (Formula I wherein A is A-2). Substituted heterocycles of Formula 1 are allowed to react with substituted azoles of Formula 3 in the presence of a suitable base such as an alkali carbonate, alkali hydroxide, or alkali hydride in a solvent such as N,N-dimethylformamide, acetonitrile or tetrahydrofuran at temperatures ranging from 0° C. to 130° C. to provide compounds of Formula Ib.

Scheme 2

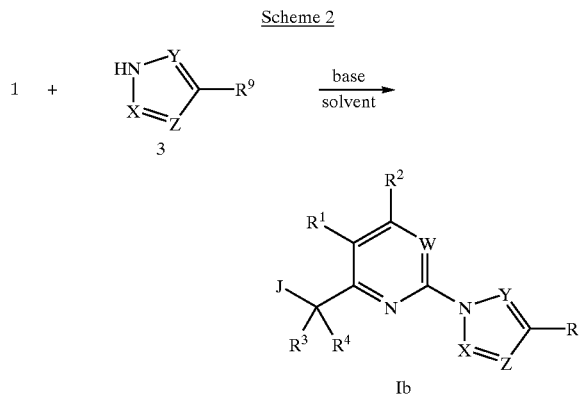

Scheme 3 illustrates a method for preparing compounds of Formula Ic wherein J is an azole heterocycle of Formula J-7 and A is A-1 or A-2. Compounds of Formula 4 are allowed to react with an azole heterocycle of Formula 3 in a protic or aprotic solvent at temperatures ranging from 0° C. to 100° C. in the presence of a suitable base such an alkali carbonate, alkali hydroxide, or alkali hydride to provide compounds of Formula Ic. Particularly suitable are potassium carbonate as base and acetonitrile or N,N-dimethylformamide as solvent at a reaction temperature range of 20° C. to 80° C.

Scheme 3

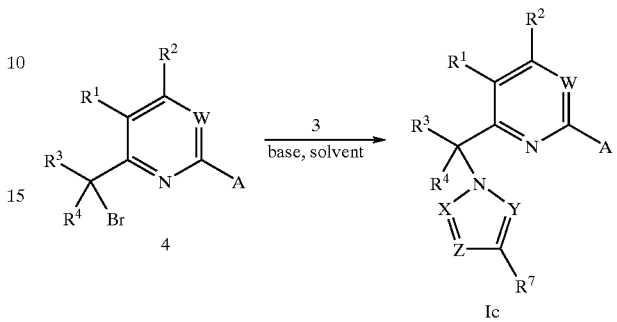

Substituted pyrimidine intermediates of Formula 1 (wherein J is J-1 to J-6) can be prepared by the method shown in Scheme 4. By the synthetic protocol of Menta, E. and Oliva, A. *J. Heterocyclic Chem.* (1997), 34, p 27, a dihalopyrimidine of Formula 5 (where $L^1$ and $L^2$ are halogen) is coupled with a substituted alkyl zinc reagent of Formula 6 (where $L^3$ is halogen) in the presence of a palladium(O) catalyst such as tetrakis(triphenylphosphine)palladium(O) or in the presence of a palladium(II) catalyst such as dichloro-bis(triphenylphosphine)palladium(II). Palladium(II) catalysts are generally used with a suitable base such as sodium bicarbonate or sodium carbonate. Suitable solvents for this coupling include N,N-dimethylformamide, dimethoxyethane, acetonitrile or tetrahydrofuran. Reaction temperatures range from 0° C. to 130° C.

Scheme 4

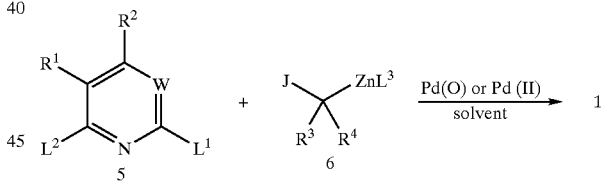

Metalated aryls and heteroaryls of Formula 2 can be obtained commercially or can be prepared by methods known in the art: Sandosham, J. and Undheim, K. *Tetrahedron* (1994), 50, pp 275–284; Undheim, K. and Benneche, T. *Acta Chemica Scandinavica* (1993), 47, pp 102–121; *Advances in Heterocyclic Chemistry*; Katritzky, A. R., Ed.; Academic Press: New York, 1995; volume 62, pp 305–418.

Azoles of Formula 3 can be obtained commercially or can be prepared by methods known in the art Elguero, J. et al., *Organic Preparations and Procedures Int.* (1995), 27, pp 33–74; *Comprehensive Heterocyclic Chemistry*; Potts, K., Ed.; Pergamon Press: New York, 1984; volume 5, chapters 4.04–4.13; *Heterocyclic Compounds*; Elderfield, R., Ed.; John Wiley: New York, 1957; volume 5, chapters 2 and 4; Baldwin, J. et al. *J. Med. Chem.*, (1975), 18, pp 895–900; Evans, J. J. et al. U.S. Pat. No. 4,038,405.

Dihaloheterocycles of Formula 5 can be obtained commercially or can be readily prepared by known methods in the art; for example, see *Advances in Heterocyclic Chemis-* try; Katritzky, A. R., Ed.; Academic Press: New York, 1993; volume 58, pp 301–305; *Heterocyclic Compounds;* Elderfield, R. C., Ed.; John Wiley: New York, 1957; volume 6, chapter 7, pp 265–270.

Zinc reagents of Formula 6 can be made by the method shown in Scheme 5. A substituted alkyl halide of Formula 7 (where $L^3$ is halogen) is allowed to react with activated zinc (see Jubert, C. and Knochel, P. *J. Org. Chem.* (1992), 57, p 5425; Knochel, P. and Singer, R. D. *Chem. Rev.* (1993), 93, p 2117) in a suitable solvent such as N,N-dimethylformamide, dimethoxyethane, acetonitrile or tetrahydrofuran. Reaction temperatures range from 0° C. to 130° C.

Scheme 5

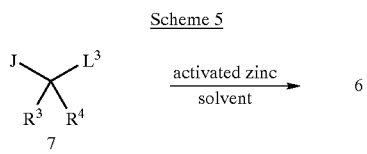

As shown in Scheme 6, heterocyclic benzylic bromides of Formula 4 can be made by bromination of heterocycles of Formula 8 with bromine in an acidic solvent such as acetic acid at temperatures ranging from 20° C. to 100° C. (see, for example, Strekowski et al. *J. Org. Chem.* (1992), 56, p 5610).

Scheme 6

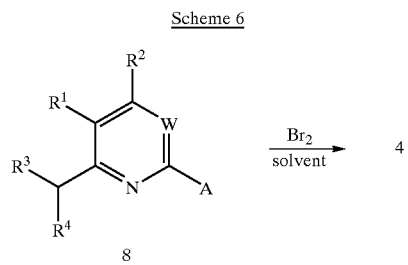

Heterocycles of Formula 8 can be made from precursor heterocycles of Formula 9 as shown in Scheme 7. The addition of lithium or Grignard reagents of formula $R^3R^4CHLi$ or $R^3R^4CHMgL^1$ to heterocycles of Formula 9 is carried out in ethereal solvents such as ether or tetrahydrofuran at temperatures ranging from −70° C. to 30° C. The reaction mixture is worked up by the addition of water and an oxidizing agent. A particularly suitable oxidizing agent is dichlorodicyanoquinone (DDQ). See Strekowski et al. *J. Org. Chem.* (1992), 56, p 5610 for examples of this synthetic method.

Scheme 7

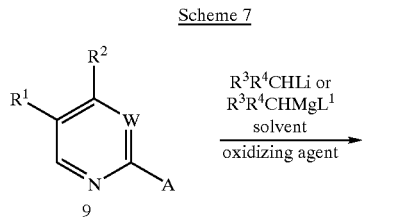

Heterocycles of Formula 9 can be prepared according to methods taught by Strekowski et al. *J. Org. Chem.* (1992), 56, p 5610; Bredereck et. al., *Chem. Ber.* (1960), 93, p 1208; Burdeska et al. *Helv. Chim. Acta* (1981), 64, p 113; Undheim, K. and Benneche, T. *Advances in Heterocyclic Chemistry;* Katritzky, A. R., Ed.; Academic Press: New York, 1995, volume 62, pp 305–418; and *Comprehensive Heterocyclic Chemistry;* Boulton, A. J., and McKillop, A., Eds.; Pergamon Press: New York, 1984; volume 3, chapter 2.13. Lithium and Grignard reagents of formulae $R^3R^4CHLi$ or $R^3R^4CHMgL^1$ are commercially available or can be prepared by methods well known in the art.

Compounds of Formula 1 (wherein $R^3$ and $R^4$ are taken together as C(═O)) can be prepared by the condensation of pyrimidines and pyridines of Formula 10 with aldehydes of Formula 11 in the presence of an imidazolium catalyst of Formula 12 as shown in Scheme 8. This reaction is carried out in the presence of a strong base such as an alkali hydride, preferably sodium hydride, in solvents such as dichloromethane, dioxane, tetrahydrofuran, benzene, toluene or other aprotic solvent. The reaction may be carried out at temperatures between 0 and 120° C. A wide variety of azolium salts are known to catalyze this transformation; see, for example, Miyashita *Heterocycles,* (1996), 43, 509–512 and references cited therein. A preferred catalyst is 1,3-dimethylimidazolium iodide.

Scheme 8

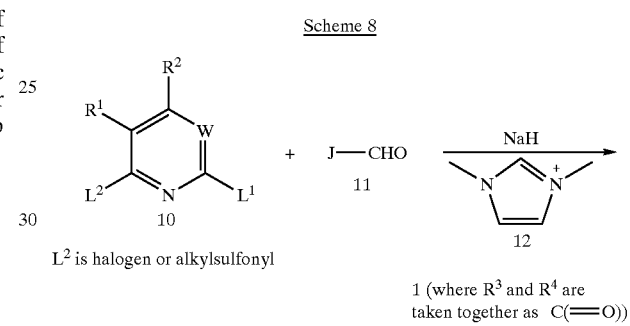

$L^2$ is halogen or alkylsulfonyl 1 (where $R^3$ and $R^4$ are taken together as C(═O))

Compounds of Formula I (wherein $R^3$ and $R^4$ are taken together as C(═$NOR^{14}$)) can be formed directly from compounds of Formula I (wherein $R^3$ and $R^4$ are taken together as C(═O)) by the action of hydroxylamine or capped hydroxylamine salts of Formula 13 as shown in Scheme 9. Many hydroxylamines are commercially available as acid salts and are freed by the action of a base in the presence of the ketone of Formula I. Suitable bases include alkali carbonates, acetates, and hydroxides. These reactions are best carried out in protic solvents, such as lower alcohols, at temperatures between 0 and 120° C. Especially preferred conditions use sodium carbonate or sodium acetate as base in ethanol at 70 to 80° C.

Scheme 9

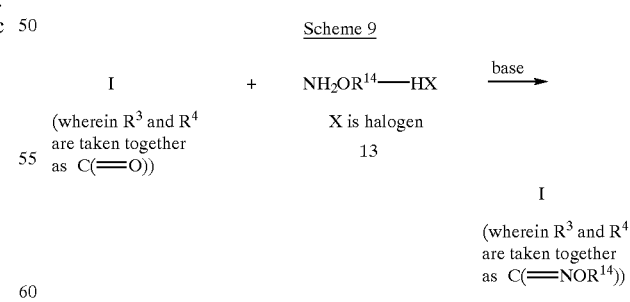

Compounds of Formula I (wherein $R^3$ is OH and $R^4$ is H) can be made by the reduction of ketones of Formula I (wherein $R^3$ and $R^4$ are taken together as C(═O)) as shown in Scheme 10. A wide variety of reduction conditions can be utilized, but for reasons of ease of use and selectivity, alkali borohydrides are preferred reductants. The reduction can be carried out at 0 to 100° C. in a variety of solvents which are inert to the action of borohydrides. Especially preferred conditions are the use of sodium borohydride in ethanol at 0 to 25° C.

Scheme 10

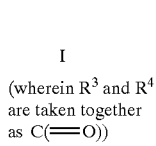
(wherein $R^3$ and $R^4$ are taken together as C(=O))

+ $Z^+(BH_4)^-$
Z is an alkali metal

⟶

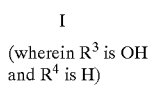
I
(wherein $R^3$ is OH and $R^4$ is H)

As shown in Scheme 11, compounds of Formula 1 wherein J is J-7 can also be made via the bromination of compounds of Formula 14 with molecular bromine in an acidic solvent such as acetic acid at temperatures ranging from 20 to 100° C. in the same way as previously described in Scheme 6. The brominated products of Formula 15 can be displaced by heterocycles of Formula 3 in the presence of a base such as potassium carbonate as previously described for Scheme 2. Compounds of Formula 14 are known in the literature or are commercially available. See Benneche (*Acta Chemica Scandanavia*, 1997, 51, 302) for preparation of these compounds from compounds of Formula 5.

Scheme 11

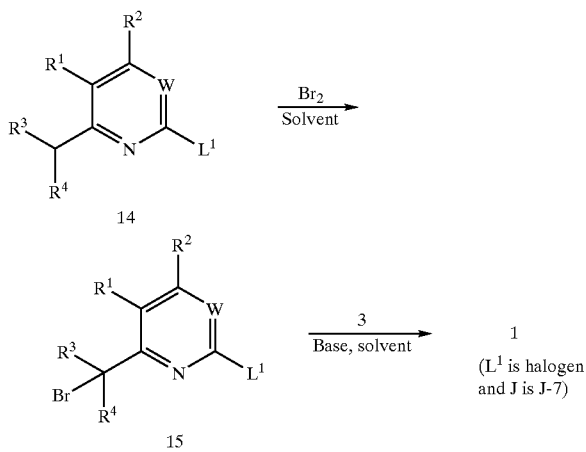

Compounds of Formula 1 in which $R^3$ is cyano can be made as shown in Scheme 12. The reaction of acetonitrile derivatives of formula 16 with compounds of Formula 5 in the presence of a base gives compounds of formula 1 with a cyano group. The reaction can be carried out in a variety of solvents such as dimethylformamide, tetrahydrofuran, or other solvents inert to strong bases. A wide variety of bases which can deprotonate substituted acetonitriles can be used. Sodium hydride and potassium t-butoxide are preferred due to their ease of use and availability. The reaction can be carried out at temperatures ranging from 0 to 100° C. Compounds of formula 16 are well known in the literature and many are commercially available Scheme 12

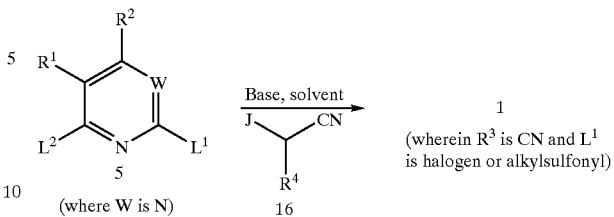

Compounds of Formula I substituted with the group $S(O)_nR^{13}$ wherein n is 1 or 2 can be prepared from compounds of Formula I substituted with said $S(O)_nR^{13}$ group wherein n is 0 by treatment with an oxidizing reagent such as m-chloroperoxybenzoic acid or Oxone® (potassium peroxymonosulfate). This type of oxidation reaction is well known in the art; for example, see March, J. *Advanced Organic Chemistry*; John Wiley: New York, 1992; $4^{th}$ edition, pp 1201–1203.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I. One skilled in the art will also recognize that it may be necessary to perform a combination of the steps illustrated in the above schemes in an order other than that implied by the particular sequence presented to prepare the compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; s=singlet, d=doublet, t=triplet, q=quartet, m=multiplet, dd=doublet of doublets, dt=doublet of triplets, br s=broad singlet.

EXAMPLE 1

Step A: Preparation of 2-chloro-5-methyl-4-[[3-(trifluoromethyl)phenyl]methyl]pyrimidine To a suspension of zinc dust (2.5 g, 38 mmol) stirred in 25 mL of tetrahydrofuran were added 2 drops of 1,2- dibromoethane and the mixture was heated to reflux. The suspension was then cooled and 2 drops of trimethylsilyl chloride were added followed by portionwise addition of 3-(trifluoromethyl)benzyl bromide (6.0 g, 25 mmol) with heating. When the reaction temperature reached 55° C., a strong exotherm occurred and the reaction mixture was allowed to heat at reflux. The cooled reaction solution was decanted into a solution of 2,4dichloro-5-methylpyrimidine (3.3 g, 20 mmol) and dichlorobis(triphenylphosphine) palladium(II) (0.44 g, 0.63 mmol) stirring in 15 mL of tetrahydrofuran. Upon heating, the reaction mixture exothermed strongly again at 55° C. and was then heated to reflux. The reaction mixture was allowed to cool and partitioned between diethyl ether and water. The organic layer was separated, washed with 1 N aqueous hydrochloric acid and brine, dried over magnesium chloride and concentrated under reduced pressure to give a crude oil. Purification by flash chromatography on silica gel (15 to 25% ethyl acetate in hexane) yielded 2.4 g of the title compound of Step A as an oil. $^1$H NMR (CDCl$_3$): $\delta$8.35 (s, 1H), 7.60–7.35 (m, 4H), 4.15 (s, 2H), 2.25 (s, 3H).

Step B: Preparation of 5-methyl-2-[4-(trifluoromethyl)phenyl]-4-[[3-(trifluoromethyl) phenyl]methyl]pyrimidine A stirred mixture of 4-(trifluoromethyl)benzene boronic acid (430 mg, 2.3 mmol), the title compound of Step A (500 mg, 1.7 mmol), dichlorobis(triphenylphosphine)palladium (II) (120 mg, 0.17 mmol) and sodium carbonate (550 mg, 5.2 mmol) in a mixture of 6 mL of water and 2 mL of tetrahydrofuran was heated at reflux for 1.5 h. The reaction mixture was then partitioned between diethyl ether and water. The organic layer was separated, washed with brine, dried over magnesium sulfate and concentrated under reduced pressure. Flash chromatography on silica gel (20 to 25% ethyl acetate in hexane) followed by trituration with 10% diethyl ether in hexane afforded 350 mg of the title compound of Step B, a compound of this invention, as a yellow-tinted solid melting at 112–113° C. $^1$H NMR (CDCl$_3$): $\delta$8.55 (m, 3H), 7.70 (d, 2H), 7.60 (s, 1H), 7.55–7.40 (m, 3H), 4.25 (s, 2H), 2.30 (s, 3H).

EXAMPLE 2

Step A: Preparation of 5-methyl-4-[[3-(trifluoromethyl)phenyl]methyl]-2-[3-(trifluoromethyl)-1H-pyrazol-1-yl]pyrimidine A stirred mixture of 3-(trifluoromethyl)pyrazole (390 mg, 2.9 mmol), the title compound of Step A in Example 1 (750 mg, 2.6 mmol), and powdered potassium carbonate (1.1 g, 7.9 mmol) in 10 mL of N,N-dimethylformamide was heated at 60° C. for 3 h followed by heating at 80° C. for 1 h. The reaction mixture was then partitioned between diethyl ether and water. The organic layer was separated, washed with brine, dried over magnesium sulfate and concentrated under reduced pressure. Column chromatography on silica gel (5% diethyl ether in 1-chlorobutane) afforded 210 mg of the title compound of Step A as an oil which solidified to a white solid melting at 90–92° C. $^1$H NMR (CDCl$_3$): $\delta$8.55 (t,2H), 7.55–7.50 (m, 2H), 7.45–7.40 (m, 2H), 6.72 (d, 1H), 4.26 (s, 2H), 2.32 (s, 3H).

EXAMPLE 3

Step A: Preparation of 5-methyl-2-(4-trifluoromethylphenyl)pyrimidine

A sample of 4-trifluoromethylbenzamidine hydrochloride dihydrate (Maybridge, 15.2 g, 58 mmol) was dissolved in 100 mL of methanol and 3-ethoxy-2-methylacrolein (Janssen, 7.8 g, 64 mmol) was added. Sodium methoxide (25% solution in methanol, 14.7 mL) was added and the mixture was heated at 50° C. for 3 h. The cooled reaction mixture was then dded to 500 ml of ice water and stirred for 30 minutes. The white solid was filtered, air dried, dissolved in 300 mL of dichloromethane and dried over magnesium sulfate. The solvent was removed under reduced pressure to yield, after trituration with hexanes, 12.5 g of the product as a white solid melting at 143–146° C. $^1$H NMR (CDCl$_3$): $\delta$2.37 (s, 3H), 7.73 (d, 2H), 8.53 (d, 2H), 8.66 (s, 2H).

Step B: Preparation of 4,5-dimethyl-2-(4-trifluoromethylphenyl)pyrimidine

The title compound of Step A (9.0 g, 38 mmol) was dissolved in 50 mL of tetrahydrofuran and treated with methyl lithium (1.4 M in ether, 34 mL, 47 mmol) at a temperature of −70° C. The reaction mixture exothermed to −35° C. The mixture was stirred at −30° C. for 1.5 h and then treated with 1 mL of water and dichlorodicyanoquinone (9.44 g, 42 mmol). The mixture was stirred at 25° C. for 30 minutes and then partitioned twice between 100 mL of water and 100 mL of dichloromethane. The combined organics were washed with brine and dried over magnesium sulfate. The residue after evaporation was subjected to silica gel chromatography using hexanes/ethyl acetate (95:5) as eluent to give 9.02 g of the title compound of Step B as a white solid melting at 128–131° C. $^1$H NMR (CDCl$_3$): $\delta$2.31 (s, 3H), 2.56 (s, 3H), 7.71 (d, 2H), 8.49 (d, 2H), 8.53 (s, 1H).

Step C: Preparation of 4-bromomethyl-5-methyl-2-(4-trifluoromethylphenyl)pyrimidine The title compound of Step B (2.0 g, 8 mmol) was dissolved in 10 mL of acetic acid and treated with bromine (0.4 mL, 8 mmol). The mixture was heated at 80° C. until the orange color was discharged (1 h). The mixture was evaporated under reduced pressure, diluted with 50 mL of ether and washed twice with 50 mL of sodium bicarbonate and then 50 mL of brine. The organic layer was dried over magnesium sulfate and concentrated under reduced pressure to yield 2.54 g of the title compound of Step C as a tan solid which was used immediately in the next step without further purification. $^1$H NMR (CDCl$_3$): $\delta$2.44 (s, 3H), 4.54 (s, 2H), 7.74 (d, 2H), 8.56 (d, 2H), 8.62 (s, 1H).

Step D: Preparation of 5-methyl-2-(4-trifluoromethylphenyl)-4-[3-(trifluoromethyl)-1H-pyrazol-1-yl]methylpyrimidine The title compound of Step C (0.7 g, 2 mmol), 3-trifluoromethylpyrazole (0.27 g, 2 mmol) and potassium carbonate (0.83 g, 6 mmol) were suspended in 10 mL of acetonitrile and heated to reflux for 1 h. The salts were filtered and the acetonitrile was removed under reduced pressure. The residue was purified by chromatography on silica gel eluting with hexanes/ethyl acetate (85:15) to afford 0.52 g of the title compound of Step D, a compound of this invention, as a white solid melting at 112–114° C. $^1$H NMR (CDCl$_3$): $\delta$2.39 (s, 3H), 5.53 (s, 2H), 6.62 (d, 1H), 7.6–7.8 (m, 3H), 8.44 (d, 2H), 8.6 (s, 1H).

EXAMPLE 4

Step A: Preparation of (2-chloro-5-methyl-4-pyrimidinyl)[3-(trifluoromethyl)phenyl]methanone 2,4-Dichloro-5-methylpyrimidine (3.6 g, 18.4 mmol) was dissolved in dichloromethane (50 mL) and treated sequentially with 3-trifluoromethylbenzaldehyde (3.3 g, 18.4 mmol), and 1,3-dimethylimidazolium iodide (1.37 g, 6.2 mmol). Sodium hydride (0.74 g, 18.4 mmol) was added and an exotherm was noted. After being heated at reflux for 3 h, the reaction was quenched with water and the layers were separated. The dried (magnesium sulfate) organic layer was purified by chromatography on silica gel using hexanes/ethyl acetate 85:15 as eluent. The title compound of Step A (1.8 g) was isolated as a white solid melting at 113–116° C. $^1$H NMR (CDCl$_3$/200 MHz) 2.39 (s, 3H), 7.66 (m, 1H), 7.90 (d, 1H), 8.07 (s,1H), 8.69 (s, 1H).

Step B: Preparation of [5-methyl-2-[3-(trifluoromethyl)-1H-pyrazol-1-yl]-4-pyrimidinyl][3-(trifluoromethyl)phenyl]methanone The title compound of Step A (0.6 g, 2 mmol), 3-trifluoromethylpyrazole (0.25 g), and potassium carbonate (0.8 g, 6 mmol) were suspended in acetonitrile (15 mL) and heated at reflux for 3 h. The cooled reaction mixture was filtered and the cake washed with acetonitrile. After evaporation of the solvent under reduced pressure, the residue was subjected to silica gel chromatography using hexanes/ethyl acetate (85:15) to give 0.12 g of the title compound of Step B, a compound of the invention, as a white solid. $^1$H NMR (CDCl$_3$/200 MHz) 2.45 (s, 3H), 6.75 (d, 1H), 7.67 (d, 1H), 7.92 (d, 1H), 8.10 (s, 1H), 8.27 (s, 1H), 8.54 (d, 1H), 8.9 (s, 1H).

EXAMPLE 5

Step A: Preparation of [5-methyl-2-[4-(trifluoromethyl)phenyl]-4-pyrimidinyl][3-(trifluoromethyl)phenyl]methanone The title compound of Example 1, Step A (0.6 g, 2 mmol), 4-trifluoromethyl-benzeneboronic acid (1.1 g, 6 mmol), and bis(triphenylphosphine)palladium dichloride were dissolved in dimethoxyethane (15 mL) and aqueous sodium carbonate (2 M, 4 mmol). The resulting mixture was heated at 80° C. for 3 h. The mixture was diluted with dichloromethane (50 mL) and water (50 mL). The dichloromethane layer was dried over magnesium sulfate, concentrated under reduced pressure, and the residue was subjected to silica gel chromatography using hexaneslethyl acetate (85:15). The title compound of Step A, a compound of the invention, was isolated as a white solid (0.56 g) melting at 159–161° C. $^1$H NMR (CDCl$_3$/200 MHz) 2.47 (s, 3H), 7.62–7.78 (m, 3H), 7.94 (d, 1H), 8.17 (d, 1H), 8.34 (s, 1H), 8.5 (d, 2H), 8.9 (s, 1H).

By the procedures described herein together with methods known in the art, the following compounds of Tables 1 to 34 can be prepared.

TABLE 1

| $R^1$ | $R^4$ | $R^5$ | $R^9$ | $R^1$ | $R^4$ | $R^5$ | $R^9$ |
|---|---|---|---|---|---|---|---|
| $R^3$ is H; X, Y and Z are CH ||||||||
| H | H | CF$_3$ | CF$_3$ | H | H | OCF$_3$ | CF$_3$ |
| H | H | CF$_3$ | OCF$_3$ | H | H | OCF$_3$ | OCF$_3$ |
| H | H | CF$_3$ | SCF$_3$ | H | H | OCF$_3$ | SCF$_3$ |
| H | H | CF$_3$ | OCHF$_2$ | H | H | OCF$_3$ | OCHF$_2$ |
| H | H | CF$_3$ | SCHF$_2$ | H | H | OCF$_3$ | SCHF$_2$ |
| H | H | CF$_3$ | C$_2$F$_5$ | H | H | OCF$_3$ | C$_2$F$_5$ |
| H | H | CF$_3$ | Cl | H | H | OCF$_3$ | Cl |
| H | H | CF$_3$ | SCH$_2$CH$_3$ | H | H | OCF$_3$ | SCH$_2$CH$_3$ |
| H | H | OCHF$_2$ | CF$_3$ | H | H | SCF$_3$ | CF$_3$ |
| H | H | OCHF$_2$ | OCF$_3$ | H | H | SCF$_3$ | OCF$_3$ |
| H | H | OCHF$_2$ | SCF$_3$ | H | H | SCF$_3$ | SCF$_3$ |
| H | H | OCHF$_2$ | OCHF$_2$ | H | H | SCF$_3$ | OCHF$_2$ |
| H | H | OCHF$_2$ | SCHF$_2$ | H | H | SCF$_3$ | SCHF$_2$ |
| H | H | OCHF$_2$ | C$_2$F$_5$ | H | H | SCF$_3$ | C$_2$F$_5$ |
| H | H | OCHF$_2$ | Cl | H | H | SCF$_3$ | Cl |
| H | H | OCHF$_2$ | SCH$_2$CH$_3$ | H | H | SCF$_3$ | SCH$_2$CH$_3$ |
| H | H | SCHF$_2$ | CF$_3$ | H | H | Cl | CF$_3$ |
| H | H | SCHF$_2$ | OCF$_3$ | H | H | Cl | OCF$_3$ |
| H | H | SCHF$_2$ | SCF$_3$ | H | H | Cl | SCF$_3$ |
| H | H | SCHF$_2$ | OCHF$_2$ | H | H | Cl | OCHF$_2$ |
| H | H | SCHF$_2$ | SCHF$_2$ | H | H | Cl | SCHF$_2$ |
| H | H | SCHF$_2$ | C$_2$F$_5$ | H | H | Cl | C$_2$F$_5$ |
| H | H | SCHF$_2$ | Cl | H | H | Cl | Cl |
| H | H | SCHF$_2$ | SCH$_2$CH$_3$ | H | H | Cl | SCH$_2$CH$_3$ |
| H | CH$_3$ | CF$_3$ | CF$_3$ | H | CH$_3$ | OCF$_3$ | CF$_3$ |
| H | CH$_3$ | CF$_3$ | OCF$_3$ | H | CH$_3$ | OCF$_3$ | OCF$_3$ |
| H | CH$_3$ | CF$_3$ | SCF$_3$ | H | CH$_3$ | OCF$_3$ | SCF$_3$ |
| H | CH$_3$ | CF$_3$ | OCHF$_2$ | H | CH$_3$ | OCF$_3$ | OCHF$_2$ |
| H | CH$_3$ | CF$_3$ | SCHF$_2$ | H | CH$_3$ | OCF$_3$ | SCHF$_2$ |
| H | CH$_3$ | CF$_3$ | C$_2$F$_5$ | H | CH$_3$ | OCF$_3$ | C$_2$F$_5$ |
| H | CH$_3$ | CF$_3$ | Cl | H | CH$_3$ | OCF$_3$ | Cl |
| H | CH$_3$ | CF$_3$ | SCH$_2$CH$_3$ | H | CH$_3$ | OCF$_3$ | SCH$_2$CH$_3$ |
| H | CH$_3$ | OCHF$_2$ | CF$_3$ | H | CH$_3$ | SCF$_3$ | CF$_3$ |

TABLE 1-continued

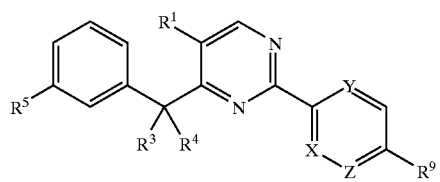

| R$^1$ | R$^4$ | R$^5$ | R$^9$ | R$^1$ | R$^4$ | R$^5$ | R$^9$ |
|---|---|---|---|---|---|---|---|
| H | CH$_3$ | OCHF$_2$ | OCF$_3$ | H | CH$_3$ | SCF$_3$ | OCF$_3$ |
| H | CH$_3$ | OCHF$_2$ | SCF$_3$ | H | CH$_3$ | SCF$_3$ | SCF$_3$ |
| H | CH$_3$ | OCHF$_2$ | OCHF$_2$ | H | CH$_3$ | SCF$_3$ | OCHF$_2$ |
| H | CH$_3$ | OCHF$_2$ | SCHF$_2$ | H | CH$_3$ | SCF$_3$ | SCHF$_2$ |
| H | CH$_3$ | OCHF$_2$ | C$_2$F$_5$ | H | CH$_3$ | SCF$_3$ | C$_2$F$_5$ |
| H | CH$_3$ | OCHF$_2$ | Cl | H | CH$_3$ | SCF$_3$ | Cl |
| H | CH$_3$ | OCHF$_2$ | SCH$_2$CH$_3$ | H | CH$_3$ | SCF$_3$ | SCH$_2$CH$_3$ |
| H | CH$_3$ | SCHF$_2$ | CF$_3$ | H | CH$_3$ | Cl | CF$_3$ |
| H | CH$_3$ | SCHF$_2$ | OCF$_3$ | H | CH$_3$ | Cl | OCF$_3$ |
| H | CH$_3$ | SCHF$_2$ | SCF$_3$ | H | CH$_3$ | Cl | SCF$_3$ |
| H | CH$_3$ | SCHF$_2$ | OCHF$_2$ | H | CH$_3$ | Cl | OCHF$_2$ |
| H | CH$_3$ | SCHF$_2$ | SCHF$_2$ | H | CH$_3$ | Cl | SCHF$_2$ |
| H | CH$_3$ | SCHF$_2$ | C$_2$F$_5$ | H | CH$_3$ | Cl | C$_2$F$_5$ |
| H | CH$_3$ | SCHF$_2$ | Cl | H | CH$_3$ | Cl | Cl |
| H | CH$_3$ | SCHF$_2$ | SCH$_2$CH$_3$ | H | CH$_3$ | Cl | SCH$_2$CH$_3$ |
| H | F | CF$_3$ | CF$_3$ | H | F | OCF$_3$ | CF$_3$ |
| H | F | CF$_3$ | OCF$_3$ | H | F | OCF$_3$ | OCF$_3$ |
| H | F | CF$_3$ | SCF$_3$ | H | F | OCF$_3$ | SCF$_3$ |
| H | F | CF$_3$ | OCHF$_2$ | H | F | OCF$_3$ | OCHF$_2$ |
| H | F | CF$_3$ | SCHF$_2$ | H | F | OCF$_3$ | SCHF$_2$ |
| H | F | CF$_3$ | C$_2$F$_5$ | H | F | OCF$_3$ | C$_2$F$_5$ |
| H | F | CF$_3$ | Cl | H | F | OCF$_3$ | Cl |
| H | F | CF$_3$ | SCH$_2$CH$_3$ | H | F | OCF$_3$ | SCH$_2$CH$_3$ |
| H | F | OCHF$_2$ | CF$_3$ | H | F | SCF$_3$ | OCF$_3$ |
| H | F | OCHF$_2$ | OCF$_3$ | H | F | SCF$_3$ | OCF$_3$ |
| H | F | OCHF$_2$ | SCF$_3$ | H | F | SCF$_3$ | SCF$_3$ |
| H | F | OCHF$_2$ | OCHF$_2$ | H | F | SCF$_3$ | OCHF$_2$ |
| H | F | OCHF$_2$ | SCHF$_2$ | H | F | SCF$_3$ | SCHF$_2$ |
| H | F | OCHF$_2$ | C$_2$F$_5$ | H | F | SCF$_3$ | C$_2$F$_5$ |
| H | F | OCHF$_2$ | Cl | H | F | SCF$_3$ | Cl |
| H | F | OCHF$_2$ | SCH$_2$CH$_3$ | H | F | SCF$_3$ | SCH$_2$CH$_3$ |
| H | F | SCHF$_2$ | CF$_3$ | H | F | Cl | CF$_3$ |
| H | F | SCHF$_2$ | OCF$_3$ | H | F | Cl | OCF$_3$ |
| H | F | SCHF$_2$ | SCF$_3$ | H | F | Cl | SCF$_3$ |
| H | F | SCHF$_2$ | OCHF$_2$ | H | F | Cl | OCHF$_2$ |
| H | F | SCHF$_2$ | SCHF$_2$ | H | F | Cl | SCHF$_2$ |
| H | F | SCHF$_2$ | C$_2$F$_5$ | H | F | Cl | C$_2$F$_5$ |
| H | F | SCHF$_2$ | Cl | H | F | Cl | Cl |
| H | F | SCHF$_2$ | SCH$_2$CH$_3$ | H | F | Cl | SCH$_2$CH$_3$ |
| H | Cl | CF$_3$ | CF$_3$ | H | Cl | OCF$_3$ | CF$_3$ |
| H | Cl | CF$_3$ | OCF$_3$ | H | Cl | OCF$_3$ | OCF$_3$ |
| H | Cl | CF$_3$ | SCF$_3$ | H | Cl | OCF$_3$ | SCF$_3$ |
| H | Cl | CF$_3$ | OCHF$_2$ | H | Cl | OCF$_3$ | OCHF$_2$ |
| H | Cl | CF$_3$ | SCHF$_2$ | H | Cl | OCF$_3$ | SCHF$_2$ |
| H | Cl | CF$_3$ | C$_2$F$_5$ | H | Cl | OCF$_3$ | C$_2$F$_5$ |
| H | Cl | CF$_3$ | Cl | H | Cl | OCF$_3$ | Cl |
| H | Cl | CF$_3$ | SCH$_2$CH$_3$ | H | Cl | OCF$_3$ | SCH$_2$CH$_3$ |
| H | Cl | OCHF$_2$ | CF$_3$ | H | Cl | SCF$_3$ | CF$_3$ |
| H | Cl | OCHF$_2$ | OCF$_3$ | H | Cl | SCF$_3$ | OCF$_3$ |
| H | Cl | OCHF$_2$ | SCF$_3$ | H | Cl | SCF$_3$ | SCF$_3$ |
| H | Cl | OCHF$_2$ | OCHF$_2$ | H | Cl | SCF$_3$ | OCHF$_2$ |
| H | Cl | OCHF$_2$ | SCHF$_2$ | H | Cl | SCF$_3$ | SCHF$_2$ |
| H | Cl | OCHF$_2$ | C$_2$F$_5$ | H | Cl | SCF$_3$ | C$_2$F$_5$ |
| H | Cl | OCHF$_2$ | Cl | H | Cl | SCF$_3$ | Cl |
| H | Cl | OCHF$_2$ | SCH$_2$CH$_3$ | H | Cl | SCF$_3$ | SCH$_2$CH$_3$ |
| H | Cl | SCHF$_2$ | CF$_3$ | H | Cl | Cl | CF$_3$ |
| H | Cl | SCHF$_2$ | OCF$_3$ | H | Cl | Cl | OCF$_3$ |
| H | Cl | SCHF$_2$ | SCF$_3$ | H | Cl | Cl | SCF$_3$ |
| H | Cl | SCHF$_2$ | OCHF$_2$ | H | Cl | Cl | OCHF$_2$ |
| H | Cl | SCHF$_2$ | SCHF$_2$ | H | Cl | Cl | SCHF$_2$ |
| H | Cl | SCHF$_2$ | C$_2$F$_5$ | H | Cl | Cl | C$_2$F$_5$ |
| H | Cl | SCHF$_2$ | Cl | H | Cl | Cl | Cl |
| H | Cl | SCHF$_2$ | SCH$_2$CH$_3$ | H | Cl | Cl | SCH$_2$CH$_3$ |
| CH$_3$ | H | CF$_3$ | CF$_3$ | CH$_3$ | H | OCF$_3$ | CF$_3$ |
| CH$_3$ | H | CF$_3$ | OCF$_3$ | CH$_3$ | H | OCF$_3$ | OCF$_3$ |
| CH$_3$ | H | CF$_3$ | SCF$_3$ | CH$_3$ | H | OCF$_3$ | SCF$_3$ |
| CH$_3$ | H | CF$_3$ | OCHF$_2$ | CH$_3$ | H | OCF$_3$ | OCHF$_2$ |

TABLE 1-continued

| R¹ | R⁴ | R⁵ | R⁹ | R¹ | R⁴ | R⁵ | R⁹ |
|---|---|---|---|---|---|---|---|
| $CH_3$ | H | $CF_3$ | $SCHF_2$ | $CH_3$ | H | $OCF_3$ | $SCHF_2$ |
| $CH_3$ | H | $CF_3$ | $C_2F_5$ | $CH_3$ | H | $OCF_3$ | $C_2F_5$ |
| $CH_3$ | H | $CF_3$ | $Cl$ | $CH_3$ | H | $OCF_3$ | $Cl$ |
| $CH_3$ | H | $CF_3$ | $SCH_2CH_3$ | $CH_3$ | H | $OCF_3$ | $SCH_2CH_3$ |
| $CH_3$ | H | $OCHF_2$ | $CF_3$ | $CH_3$ | H | $SCF_3$ | $CF_3$ |
| $CH_3$ | H | $OCHF_2$ | $OCF_3$ | $CH_3$ | H | $SCF_3$ | $OCF_3$ |
| $CH_3$ | H | $OCHF_2$ | $SCF_3$ | $CH_3$ | H | $SCF_3$ | $SCF_3$ |
| $CH_3$ | H | $OCHF_2$ | $OCHF_2$ | $CH_3$ | H | $SCF_3$ | $OCHF_2$ |
| $CH_3$ | H | $OCHF_2$ | $SCHF_2$ | $CH_3$ | H | $SCF_3$ | $SCHF_2$ |
| $CH_3$ | H | $OCHF_2$ | $C_2F_5$ | $CH_3$ | H | $SCF_3$ | $C_2F_5$ |
| $CH_3$ | H | $OCHF_2$ | $Cl$ | $CH_3$ | H | $SCF_3$ | $Cl$ |
| $CH_3$ | H | $OCHF_2$ | $SCH_2CH_3$ | $CH_3$ | H | $SCF_3$ | $SCH_2CH_3$ |
| $CH_3$ | H | $SCHF_2$ | $CF_3$ | $CH_3$ | H | $Cl$ | $CF_3$ |
| $CH_3$ | H | $SCHF_2$ | $OCF_3$ | $CH_3$ | H | $Cl$ | $OCF_3$ |
| $CH_3$ | H | $SCHF_2$ | $SCF_3$ | $CH_3$ | H | $Cl$ | $SCF_3$ |
| $CH_3$ | H | $SCHF_2$ | $OCHF_2$ | $CH_3$ | H | $Cl$ | $OCHF_2$ |
| $CH_3$ | H | $SCHF_2$ | $SCHF_2$ | $CH_3$ | H | $Cl$ | $SCHF_2$ |
| $CH_3$ | H | $SCHF_2$ | $C_2F_5$ | $CH_3$ | H | $Cl$ | $C_2F_5$ |
| $CH_3$ | H | $SCHF_2$ | $Cl$ | $CH_3$ | H | $Cl$ | $Cl$ |
| $CH_3$ | H | $SCHF_2$ | $SCH_2CH_3$ | $CH_3$ | H | $Cl$ | $SCH_2CH_3$ |
| $CH_3$ | $CH_3$ | $CF_3$ | $CF_3$ | $CH_3$ | $CH_3$ | $OCF_3$ | $CF_3$ |
| $CH_3$ | $CH_3$ | $CF_3$ | $OCF_3$ | $CH_3$ | $CH_3$ | $OCF_3$ | $OCF_3$ |
| $CH_3$ | $CH_3$ | $CF_3$ | $SCF_3$ | $CH_3$ | $CH_3$ | $OCF_3$ | $SCF_3$ |
| $CH_3$ | $CH_3$ | $CF_3$ | $OCHF_2$ | $CH_3$ | $CH_3$ | $OCF_3$ | $OCHF_2$ |
| $CH_3$ | $CH_3$ | $CF_3$ | $SCHF_2$ | $CH_3$ | $CH_3$ | $OCF_3$ | $SCHF_2$ |
| $CH_3$ | $CH_3$ | $CF_3$ | $C_2F_5$ | $CH_3$ | $CH_3$ | $OCF_3$ | $C_2F_5$ |
| $CH_3$ | $CH_3$ | $CF_3$ | $Cl$ | $CH_3$ | $CH_3$ | $OCF_3$ | $Cl$ |
| $CH_3$ | $CH_3$ | $CF_3$ | $SCH_2CH_3$ | $CH_3$ | $CH_3$ | $OCF_3$ | $SCH_2CH_3$ |
| $CH_3$ | $CH_3$ | $OCHF_2$ | $CF_3$ | $CH_3$ | $CH_3$ | $SCF_3$ | $CF_3$ |
| $CH_3$ | $CH_3$ | $OCHF_2$ | $OCF_3$ | $CH_3$ | $CH_3$ | $SCF_3$ | $OCF_3$ |
| $CH_3$ | $CH_3$ | $OCHF_2$ | $SCF_3$ | $CH_3$ | $CH_3$ | $SCF_3$ | $SCF_3$ |
| $CH_3$ | $CH_3$ | $OCHF_2$ | $OCHF_2$ | $CH_3$ | $CH_3$ | $SCF_3$ | $OCHF_2$ |
| $CH_3$ | $CH_3$ | $OCHF_2$ | $SCHF_2$ | $CH_3$ | $CH_3$ | $SCF_3$ | $SCHF_2$ |
| $CH_3$ | $CH_3$ | $OCHF_2$ | $C_2F_5$ | $CH_3$ | $CH_3$ | $SCF_3$ | $C_2F_5$ |
| $CH_3$ | $CH_3$ | $OCHF_2$ | $Cl$ | $CH_3$ | $CH_3$ | $SCF_3$ | $Cl$ |
| $CH_3$ | $CH_3$ | $OCHF_2$ | $SCH_2CH_3$ | $CH_3$ | $CH_3$ | $SCF_3$ | $SCH_2CH_3$ |
| $CH_3$ | $CH_3$ | $SCHF_2$ | $CF_3$ | $CH_3$ | $CH_3$ | $Cl$ | $CF_3$ |
| $CH_3$ | $CH_3$ | $SCHF_2$ | $OCF_3$ | $CH_3$ | $CH_3$ | $Cl$ | $OCF_3$ |
| $CH_3$ | $CH_3$ | $SCHF_2$ | $SCF_3$ | $CH_3$ | $CH_3$ | $Cl$ | $SCF_3$ |
| $CH_3$ | $CH_3$ | $SCHF_2$ | $OCHF_2$ | $CH_3$ | $CH_3$ | $Cl$ | $OCHF_2$ |
| $CH_3$ | $CH_3$ | $SCHF_2$ | $SCHF_2$ | $CH_3$ | $CH_3$ | $Cl$ | $SCHF_2$ |
| $CH_3$ | $CH_3$ | $SCHF_2$ | $C_2F_5$ | $CH_3$ | $CH_3$ | $Cl$ | $C_2F_5$ |
| $CH_3$ | $CH_3$ | $SCHF_2$ | $Cl$ | $CH_3$ | $CH_3$ | $Cl$ | $Cl$ |
| $CH_3$ | $CH_3$ | $SCHF_2$ | $SCH_2CH_3$ | $CH_3$ | $CH_3$ | $Cl$ | $SCH_2CH_3$ |
| $CH_3$ | F | $CF_3$ | $CF_3$ | $CH_3$ | F | $OCF_3$ | $CF_3$ |
| $CH_3$ | F | $CF_3$ | $OCF_3$ | $CH_3$ | F | $OCF_3$ | $OCF_3$ |
| $CH_3$ | F | $CF_3$ | $SCF_3$ | $CH_3$ | F | $OCF_3$ | $SCF_3$ |
| $CH_3$ | F | $CF_3$ | $OCHF_2$ | $CH_3$ | F | $OCF_3$ | $OCHF_2$ |
| $CH_3$ | F | $CF_3$ | $SCHF_2$ | $CH_3$ | F | $OCF_3$ | $SCHF_2$ |
| $CH_3$ | F | $CF_3$ | $C_2F_5$ | $CH_3$ | F | $OCF_3$ | $C_2F_5$ |
| $CH_3$ | F | $CF_3$ | $Cl$ | $CH_3$ | F | $OCF_3$ | $Cl$ |
| $CH_3$ | F | $CF_3$ | $SCH_2CH_3$ | $CH_3$ | F | $OCF_3$ | $SCH_2CH_3$ |
| $CH_3$ | F | $OCHF_2$ | $CF_3$ | $CH_3$ | F | $SCF_3$ | $CF_3$ |
| $CH_3$ | F | $OCHF_2$ | $OCF_3$ | $CH_3$ | F | $SCF_3$ | $OCF_3$ |
| $CH_3$ | F | $OCHF_2$ | $SCF_3$ | $CH_3$ | F | $SCF_3$ | $SCF_3$ |
| $CH_3$ | F | $OCHF_2$ | $OCHF_2$ | $CH_3$ | F | $SCF_3$ | $OCHF_2$ |
| $CH_3$ | F | $OCHF_2$ | $SCHF_2$ | $CH_3$ | F | $SCF_3$ | $SCHF_2$ |
| $CH_3$ | F | $OCHF_2$ | $C_2F_5$ | $CH_3$ | F | $SCF_3$ | $C_2F_5$ |
| $CH_3$ | F | $OCHF_2$ | $Cl$ | $CH_3$ | F | $SCF_3$ | $Cl$ |
| $CH_3$ | F | $OCHF_2$ | $SCH_2CH_3$ | $CH_3$ | F | $SCF_3$ | $SCH_2CH_3$ |
| $CH_3$ | F | $SCHF_2$ | $CF_3$ | $CH_3$ | F | $Cl$ | $CF_3$ |
| $CH_3$ | F | $SCHF_2$ | $OCF_3$ | $CH_3$ | F | $Cl$ | $OCF_3$ |
| $CH_3$ | F | $SCHF_2$ | $SCF_3$ | $CH_3$ | F | $Cl$ | $SCF_3$ |
| $CH_3$ | F | $SCHF_2$ | $OCHF_2$ | $CH_3$ | F | $Cl$ | $OCHF_2$ |
| $CH_3$ | F | $SCHF_2$ | $SCHF_2$ | $CH_3$ | F | $Cl$ | $SCHF_2$ |
| $CH_3$ | F | $SCHF_2$ | $C_2F_5$ | $CH_3$ | F | $Cl$ | $C_2F_5$ |
| $CH_3$ | F | $SCHF_2$ | $Cl$ | $CH_3$ | F | $Cl$ | $Cl$ |

TABLE 1-continued

| R¹ | R⁴ | R⁵ | R⁹ | R¹ | R⁴ | R⁵ | R⁹ |
|---|---|---|---|---|---|---|---|
| $CH_3$ | F | $SCHF_2$ | $SCH_2CH_3$ | $CH_3$ | F | Cl | $SCH_2CH_3$ |
| $CH_3$ | Cl | $CF_3$ | $CF_3$ | $CH_3$ | Cl | $OCF_3$ | $CF_3$ |
| $CH_3$ | Cl | $CF_3$ | $OCF_3$ | $CH_3$ | Cl | $OCF_3$ | $OCF_3$ |
| $CH_3$ | Cl | $CF_3$ | $SCF_3$ | $CH_3$ | Cl | $OCF_3$ | $SCF_3$ |
| $CH_3$ | Cl | $CF_3$ | $OCHF_2$ | $CH_3$ | Cl | $OCF_3$ | $OCHF_2$ |
| $CH_3$ | Cl | $CF_3$ | $SCHF_2$ | $CH_3$ | Cl | $OCF_3$ | $SCHF_2$ |
| $CH_3$ | Cl | $CF_3$ | $C_2F_5$ | $CH_3$ | Cl | $OCF_3$ | $C_2F_5$ |
| $CH_3$ | Cl | $CF_3$ | Cl | $CH_3$ | Cl | $OCF_3$ | Cl |
| $CH_3$ | Cl | $CF_3$ | $SCH_2CH_3$ | $CH_3$ | Cl | $OCF_3$ | $SCH_2CH_3$ |
| $CH_3$ | Cl | $OCHF_2$ | $CF_3$ | $CH_3$ | Cl | $SCF_3$ | $CF_3$ |
| $CH_3$ | Cl | $OCHF_2$ | $OCF_3$ | $CH_3$ | Cl | $SCF_3$ | $OCF_3$ |
| $CH_3$ | Cl | $OCHF_2$ | $SCF_3$ | $CH_3$ | Cl | $SCF_3$ | $SCF_3$ |
| $CH_3$ | Cl | $OCHF_2$ | $OCHF_2$ | $CH_3$ | Cl | $SCF_3$ | $OCHF_2$ |
| $CH_3$ | Cl | $OCHF_2$ | $SCHF_2$ | $CH_3$ | Cl | $SCF_3$ | $SCHF_2$ |
| $CH_3$ | Cl | $OCHF_2$ | $C_2F_5$ | $CH_3$ | Cl | $SCF_3$ | $C_2F_5$ |
| $CH_3$ | Cl | $OCHF_2$ | Cl | $CH_3$ | Cl | $SCF_3$ | Cl |
| $CH_3$ | Cl | $OCHF_2$ | $SCH_2CH_3$ | $CH_3$ | Cl | $SCF_3$ | $SCH_2CH_3$ |
| $CH_3$ | Cl | $SCHF_2$ | $CF_3$ | $CH_3$ | Cl | Cl | $CF_3$ |
| $CH_3$ | Cl | $SCHF_2$ | $OCF_3$ | $CH_3$ | Cl | Cl | $OCF_3$ |
| $CH_3$ | Cl | $SCHF_2$ | $SCF_3$ | $CH_3$ | Cl | Cl | $SCF_3$ |
| $CH_3$ | Cl | $SCHF_2$ | $OCHF_2$ | $CH_3$ | Cl | Cl | $OCHF_2$ |
| $CH_3$ | Cl | $SCHF_2$ | $SCHF_2$ | $CH_3$ | Cl | Cl | $SCHF_2$ |
| $CH_3$ | Cl | $SCHF_2$ | $C_2F_5$ | $CH_3$ | Cl | Cl | $C_2F_5$ |
| $CH_3$ | Cl | $SCHF_2$ | Cl | $CH_3$ | Cl | Cl | Cl |
| $CH_3$ | Cl | $SCHF_2$ | $SCH_2CH_3$ | $CH_3$ | Cl | Cl | $SCH_2CH_3$ |
| $OCH_3$ | H | $CF_3$ | $CF_3$ | $OCH_3$ | H | $OCF_3$ | $CF_3$ |
| $OCH_3$ | H | $CF_3$ | $OCF_3$ | $OCH_3$ | H | $OCF_3$ | $OCF_3$ |
| $OCH_3$ | H | $CF_3$ | $SCF_3$ | $OCH_3$ | H | $OCF_3$ | $SCF_3$ |
| $OCH_3$ | H | $CF_3$ | $OCHF_2$ | $OCH_3$ | H | $OCF_3$ | $OCHF_2$ |
| $OCH_3$ | H | $CF_3$ | $SCHF_2$ | $OCH_3$ | H | $OCF_3$ | $SCHF_2$ |
| $OCH_3$ | H | $CF_3$ | $C_2F_5$ | $OCH_3$ | H | $OCF_3$ | $C_2F_5$ |
| $OCH_3$ | H | $CF_3$ | Cl | $OCH_3$ | H | $OCF_3$ | Cl |
| $OCH_3$ | H | $CF_3$ | $SCH_2CH_3$ | $OCH_3$ | H | $OCF_3$ | $SCH_2CH_3$ |
| $OCH_3$ | H | $OCHF_2$ | $CF_3$ | $OCH_3$ | H | $SCF_3$ | $CF_3$ |
| $OCH_3$ | H | $OCHF_2$ | $OCF_3$ | $OCH_3$ | H | $SCF_3$ | $OCF_3$ |
| $OCH_3$ | H | $OCHF_2$ | $SCF_3$ | $OCH_3$ | H | $SCF_3$ | $SCF_3$ |
| $OCH_3$ | H | $OCHF_2$ | $OCHF_2$ | $OCH_3$ | H | $SCF_3$ | $OCHF_2$ |
| $OCH_3$ | H | $OCHF_2$ | $SCHF_2$ | $OCH_3$ | H | $SCF_3$ | $SCHF_2$ |
| $OCH_3$ | H | $OCHF_2$ | $C_2F_5$ | $OCH_3$ | H | $SCF_3$ | $C_2F_5$ |
| $OCH_3$ | H | $OCHF_2$ | Cl | $OCH_3$ | H | $SCF_3$ | Cl |
| $OCH_3$ | H | $OCHF_2$ | $SCH_2CH_3$ | $OCH_3$ | H | $SCF_3$ | $SCH_2CH_3$ |
| $OCH_3$ | H | $SCHF_2$ | $CF_3$ | $OCH_3$ | H | Cl | $CF_3$ |
| $OCH_3$ | H | $SCHF_2$ | $OCF_3$ | $OCH_3$ | H | Cl | $OCF_3$ |
| $OCH_3$ | H | $SCHF_2$ | $SCF_3$ | $OCH_3$ | H | Cl | $SCF_3$ |
| $OCH_3$ | H | $SCHF_2$ | $OCHF_2$ | $OCH_3$ | H | Cl | $OCHF_2$ |
| $OCH_3$ | H | $SCHF_2$ | $SCHF_2$ | $OCH_3$ | H | Cl | $SCHF_2$ |
| $OCH_3$ | H | $SCHF_2$ | $C_2F_5$ | $OCH_3$ | H | Cl | $C_2F_5$ |
| $OCH_3$ | H | $SCHF_2$ | Cl | $OCH_3$ | H | Cl | Cl |
| $OCH_3$ | H | $SCHF_2$ | $SCH_2CH_3$ | $OCH_3$ | H | Cl | $SCH_2CH_3$ |
| $OCH_3$ | $CH_3$ | $CF_3$ | $CF_3$ | $OCH_3$ | $CH_3$ | $OCF_3$ | $CF_3$ |
| $OCH_3$ | $CH_3$ | $CF_3$ | $OCF_3$ | $OCH_3$ | $CH_3$ | $OCF_3$ | $OCF_3$ |
| $OCH_3$ | $CH_3$ | $CF_3$ | $SCF_3$ | $OCH_3$ | $CH_3$ | $OCF_3$ | $SCF_3$ |
| $OCH_3$ | $CH_3$ | $CF_3$ | $OCHF_2$ | $OCH_3$ | $CH_3$ | $OCF_3$ | $OCHF_2$ |
| $OCH_3$ | $CH_3$ | $CF_3$ | $SCHF_2$ | $OCH_3$ | $CH_3$ | $OCF_3$ | $SCHF_2$ |
| $OCH_3$ | $CH_3$ | $CF_3$ | $C_2F_5$ | $OCH_3$ | $CH_3$ | $OCF_3$ | $C_2F_5$ |
| $OCH_3$ | $CH_3$ | $CF_3$ | Cl | $OCH_3$ | $CH_3$ | $OCF_3$ | Cl |
| $OCH_3$ | $CH_3$ | $CF_3$ | $SCH_2CH_3$ | $OCH_3$ | $CH_3$ | $OCF_3$ | $SCH_2CH_3$ |
| $OCH_3$ | $CH_3$ | $OCHF_2$ | $CF_3$ | $OCH_3$ | $CH_3$ | $SCF_3$ | $CF_3$ |
| $OCH_3$ | $CH_3$ | $OCHF_2$ | $OCF_3$ | $OCH_3$ | $CH_3$ | $SCF_3$ | $OCF_3$ |
| $OCH_3$ | $CH_3$ | $OCHF_2$ | $SCF_3$ | $OCH_3$ | $CH_3$ | $SCF_3$ | $SCF_3$ |
| $OCH_3$ | $CH_3$ | $OCHF_2$ | $OCHF_2$ | $OCH_3$ | $CH_3$ | $SCF_3$ | $OCHF_2$ |
| $OCH_3$ | $CH_3$ | $OCHF_2$ | $SCHF_2$ | $OCH_3$ | $CH_3$ | $SCF_3$ | $SCHF_2$ |
| $OCH_3$ | $CH_3$ | $OCHF_2$ | $C_2F_5$ | $OCH_3$ | $CH_3$ | $SCF_3$ | $C_2F_5$ |
| $OCH_3$ | $CH_3$ | $OCHF_2$ | Cl | $OCH_3$ | $CH_3$ | $SCF_3$ | Cl |
| $OCH_3$ | $CH_3$ | $OCHF_2$ | $SCH_2CH_3$ | $OCH_3$ | $CH_3$ | $SCF_3$ | $SCH_2CH_3$ |
| $OCH_3$ | $CH_3$ | $SCHF_2$ | $CF_3$ | $OCH_3$ | $CH_3$ | Cl | $CF_3$ |
| $OCH_3$ | $CH_3$ | $SCHF_2$ | $OCF_3$ | $OCH_3$ | $CH_3$ | Cl | $OCF_3$ |

TABLE 1-continued

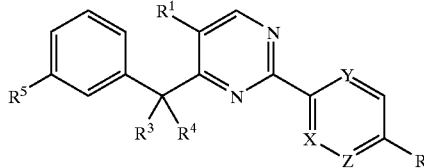

| $R^1$ | $R^4$ | $R^5$ | $R^9$ | $R^1$ | $R^4$ | $R^5$ | $R^9$ |
|---|---|---|---|---|---|---|---|
| $OCH_3$ | $CH_3$ | $SCHF_2$ | $SCF_3$ | $OCH_3$ | $CH_3$ | Cl | $SCF_3$ |
| $OCH_3$ | $CH_3$ | $SCHF_2$ | $OCHF_2$ | $OCH_3$ | $CH_3$ | Cl | $OCHF_2$ |
| $OCH_3$ | $CH_3$ | $SCHF_2$ | $SCHF_2$ | $OCH_3$ | $CH_3$ | Cl | $SCHF_2$ |
| $OCH_3$ | $CH_3$ | $SCHF_2$ | $C_2F_5$ | $OCH_3$ | $CH_3$ | Cl | $C_2F_5$ |
| $OCH_3$ | $CH_3$ | $SCHF_2$ | Cl | $OCH_3$ | $CH_3$ | Cl | Cl |
| $OCH_3$ | $CH_3$ | $SCHF_2$ | $SCH_2CH_3$ | $OCH_3$ | $CH_3$ | Cl | $SCH_2CH_3$ |
| $OCH_3$ | F | $CF_3$ | $CF_3$ | $OCH_3$ | F | $OCF_3$ | $CF_3$ |
| $OCH_3$ | F | $CF_3$ | $OCF_3$ | $OCH_3$ | F | $OCF_3$ | $OCF_3$ |
| $OCH_3$ | F | $CF_3$ | $SCF_3$ | $OCH_3$ | F | $OCF_3$ | $SCF_3$ |
| $OCH_3$ | F | $CF_3$ | $OCHF_2$ | $OCH_3$ | F | $OCF_3$ | $OCHF_2$ |
| $OCH_3$ | F | $CF_3$ | $SCHF_2$ | $OCH_3$ | F | $OCF_3$ | $SCHF_2$ |
| $OCH_3$ | F | $CF_3$ | $C_2F_5$ | $OCH_3$ | F | $OCF_3$ | $C_2F_5$ |
| $OCH_3$ | F | $CF_3$ | Cl | $OCH_3$ | F | $OCF_3$ | Cl |
| $OCH_3$ | F | $CF_3$ | $SCH_2CH_3$ | $OCH_3$ | F | $OCF_3$ | $SCH_2CH_3$ |
| $OCH_3$ | F | $OCHF_2$ | $CF_3$ | $OCH_3$ | F | $SCF_3$ | $CF_3$ |
| $OCH_3$ | F | $OCHF_2$ | $OCF_3$ | $OCH_3$ | F | $SCF_3$ | $OCF_3$ |
| $OCH_3$ | F | $OCHF_2$ | $SCF_3$ | $OCH_3$ | F | $SCF_3$ | $SCF_3$ |
| $OCH_3$ | F | $OCHF_2$ | $OCHF_2$ | $OCH_3$ | F | $SCF_3$ | $OCHF_2$ |
| $OCH_3$ | F | $OCHF_2$ | $SCHF_2$ | $OCH_3$ | F | $SCF_3$ | $SCHF_2$ |
| $OCH_3$ | F | $OCHF_2$ | $C_2F_5$ | $OCH_3$ | F | $SCF_3$ | $C_2F_5$ |
| $OCH_3$ | F | $OCHF_2$ | Cl | $OCH_3$ | F | $SCF_3$ | Cl |
| $OCH_3$ | F | $OCHF_2$ | $SCH_2CH_3$ | $OCH_3$ | F | $SCF_3$ | $SCH_2CH_3$ |
| $OCH_3$ | F | $SCHF_2$ | $CF_3$ | $OCH_3$ | F | Cl | $CF_3$ |
| $OCH_3$ | F | $SCHF_2$ | $OCF_3$ | $OCH_3$ | F | Cl | $OCF_3$ |
| $OCH_3$ | F | $SCHF_2$ | $SCF_3$ | $OCH_3$ | F | Cl | $SCF_3$ |
| $OCH_3$ | F | $SCHF_2$ | $OCHF_2$ | $OCH_3$ | F | Cl | $OCHF_2$ |
| $OCH_3$ | F | $SCHF_2$ | $SCHF_2$ | $OCH_3$ | F | Cl | $SCHF_2$ |
| $OCH_3$ | F | $SCHF_2$ | $C_2F_5$ | $OCH_3$ | F | Cl | $C_2F_5$ |
| $OCH_3$ | F | $SCHF_2$ | Cl | $OCH_3$ | F | Cl | Cl |
| $OCH_3$ | F | $SCHF_2$ | $SCH_2CH_3$ | $OCH_3$ | F | Cl | $SCH_2CH_3$ |
| $OCH_3$ | Cl | $CF_3$ | $CF_3$ | $OCH_3$ | Cl | $OCF_3$ | $CF_3$ |
| $OCH_3$ | Cl | $CF_3$ | $OCF_3$ | $OCH_3$ | Cl | $OCF_3$ | $OCF_3$ |
| $OCH_3$ | Cl | $CF_3$ | $SCF_3$ | $OCH_3$ | Cl | $OCF_3$ | $SCF_3$ |
| $OCH_3$ | Cl | $CF_3$ | $OCHF_2$ | $OCH_3$ | Cl | $OCF_3$ | $OCHF_2$ |
| $OCH_3$ | Cl | $CF_3$ | $SCHF_2$ | $OCH_3$ | Cl | $OCF_3$ | $SCHF_2$ |
| $OCH_3$ | Cl | $CF_3$ | $C_2F_5$ | $OCH_3$ | Cl | $OCF_3$ | $C_2F_5$ |
| $OCH_3$ | Cl | $CF_3$ | Cl | $OCH_3$ | Cl | $OCF_3$ | Cl |
| $OCH_3$ | Cl | $CF_3$ | $SCH_2CH_3$ | $OCH_3$ | Cl | $OCF_3$ | $SCH_2CH_3$ |
| $OCH_3$ | Cl | $OCHF_2$ | $CF_3$ | $OCH_3$ | Cl | $SCF_3$ | $CF_3$ |
| $OCH_3$ | Cl | $OCHF_2$ | $OCF_3$ | $OCH_3$ | Cl | $SCF_3$ | $OCF_3$ |
| $OCH_3$ | Cl | $OCHF_2$ | $SCF_3$ | $OCH_3$ | Cl | $SCF_3$ | $SCF_3$ |
| $OCH_3$ | Cl | $OCHF_2$ | $OCHF_2$ | $OCH_3$ | Cl | $SCF_3$ | $OCHF_2$ |
| $OCH_3$ | Cl | $OCHF_2$ | $SCHF_2$ | $OCH_3$ | Cl | $SCF_3$ | $SCHF_2$ |
| $OCH_3$ | Cl | $OCHF_2$ | $C_2F_5$ | $OCH_3$ | Cl | $SCF_3$ | $C_2F_5$ |
| $OCH_3$ | Cl | $OCHF_2$ | Cl | $OCH_3$ | Cl | $SCF_3$ | Cl |
| $OCH_3$ | Cl | $OCHF_2$ | $SCH_2CH_3$ | $OCH_3$ | Cl | $SCF_3$ | $SCH_2CH_3$ |
| $OCH_3$ | Cl | $SCHF_2$ | $CF_3$ | $OCH_3$ | Cl | Cl | $CF_3$ |
| $OCH_3$ | Cl | $SCHF_2$ | $OCF_3$ | $OCH_3$ | Cl | Cl | $OCF_3$ |
| $OCH_3$ | Cl | $SCHF_2$ | $SCF_3$ | $OCH_3$ | Cl | Cl | $SCF_3$ |
| $OCH_3$ | Cl | $SCHF_2$ | $OCHF_2$ | $OCH_3$ | Cl | Cl | $OCHF_2$ |
| $OCH_3$ | Cl | $SCHF_2$ | $SCHF_2$ | $OCH_3$ | Cl | Cl | $SCHF_2$ |
| $OCH_3$ | Cl | $SCHF_2$ | $C_2F_5$ | $OCH_3$ | Cl | Cl | $C_2F_5$ |
| $OCH_3$ | Cl | $SCHF_2$ | Cl | $OCH_3$ | Cl | Cl | Cl |
| $OCH_3$ | Cl | $SCHF_2$ | $SCH_2CH_3$ | $OCH_3$ | Cl | Cl | $SCH_2CH_3$ |
| $CH_2CH_3$ | H | $CF_3$ | $CF_3$ | $CH_2CH_3$ | H | $OCF_3$ | $CF_3$ |
| $CH_2CH_3$ | H | $CF_3$ | $OCF_3$ | $CH_2CH_3$ | H | $OCF_3$ | $OCF_3$ |
| $CH_2CH_3$ | H | $CF_3$ | $SCF_3$ | $CH_2CH_3$ | H | $OCF_3$ | $SCF_3$ |
| $CH_2CH_3$ | H | $CF_3$ | $OCHF_2$ | $CH_2CH_3$ | H | $OCF_3$ | $OCHF_2$ |
| $CH_2CH_3$ | H | $CF_3$ | $SCHF_2$ | $CH_2CH_3$ | H | $OCF_3$ | $SCHF_2$ |
| $CH_2CH_3$ | H | $CF_3$ | $C_2F_5$ | $CH_2CH_3$ | H | $OCF_3$ | $C_2F_5$ |
| $CH_2CH_3$ | H | $CF_3$ | Cl | $CH_2CH_3$ | H | $OCF_3$ | Cl |
| $CH_2CH_3$ | H | $CF_3$ | $SCH_2CH_3$ | $CH_2CH_3$ | H | $OCF_3$ | $SCH_2CH_3$ |
| $CH_2CH_3$ | H | $OCHF_2$ | $CF_3$ | $CH_2CH_3$ | H | $SCF_3$ | $CF_3$ |
| $CH_2CH_3$ | H | $OCHF_2$ | $OCF_3$ | $CH_2CH_3$ | H | $SCF_3$ | $OCF_3$ |
| $CH_2CH_3$ | H | $OCHF_2$ | $SCF_3$ | $CH_2CH_3$ | H | $SCF_3$ | $SCF_3$ |
| $CH_2CH_3$ | H | $OCHF_2$ | $OCHF_2$ | $CH_2CH_3$ | H | $SCF_3$ | $OCHF_2$ |
| $CH_2CH_3$ | H | $OCHF_2$ | $SCHF_2$ | $CH_2CH_3$ | H | $SCF_3$ | $SCHF_2$ |

TABLE 1-continued

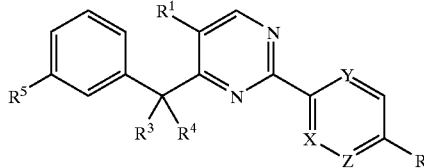

| R¹ | R⁴ | R⁵ | R⁹ | R¹ | R⁴ | R⁵ | R⁹ |
|---|---|---|---|---|---|---|---|
| CH₂CH₃ | H | OCHF₂ | C₂F₅ | CH₂CH₃ | H | SCF₃ | C₂F₅ |
| CH₂CH₃ | H | OCHF₂ | Cl | CH₂CH₃ | H | SCF₃ | Cl |
| CH₂CH₃ | H | OCHF₂ | SCH₂CH₃ | CH₂CH₃ | H | SCF₃ | SCH₂CH₃ |
| CH₂CH₃ | H | SCHF₂ | CF₃ | CH₂CH₃ | H | Cl | CF₃ |
| CH₂CH₃ | H | SCHF₂ | OCF₃ | CH₂CH₃ | H | Cl | OCF₃ |
| CH₂CH₃ | H | SCHF₂ | SCF₃ | CH₂CH₃ | H | Cl | SCF₃ |
| CH₂CH₃ | H | SCHF₂ | OCHF₂ | CH₂CH₃ | H | Cl | OCHF₂ |
| CH₂CH₃ | H | SCHF₂ | SCHF₂ | CH₂CH₃ | H | Cl | SCHF₂ |
| CH₂CH₃ | H | SCHF₂ | C₂F₅ | CH₂CH₃ | H | Cl | C₂F₅ |
| CH₂CH₃ | H | SCHF₂ | Cl | CH₂CH₃ | H | Cl | Cl |
| CH₂CH₃ | H | SCHF₂ | SCH₂CH₃ | CH₂CH₃ | H | Cl | SCH₂CH₃ |
| CH₂CH₃ | CH₃ | CF₃ | CF₃ | CH₂CH₃ | CH₃ | OCF₃ | CF₃ |
| CH₂CH₃ | CH₃ | CF₃ | OCF₃ | CH₂CH₃ | CH₃ | OCF₃ | OCF₃ |
| CH₂CH₃ | CH₃ | CF₃ | SCF₃ | CH₂CH₃ | CH₃ | OCF₃ | SCF₃ |
| CH₂CH₃ | CH₃ | CF₃ | OCHF₂ | CH₂CH₃ | CH₃ | OCF₃ | OCHF₂ |
| CH₂CH₃ | CH₃ | CF₃ | SCHF₂ | CH₂CH₃ | CH₃ | OCF₃ | SCHF₂ |
| CH₂CH₃ | CH₃ | CF₃ | C₂F₅ | CH₂CH₃ | CH₃ | OCF₃ | C₂F₅ |
| CH₂CH₃ | CH₃ | CF₃ | Cl | CH₂CH₃ | CH₃ | OCF₃ | Cl |
| CH₂CH₃ | CH₃ | CF₃ | SCH₂CH₃ | CH₂CH₃ | CH₃ | OCF₃ | SCH₂CH₃ |
| CH₂CH₃ | CH₃ | OCHF₂ | CF₃ | CH₂CH₃ | CH₃ | SCF₃ | CF₃ |
| CH₂CH₃ | CH₃ | OCHF₂ | OCF₃ | CH₂CH₃ | CH₃ | SCF₃ | OCF₃ |
| CH₂CH₃ | CH₃ | OCHF₂ | SCF₃ | CH₂CH₃ | CH₃ | SCF₃ | SCF₃ |
| CH₂CH₃ | CH₃ | OCHF₂ | OCHF₂ | CH₂CH₃ | CH₃ | SCF₃ | OCHF₂ |
| CH₂CH₃ | CH₃ | OCHF₂ | SCHF₂ | CH₂CH₃ | CH₃ | SCF₃ | SCHF₂ |
| CH₂CH₃ | CH₃ | OCHF₂ | C₂F₅ | CH₂CH₃ | CH₃ | SCF₃ | C₂F₅ |
| CH₂CH₃ | CH₃ | OCHF₂ | Cl | CH₂CH₃ | CH₃ | SCF₃ | Cl |
| CH₂CH₃ | CH₃ | OCHF₂ | SCH₂CH₃ | CH₂CH₃ | CH₃ | SCF₃ | SCH₂CH₃ |
| CH₂CH₃ | CH₃ | SCHF₂ | CF₃ | CH₂CH₃ | CH₃ | Cl | CF₃ |
| CH₂CH₃ | CH₃ | SCHF₂ | OCF₃ | CH₂CH₃ | CH₃ | Cl | OCF₃ |
| CH₂CH₃ | CH₃ | SCHF₂ | SCF₃ | CH₂CH₃ | CH₃ | Cl | SCF₃ |
| CH₂CH₃ | CH₃ | SCHF₂ | OCHF₂ | CH₂CH₃ | CH₃ | Cl | OCHF₂ |
| CH₂CH₃ | CH₃ | SCHF₂ | SCHF₂ | CH₂CH₃ | CH₃ | Cl | SCHF₂ |
| CH₂CH₃ | CH₃ | SCHF₂ | C₂F₅ | CH₂CH₃ | CH₃ | Cl | C₂F₅ |
| CH₂CH₃ | CH₃ | SCHF₂ | Cl | CH₂CH₃ | CH₃ | Cl | Cl |
| CH₂CH₃ | CH₃ | SCHF₂ | SCH₂CH₃ | CH₂CH₃ | CH₃ | Cl | SCH₂CH₃ |
| CH₂CH₃ | F | CF₃ | CF₃ | CH₂CH₃ | F | OCF₃ | CF₃ |
| CH₂CH₃ | F | CF₃ | OCF₃ | CH₂CH₃ | F | OCF₃ | OCF₃ |
| CH₂CH₃ | F | CF₃ | SCF₃ | CH₂CH₃ | F | OCF₃ | SCF₃ |
| CH₂CH₃ | F | CF₃ | OCHF₂ | CH₂CH₃ | F | OCF₃ | OCHF₂ |
| CH₂CH₃ | F | CF₃ | SCHF₂ | CH₂CH₃ | F | OCF₃ | SCHF₂ |
| CH₂CH₃ | F | CF₃ | C₂F₅ | CH₂CH₃ | F | OCF₃ | C₂F₅ |
| CH₂CH₃ | F | CF₃ | Cl | CH₂CH₃ | F | OCF₃ | Cl |
| CH₂CH₃ | F | CF₃ | SCH₂CH₃ | CH₂CH₃ | F | OCF₃ | SCH₂CH₃ |
| CH₂CH₃ | F | OCHF₂ | CF₃ | CH₂CH₃ | F | SCF₃ | CF₃ |
| CH₂CH₃ | F | OCHF₂ | OCF₃ | CH₂CH₃ | F | SCF₃ | OCF₃ |
| CH₂CH₃ | F | OCHF₂ | SCF₃ | CH₂CH₃ | F | SCF₃ | SCF₃ |
| CH₂CH₃ | F | OCHF₂ | OCHF₂ | CH₂CH₃ | F | SCF₃ | OCHF₂ |
| CH₂CH₃ | F | OCHF₂ | SCHF₂ | CH₂CH₃ | F | SCF₃ | SCHF₂ |
| CH₂CH₃ | F | OCHF₂ | C₂F₅ | CH₂CH₃ | F | SCF₃ | C₂F₅ |
| CH₂CH₃ | F | OCHF₂ | Cl | CH₂CH₃ | F | SCF₃ | Cl |
| CH₂CH₃ | F | OCHF₂ | SCH₂CH₃ | CH₂CH₃ | F | SCF₃ | SCH₂CH₃ |
| CH₂CH₃ | F | SCHF₂ | CF₃ | CH₂CH₃ | F | Cl | CF₃ |
| CH₂CH₃ | F | SCHF₂ | OCF₃ | CH₂CH₃ | F | Cl | OCF₃ |
| CH₂CH₃ | F | SCHF₂ | SCF₃ | CH₂CH₃ | F | Cl | SCF₃ |
| CH₂CH₃ | F | SCHF₂ | OCHF₂ | CH₂CH₃ | F | Cl | OCHF₂ |
| CH₂CH₃ | F | SCHF₂ | SCHF₂ | CH₂CH₃ | F | Cl | SCHF₂ |
| CH₂CH₃ | F | SCHF₂ | C₂F₅ | CH₂CH₃ | F | Cl | C₂F₅ |
| CH₂CH₃ | F | SCHF₂ | Cl | CH₂CH₃ | F | Cl | Cl |
| CH₂CH₃ | F | SCHF₂ | SCH₂CH₃ | CH₂CH₃ | F | Cl | SCH₂CH₃ |
| CH₂CH₃ | Cl | CF₃ | CF₃ | CH₂CH₃ | Cl | OCF₃ | CF₃ |
| CH₂CH₃ | Cl | CF₃ | OCF₃ | CH₂CH₃ | Cl | OCF₃ | OCF₃ |
| CH₂CH₃ | Cl | CF₃ | SCF₃ | CH₂CH₃ | Cl | OCF₃ | SCF₃ |
| CH₂CH₃ | Cl | CF₃ | OCHF₂ | CH₂CH₃ | Cl | OCF₃ | OCHF₂ |
| CH₂CH₃ | Cl | CF₃ | SCHF₂ | CH₂CH₃ | Cl | OCF₃ | SCHF₂ |
| CH₂CH₃ | Cl | CF₃ | C₂F₅ | CH₂CH₃ | Cl | OCF₃ | C₂F₅ |
| CH₂CH₃ | Cl | CF₃ | Cl | CH₂CH₃ | Cl | OCF₃ | Cl |
| CH₂CH₃ | Cl | CF₃ | SCH₂CH₃ | CH₂CH₃ | Cl | OCF₃ | SCH₂CH₃ |

TABLE 1-continued

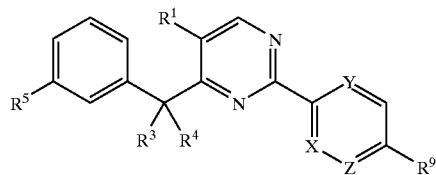

| R¹ | R⁴ | R⁵ | R⁹ | R¹ | R⁴ | R⁵ | R⁹ |
|---|---|---|---|---|---|---|---|
| CH₂CH₃ | Cl | OCHF₂ | CF₃ | CH₂CH₃ | Cl | SCF₃ | CF₃ |
| CH₂CH₃ | Cl | OCHF₂ | OCF₃ | CH₂CH₃ | Cl | SCF₃ | OCF₃ |
| CH₂CH₃ | Cl | OCHF₂ | SCF₃ | CH₂CH₃ | Cl | SCF₃ | SCF₃ |
| CH₂CH₃ | Cl | OCHF₂ | OCHF₂ | CH₂CH₃ | Cl | SCF₃ | OCHF₂ |
| CH₂CH₃ | Cl | OCHF₂ | SCHF₂ | CH₂CH₃ | Cl | SCF₃ | SCHF₂ |
| CH₂CH₃ | Cl | OCHF₂ | C₂F₅ | CH₂CH₃ | Cl | SCF₃ | C₂F₅ |
| CH₂CH₃ | Cl | OCHF₂ | Cl | CH₂CH₃ | Cl | SCF₃ | Cl |
| CH₂CH₃ | Cl | OCHF₂ | SCH₂CH₃ | CH₂CH₃ | Cl | SCF₃ | SCH₂CH₃ |
| CH₂CH₃ | Cl | SCHF₂ | CF₃ | CH₂CH₃ | Cl | Cl | CF₃ |
| CH₂CH₃ | Cl | SCHF₂ | OCF₃ | CH₂CH₃ | Cl | Cl | OCF₃ |
| CH₂CH₃ | Cl | SCHF₂ | SCF₃ | CH₂CH₃ | Cl | Cl | SCF₃ |
| CH₂CH₃ | Cl | SCHF₂ | OCHF₂ | CH₂CH₃ | Cl | Cl | OCHF₂ |
| CH₂CH₃ | Cl | SCHF₂ | SCHF₂ | CH₂CH₃ | Cl | Cl | SCHF₂ |
| CH₂CH₃ | Cl | SCHF₂ | C₂F₅ | CH₂CH₃ | Cl | Cl | C₂F₅ |
| CH₂CH₃ | Cl | SCHF₂ | Cl | CH₂CH₃ | Cl | Cl | Cl |
| CH₂CH₃ | Cl | SCHF₂ | SCH₂CH₃ | CH₂CH₃ | Cl | Cl | SCH₂CH₃ |

R³ is F

| R¹ | R⁴ | R⁵ | R⁹ | R¹ | R⁴ | R⁵ | R⁹ |
|---|---|---|---|---|---|---|---|
| H | F | CF₃ | CF₃ | H | F | OCF₃ | CF₃ |
| H | F | CF₃ | OCF₃ | H | F | OCF₃ | OCF₃ |
| H | F | CF₃ | SCF₃ | H | F | OCF₃ | SCF₃ |
| H | F | CF₃ | OCHF₂ | H | F | OCF₃ | OCHF₂ |
| H | F | CF₃ | SCHF₂ | H | F | OCF₃ | SCHF₂ |
| H | F | CF₃ | C₂F₅ | H | F | OCF₃ | C₂F₅ |
| H | F | CF₃ | Cl | H | F | OCF₃ | Cl |
| H | F | CF₃ | SCH₂CH₃ | H | F | OCF₃ | SCH₂CH₃ |
| H | F | OCHF₂ | CF₃ | H | F | SCF₃ | CF₃ |
| H | F | OCHF₂ | OCF₃ | H | F | SCF₃ | OCF₃ |
| H | F | OCHF₂ | SCF₃ | H | F | SCF₃ | SCF₃ |
| H | F | OCHF₂ | OCHF₂ | H | F | SCF₃ | OCHF₂ |
| H | F | OCHF₂ | SCHF₂ | H | F | SCF₃ | SCHF₂ |
| H | F | OCHF₂ | C₂F₅ | H | F | SCF₃ | C₂F₅ |
| H | F | OCHF₂ | Cl | H | F | SCF₃ | Cl |
| H | F | OCHF₂ | SCH₂CH₃ | H | F | SCF₃ | SCH₂CH₃ |
| H | F | SCHF₂ | CF₃ | H | F | Cl | CF₃ |
| H | F | SCHF₂ | OCF₃ | H | F | Cl | OCF₃ |
| H | F | SCHF₂ | SCF₃ | H | F | Cl | SCF₃ |
| H | F | SCHF₂ | OCHF₂ | H | F | Cl | OCHF₂ |
| H | F | SCHF₂ | SCHF₂ | H | F | Cl | SCHF₂ |
| H | F | SCHF₂ | C₂F₅ | H | F | Cl | C₂F₅ |
| H | F | SCHF₂ | Cl | H | F | Cl | Cl |
| H | F | SCHF₂ | SCH₂CH₃ | H | F | Cl | SCH₂CH₃ |
| CH₃ | F | CF₃ | CF₃ | CH₃ | F | OCF₃ | CF₃ |
| CH₃ | F | CF₃ | OCF₃ | CH₃ | F | OCF₃ | OCF₃ |
| CH₃ | F | CF₃ | SCF₃ | CH₃ | F | OCF₃ | SCF₃ |
| CH₃ | F | CF₃ | OCHF₂ | CH₃ | F | OCF₃ | OCHF₂ |
| CH₃ | F | CF₃ | SCHF₂ | CH₃ | F | OCF₃ | SCHF₂ |
| CH₃ | F | CF₃ | C₂F₅ | CH₃ | F | OCF₃ | C₂F₅ |
| CH₃ | F | CF₃ | Cl | CH₃ | F | OCF₃ | Cl |
| CH₃ | F | CF₃ | SCH₂CH₃ | CH₃ | F | OCF₃ | SCH₂CH₃ |
| CH₃ | F | OCHF₂ | CF₃ | CH₃ | F | SCF₃ | CF₃ |
| CH₃ | F | OCHF₂ | OCF₃ | CH₃ | F | SCF₃ | OCF₃ |
| CH₃ | F | OCHF₂ | SCF₃ | CH₃ | F | SCF₃ | SCF₃ |
| CH₃ | F | OCHF₂ | OCHF₂ | CH₃ | F | SCF₃ | OCHF₂ |
| CH₃ | F | OCHF₂ | SCHF₂ | CH₃ | F | SCF₃ | SCHF₂ |
| CH₃ | F | OCHF₂ | C₂F₅ | CH₃ | F | SCF₃ | C₂F₅ |
| CH₃ | F | OCHF₂ | Cl | CH₃ | F | SCF₃ | Cl |
| CH₃ | F | OCHF₂ | SCH₂CH₃ | CH₃ | F | SCF₃ | SCH₂CH₃ |
| CH₃ | F | SCHF₂ | CF₃ | CH₃ | F | Cl | CF₃ |
| CH₃ | F | SCHF₂ | OCF₃ | CH₃ | F | Cl | OCF₃ |
| CH₃ | F | SCHF₂ | SCF₃ | CH₃ | F | Cl | SCF₃ |
| CH₃ | F | SCHF₂ | OCHF₂ | CH₃ | F | Cl | OCHF₂ |
| CH₃ | F | SCHF₂ | SCHF₂ | CH₃ | F | Cl | SCHF₂ |
| CH₃ | F | SCHF₂ | C₂F₅ | CH₃ | F | Cl | C₂F₅ |
| CH₃ | F | SCHF₂ | Cl | CH₃ | F | Cl | Cl |
| CH₃ | F | SCHF₂ | SCH₂CH₃ | CH₃ | F | Cl | SCH₂CH₃ |
| OCH₃ | F | CF₃ | CF₃ | OCH₃ | F | OCF₃ | CF₃ |

TABLE 1-continued

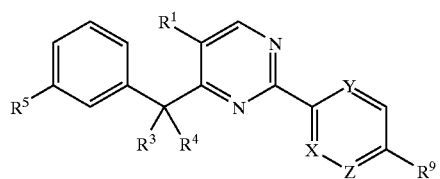

| R¹ | R⁴ | R⁵ | R⁹ | R¹ | R⁴ | R⁵ | R⁹ |
|---|---|---|---|---|---|---|---|
| OCH₃ | F | CF₃ | OCF₃ | OCH₃ | F | OCF₃ | OCF₃ |
| OCH₃ | F | CF₃ | SCF₃ | OCH₃ | F | OCF₃ | SCF₃ |
| OCH₃ | F | CF₃ | OCHF₂ | OCH₃ | F | OCF₃ | OCHF₂ |
| OCH₃ | F | CF₃ | SCHF₂ | OCH₃ | F | OCF₃ | SCHF₂ |
| OCH₃ | F | CF₃ | C₂F₅ | OCH₃ | F | OCF₃ | C₂F₅ |
| OCH₃ | F | CF₃ | Cl | OCH₃ | F | OCF₃ | Cl |
| OCH₃ | F | CF₃ | SCH₂CH₃ | OCH₃ | F | OCF₃ | SCH₂CH₃ |
| OCH₃ | F | OCHF₂ | CF₃ | OCH₃ | F | SCF₃ | CF₃ |
| OCH₃ | F | OCHF₂ | OCF₃ | OCH₃ | F | SCF₃ | OCF₃ |
| OCH₃ | F | OCHF₂ | SCF₃ | OCH₃ | F | SCF₃ | SCF₃ |
| OCH₃ | F | OCHF₂ | OCHF₂ | OCH₃ | F | SCF₃ | OCHF₂ |
| OCH₃ | F | OCHF₂ | SCHF₂ | OCH₃ | F | SCF₃ | SCHF₂ |
| OCH₃ | F | OCHF₂ | C₂F₅ | OCH₃ | F | SCF₃ | C₂F₅ |
| OCH₃ | F | OCHF₂ | Cl | OCH₃ | F | SCF₃ | Cl |
| OCH₃ | F | OCHF₂ | SCH₂CH₃ | OCH₃ | F | SCF₃ | SCH₂CH₃ |
| OCH₃ | F | SCHF₂ | CF₃ | OCH₃ | F | Cl | CF₃ |
| OCH₃ | F | SCHF₂ | OCF₃ | OCH₃ | F | Cl | OCF₃ |
| OCH₃ | F | SCHF₂ | SCF₃ | OCH₃ | F | Cl | SCF₃ |
| OCH₃ | F | SCHF₂ | OCHF₂ | OCH₃ | F | Cl | OCHF₂ |
| OCH₃ | F | SCHF₂ | SCHF₂ | OCH₃ | F | Cl | SCHF₂ |
| OCH₃ | F | SCHF₂ | C₂F₅ | OCH₃ | F | Cl | C₂F₅ |
| OCH₃ | F | SCHF₂ | Cl | OCH₃ | F | Cl | Cl |
| OCH₃ | F | SCHF₂ | SCH₂CH₃ | OCH₃ | F | Cl | SCH₂CH₃ |
| CH₂CH₃ | F | CF₃ | CF₃ | CH₂CH₃ | F | OCF₃ | CF₃ |
| CH₂CH₃ | F | CF₃ | OCF₃ | CH₂CH₃ | F | OCF₃ | OCF₃ |
| CH₂CH₃ | F | CF₃ | SCF₃ | CH₂CH₃ | F | OCF₃ | SCF₃ |
| CH₂CH₃ | F | CF₃ | OCHF₂ | CH₂CH₃ | F | OCF₃ | OCHF₂ |
| CH₂CH₃ | F | CF₃ | SCHF₂ | CH₂CH₃ | F | OCF₃ | SCHF₂ |
| CH₂CH₃ | F | CF₃ | C₂F₅ | CH₂CH₃ | F | OCF₃ | C₂F₅ |
| CH₂CH₃ | F | CF₃ | Cl | CH₂CH₃ | F | OCF₃ | Cl |
| CH₂CH₃ | F | CF₃ | SCH₂CH₃ | CH₂CH₃ | F | OCF₃ | SCH₂CH₃ |
| CH₂CH₃ | F | OCHF₂ | CF₃ | CH₂CH₃ | F | SCF₃ | CF₃ |
| CH₂CH₃ | F | OCHF₂ | OCF₃ | CH₂CH₃ | F | SCF₃ | OCF₃ |
| CH₂CH₃ | F | OCHF₂ | SCF₃ | CH₂CH₃ | F | SCF₃ | SCF₃ |
| CH₂CH₃ | F | OCHF₂ | OCHF₂ | CH₂CH₃ | F | SCF₃ | OCHF₂ |
| CH₂CH₃ | F | OCHF₂ | SCHF₂ | CH₂CH₃ | F | SCF₃ | SCHF₂ |
| CH₂CH₃ | F | OCHF₂ | C₂F₅ | CH₂CH₃ | F | SCF₃ | C₂F₅ |
| CH₂CH₃ | F | OCHF₂ | Cl | CH₂CH₃ | F | SCF₃ | Cl |
| CH₂CH₃ | F | OCHF₂ | SCH₂CH₃ | CH₂CH₃ | F | SCF₃ | SCH₂CH₃ |
| CH₂CH₃ | F | SCHF₂ | CF₃ | CH₂CH₃ | F | Cl | CF₃ |
| CH₂CH₃ | F | SCHF₂ | OCF₃ | CH₂CH₃ | F | Cl | OCF₃ |
| CH₂CH₃ | F | SCHF₂ | SCF₃ | CH₂CH₃ | F | Cl | SCF₃ |
| CH₂CH₃ | F | SCHF₂ | OCHF₂ | CH₂CH₃ | F | Cl | OCHF₂ |
| CH₂CH₃ | F | SCHF₂ | SCHF₂ | CH₂CH₃ | F | Cl | SCHF₂ |
| CH₂CH₃ | F | SCHF₂ | C₂F₅ | CH₂CH₃ | F | Cl | C₂F₅ |
| CH₂CH₃ | F | SCHF₂ | Cl | CH₂CH₃ | F | Cl | Cl |
| CH₂CH₃ | F | SCHF₂ | SCH₂CH₃ | CH₂CH₃ | F | Cl | SCH₂CH₃ |

TABLE 2

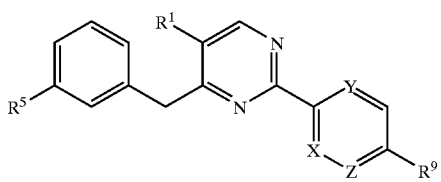

| R¹ | R⁵ | R⁹ | R¹ | R⁵ | R⁹ |
|---|---|---|---|---|---|
| X is N; Y and Z are CH | | | | | |
| CH₂CH₃ | CF₃ | CF₃ | CH₃ | CF₃ | CF₃ |

TABLE 2-continued

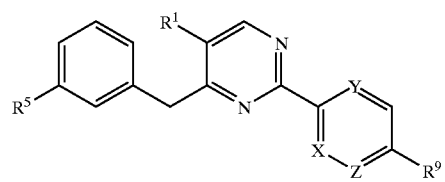

| R¹ | R⁵ | R⁹ | R¹ | R⁵ | R⁹ |
|---|---|---|---|---|---|
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 2-continued

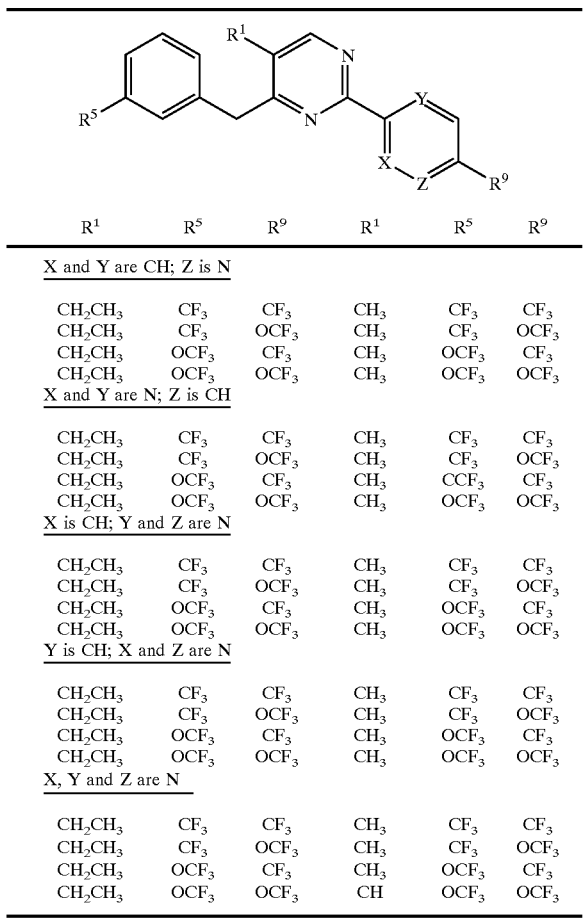

| R¹ | R⁵ | R⁹ | R¹ | R⁵ | R⁹ |
|---|---|---|---|---|---|
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | CCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH | OCF₃ | OCF₃ |

TABLE 3

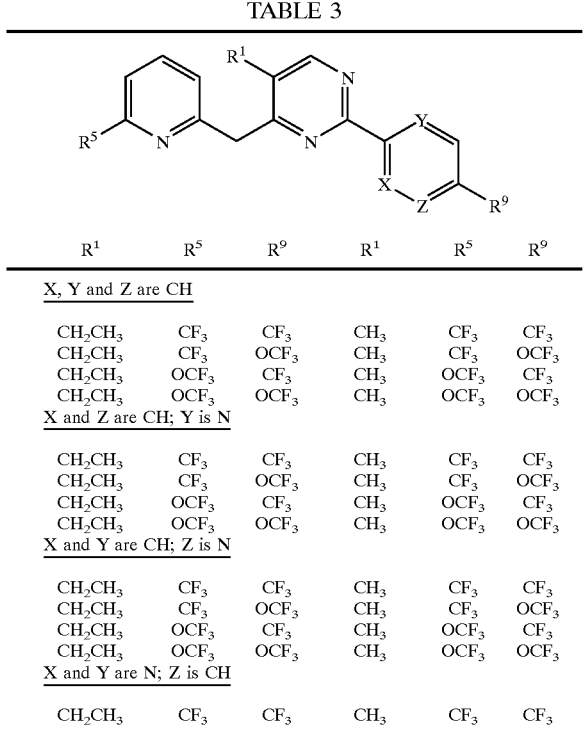

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |

TABLE 3-continued

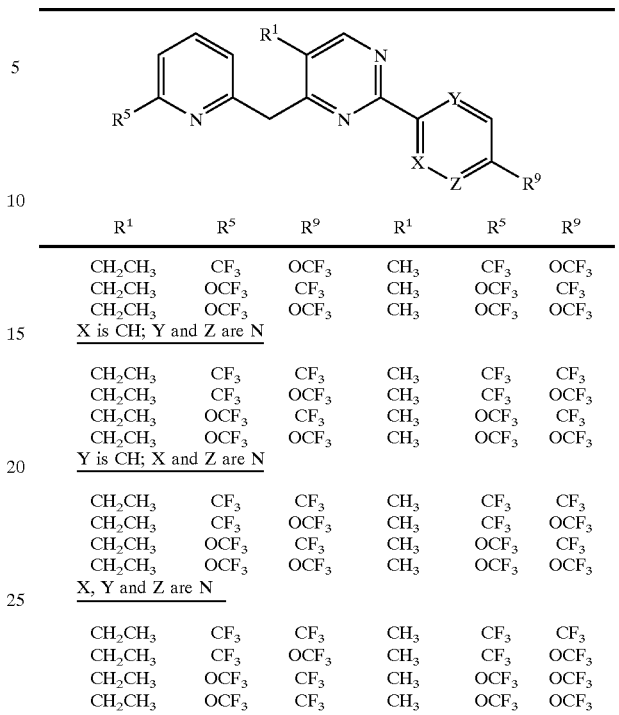

| R¹ | R⁵ | R⁹ | R¹ | R⁵ | R⁹ |
|---|---|---|---|---|---|
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 4

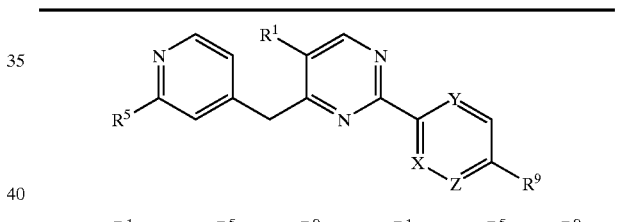

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

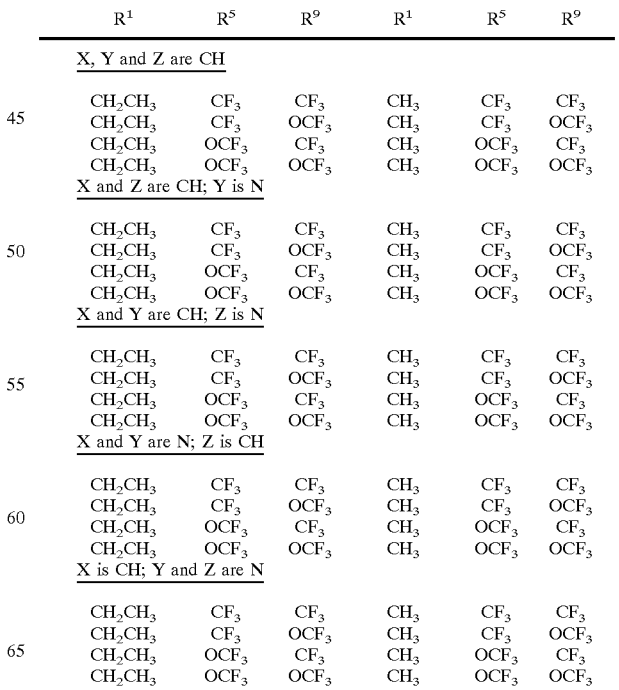

TABLE 4-continued

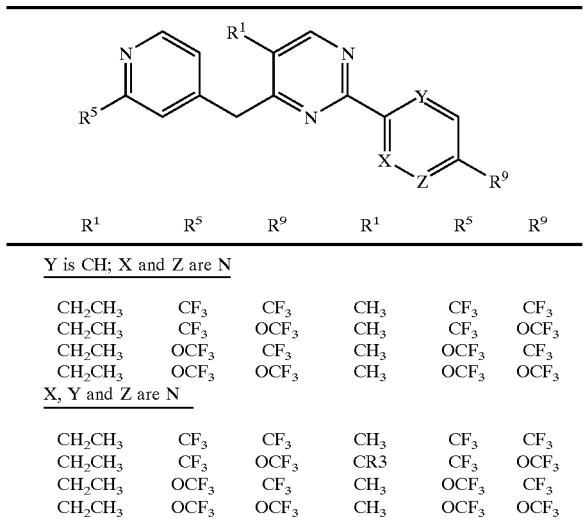

| R¹ | R⁵ | R⁹ | R¹ | R⁵ | R⁹ |
|---|---|---|---|---|---|
| Y is CH; X and Z are N ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N ||||||
| CH₂CH₃ | CF₃ | CF₃ | CH₃ | CF₃ | CF₃ |
| CH₂CH₃ | CF₃ | OCF₃ | CR3 | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 5

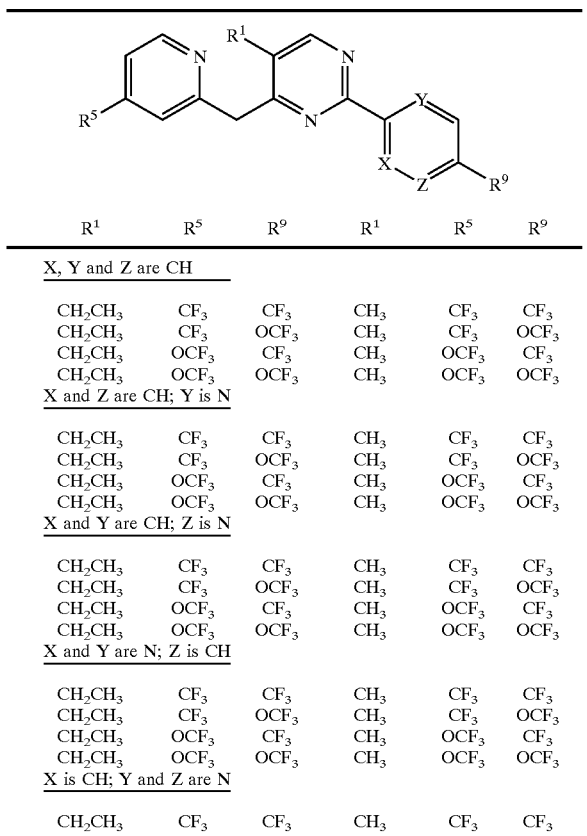

| R¹ | R⁵ | R⁹ | R¹ | R⁵ | R⁹ |
|---|---|---|---|---|---|
| X, Y and Z are CH ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N ||||||
| CH₂CH₃ | CF₃ | CF₃ | CH₃ | CF₃ | CF₃ |

TABLE 5-continued

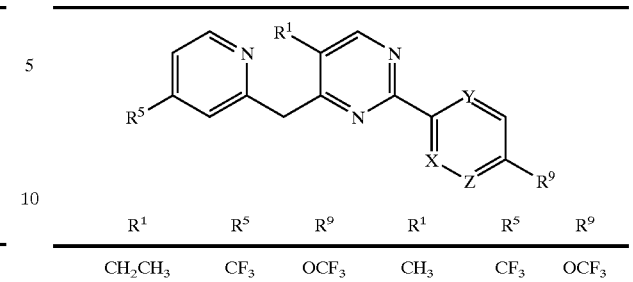

| R¹ | R⁵ | R⁹ | R¹ | R⁵ | R⁹ |
|---|---|---|---|---|---|
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 6

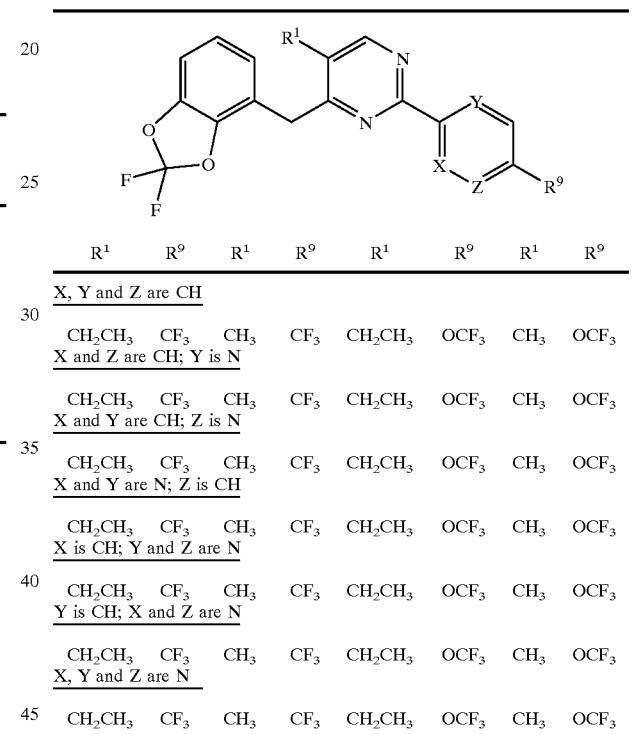

| R¹ | R⁹ | R¹ | R⁹ | R¹ | R⁹ | R¹ | R⁹ |
|---|---|---|---|---|---|---|---|
| X, Y and Z are CH ||||||||
| CH₂CH₃ | CF₃ | CH₃ | CF₃ | CH₂CH₃ | OCF₃ | CH₃ | OCF₃ |
| X and Z are CH; Y is N ||||||||
| CH₂CH₃ | CF₃ | CH₃ | CF₃ | CH₂CH₃ | OCF₃ | CH₃ | OCF₃ |
| X and Y are CH; Z is N ||||||||
| CH₂CH₃ | CF₃ | CH₃ | CF₃ | CH₂CH₃ | OCF₃ | CH₃ | OCF₃ |
| X and Y are N; Z is CH ||||||||
| CH₂CH₃ | CF₃ | CH₃ | CF₃ | CH₂CH₃ | OCF₃ | CH₃ | OCF₃ |
| X is CH; Y and Z are N ||||||||
| CH₂CH₃ | CF₃ | CH₃ | CF₃ | CH₂CH₃ | OCF₃ | CH₃ | OCF₃ |
| Y is CH; X and Z are N ||||||||
| CH₂CH₃ | CF₃ | CH₃ | CF₃ | CH₂CH₃ | OCF₃ | CH₃ | OCF₃ |
| X, Y and Z are N ||||||||
| CH₂CH₃ | CF₃ | CH₃ | CF₃ | CH₂CH₃ | OCF₃ | CH₃ | OCF₃ |

TABLE 7

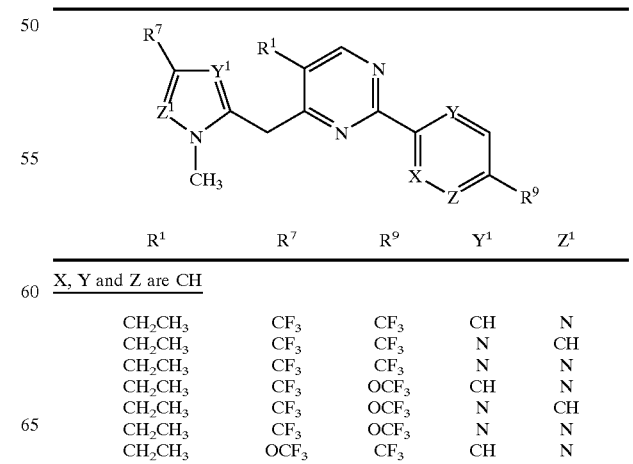

| R¹ | R⁷ | R⁹ | Y¹ | Z¹ |
|---|---|---|---|---|
| X, Y and Z are CH |||||
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |

TABLE 7-continued

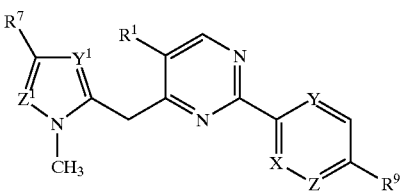

| R¹ | R⁷ | R⁹ | Y¹ | Z¹ |
|---|---|---|---|---|
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |

X is N; Y and Z are CH

| CH₂CH₃ | CF₃ | CF₃ | CH | N |
|---|---|---|---|---|
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |

X and Y are CH; Z is N

| CH₂CH₃ | CF₃ | CF₃ | CH | N |
|---|---|---|---|---|
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |

TABLE 7-continued

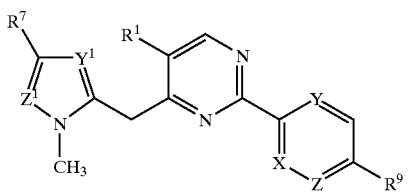

| R¹ | R⁷ | R⁹ | Y¹ | Z¹ |
|---|---|---|---|---|
| CH₃ | OCF₃ | OCF₃ | N | CH |
| CH₃ | OCF₃ | OCF₃ | N | N |

TABLE 8

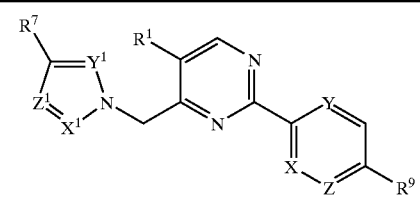

| R¹ | R⁷ | R⁹ | X¹ | Y¹ | Z¹ |
|---|---|---|---|---|---|
| X, Y and Z are CH | | | | | |
| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CH | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CH | N | N |
| CH₃ | OCF₃ | OCF₃ | CH | CH | N |
| CH₃ | OCF₃ | OCF₃ | CH | N | CH |
| CH₃ | OCF₃ | OCF₃ | N | CH | CH |
| CH₃ | OCF₃ | OCF₃ | CH | N | N |
| X is N; Y and Z are CH | | | | | |
| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |

TABLE 8-continued

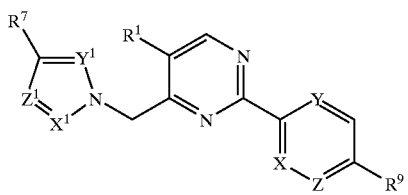

| R¹ | R⁷ | R⁹ | X¹ | Y¹ | Z¹ |
|---|---|---|---|---|---|
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CH | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CH | N | N |
| CH₃ | OCF₃ | OCF₃ | CH | CH | N |
| CH₃ | OCF₃ | OCF₃ | CH | N | CH |
| CH₃ | OCF₃ | OCF₃ | N | CH | CH |
| CH₃ | OCF₃ | OCF₃ | CH | N | N |

X and Y are CH; Z is N

| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CH | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CR | N | N |
| CH₃ | OCF₃ | OCF₃ | CR | CH | N |
| CH₃ | OCF₃ | OCF₃ | CH | N | CH |
| CH₃ | OCF₃ | OCF₃ | N | CH | CH |
| CH₃ | OCF₃ | OCF₃ | CH | N | N |

TABLE 9

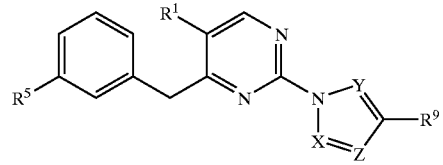

| R¹ | R⁵ | R⁹ | R¹ | R⁵ | R⁹ |
|---|---|---|---|---|---|

X, Y and Z are CH

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X is N; Y and Z are CH

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X and Z are CH; Y is N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X and Y are CH; Z is N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X and Y are N; Z is CH

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X is CH; Y and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

Y is CH; X and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X, Y and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 10

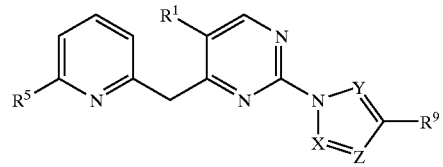

| R¹ | R⁵ | R⁹ | R¹ | R⁵ | R⁹ |
|---|---|---|---|---|---|

X, Y and Z are CH

| CH₂CH₃ | CF₃ | CF₃ | CH₃ | CF₃ | CF₃ |
| CH₂CH₃ | CF₃ | OCF₃ | CH₃ | CF₃ | OCF₃ |

TABLE 10-continued

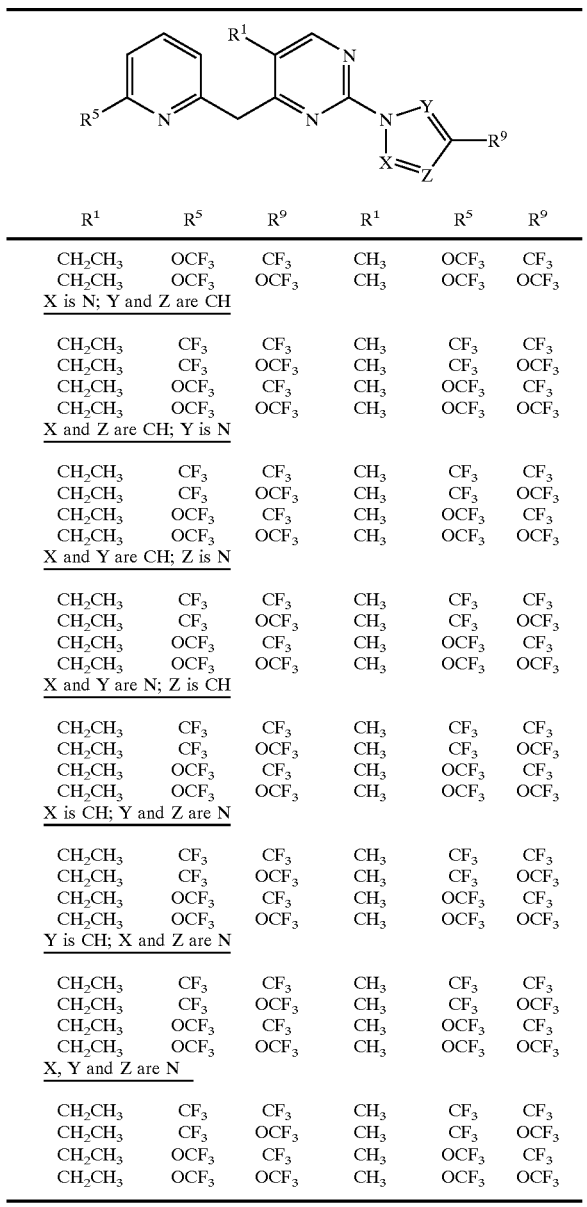

| R¹ | R⁵ | R⁹ | R¹ | R⁵ | R⁹ |
|---|---|---|---|---|---|
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 11

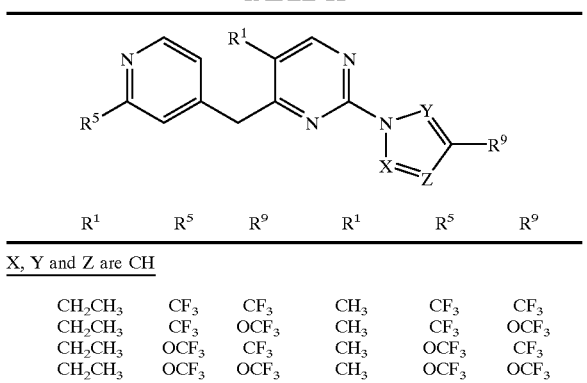

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |

TABLE 11-continued

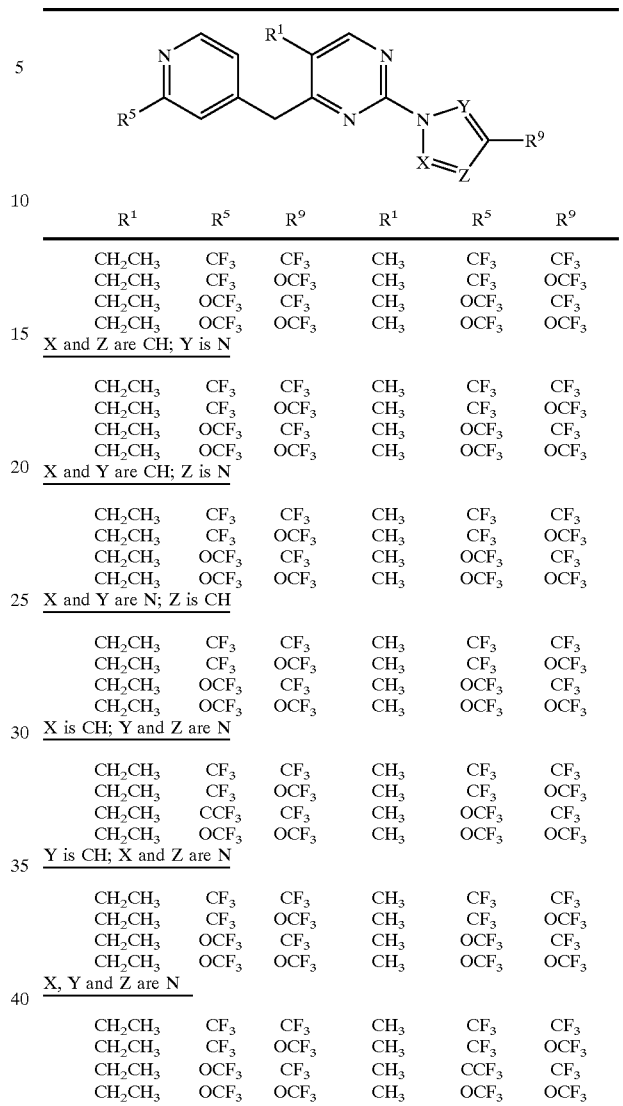

| R¹ | R⁵ | R⁹ | R¹ | R⁵ | R⁹ |
|---|---|---|---|---|---|
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | CCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | CCF₃ | CF₃ |
| CH₂CH₃ | OCF₃ | OCF₃ | CH₃ | OCF₃ | OCF₃ |

TABLE 12

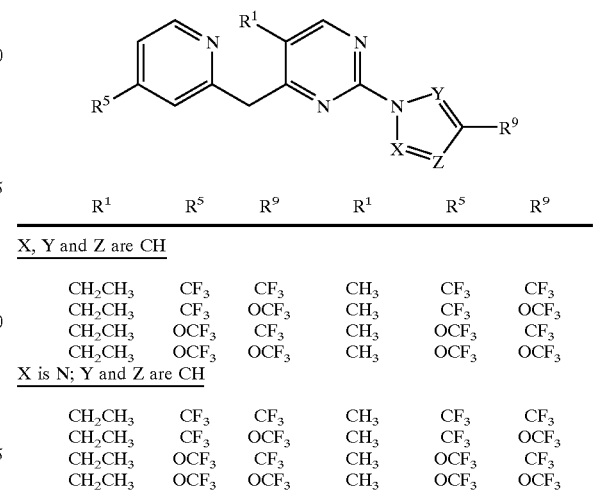

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 12-continued

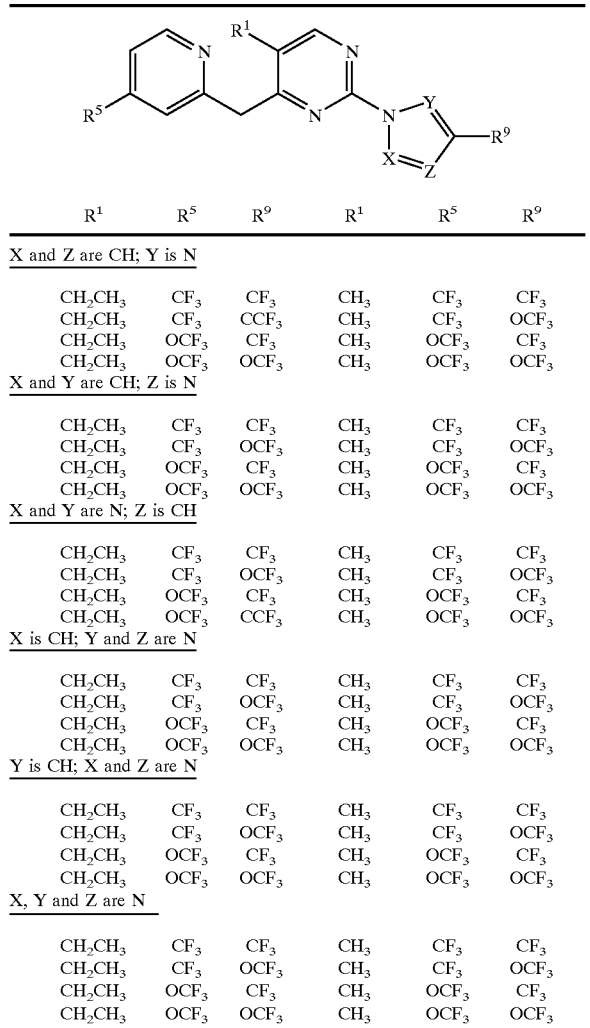

| R¹ | R⁵ | R⁹ | R¹ | R⁵ | R⁹ |
|---|---|---|---|---|---|
| X and Z are CH; Y is N |||||||
| $CH_2CH_3$ | $CF_3$ | $CF_3$ | $CH_3$ | $CF_3$ | $CF_3$ |
| $CH_2CH_3$ | $CF_3$ | $CCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $OCF_3$ | $CH_3$ | $OCF_3$ | $OCF_3$ |
| X and Y are CH; Z is N |||||||
| $CH_2CH_3$ | $CF_3$ | $CF_3$ | $CH_3$ | $CF_3$ | $CF_3$ |
| $CH_2CH_3$ | $CF_3$ | $OCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $OCF_3$ | $CH_3$ | $OCF_3$ | $OCF_3$ |
| X and Y are N; Z is CH |||||||
| $CH_2CH_3$ | $CF_3$ | $CF_3$ | $CH_3$ | $CF_3$ | $CF_3$ |
| $CH_2CH_3$ | $CF_3$ | $OCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $CCF_3$ | $CH_3$ | $OCF_3$ | $OCF_3$ |
| X is CH; Y and Z are N |||||||
| $CH_2CH_3$ | $CF_3$ | $CF_3$ | $CH_3$ | $CF_3$ | $CF_3$ |
| $CH_2CH_3$ | $CF_3$ | $OCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $OCF_3$ | $CH_3$ | $OCF_3$ | $OCF_3$ |
| Y is CH; X and Z are N |||||||
| $CH_2CH_3$ | $CF_3$ | $CF_3$ | $CH_3$ | $CF_3$ | $CF_3$ |
| $CH_2CH_3$ | $CF_3$ | $OCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $OCF_3$ | $CH_3$ | $OCF_3$ | $OCF_3$ |
| X, Y and Z are N |||||||
| $CH_2CH_3$ | $CF_3$ | $CF_3$ | $CH_3$ | $CF_3$ | $CF_3$ |
| $CH_2CH_3$ | $CF_3$ | $OCF_3$ | $CH_3$ | $CF_3$ | $OCF_3$ |
| $CH_2CH_3$ | $OCF_3$ | $CF_3$ | $CH_3$ | $OCF_3$ | $CF_3$ |
| $CH_2CH_3$ | $OCF_3$ | $OCF_3$ | $CH_3$ | $OCF_3$ | $OCF_3$ |

TABLE 13

| R¹ | R⁹ | R¹ | R⁹ | R¹ | R⁹ | R¹ | R⁹ |
|---|---|---|---|---|---|---|---|
| X, Y and Z are CH |||||||||
| $CH_2CH_3$ | $CF_3$ | $CH_3$ | $CF_3$ | $CH_2CH_3$ | $OCF_3$ | $CH_3$ | $OCF_3$ |
| X is N; Y and Z are CH |||||||||
| $CH_2CH_3$ | $CF_3$ | $CH_3$ | $CF_3$ | $CH_2CH_3$ | $OCF_3$ | $CH_3$ | $OCF_3$ |
| X and Z are CH; Y is N |||||||||
| $CH_2CH_3$ | $CF_3$ | $CH_3$ | $CF_3$ | $CH_2CH_3$ | $OCF_3$ | $CH_3$ | $OCF_3$ |
| X and Y are CH; Z is N |||||||||
| $CH_2CH_3$ | $CF_3$ | $CH_3$ | $CF_3$ | $CH_2CH_3$ | $OCF_3$ | $CH_3$ | $OCF_3$ |
| X and Y are N; Z is CH |||||||||
| $CH_2CH_3$ | $CF_3$ | $CH_3$ | $CF_3$ | $CH_2CH_3$ | $OCF_3$ | $CH_3$ | $OCF_3$ |

TABLE 13-continued

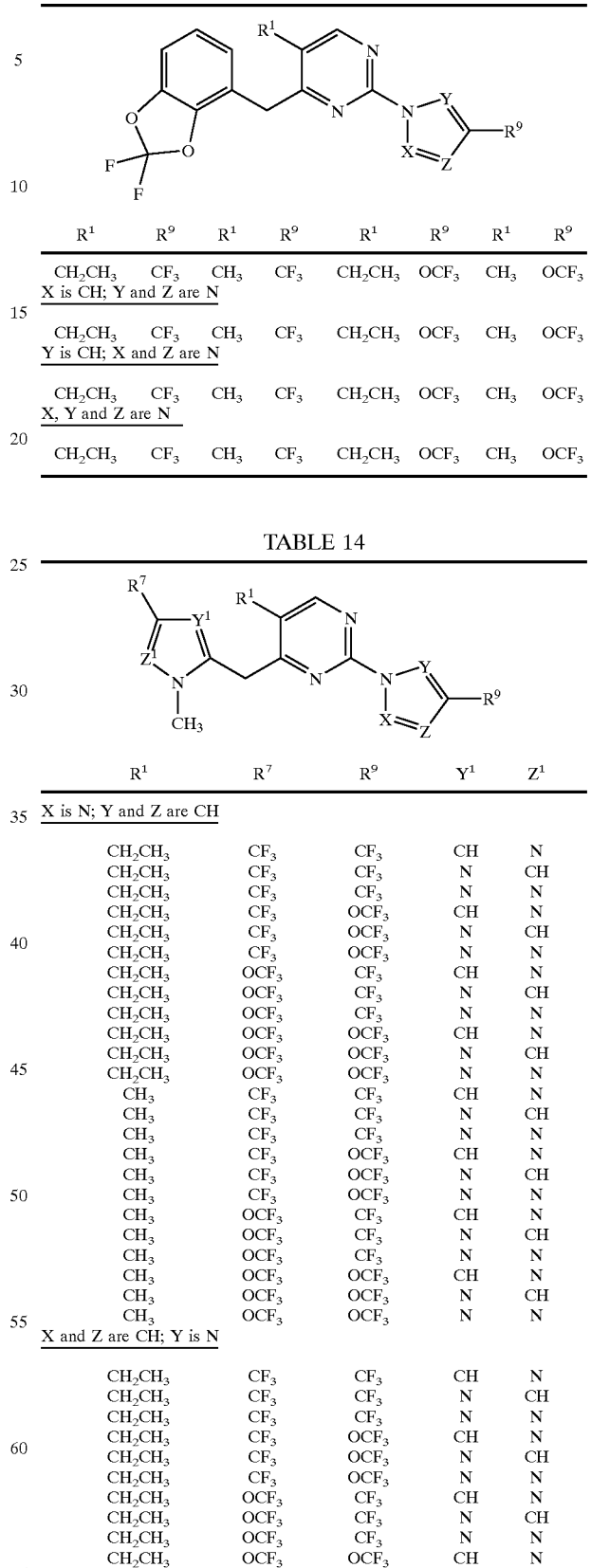

| R¹ | R⁹ | R¹ | R⁹ | R¹ | R⁹ | R¹ | R⁹ |
|---|---|---|---|---|---|---|---|
| X is CH; Y and Z are N |||||||||
| $CH_2CH_3$ | $CF_3$ | $CH_3$ | $CF_3$ | $CH_2CH_3$ | $OCF_3$ | $CH_3$ | $OCF_3$ |
| Y is CH; X and Z are N |||||||||
| $CH_2CH_3$ | $CF_3$ | $CH_3$ | $CF_3$ | $CH_2CH_3$ | $OCF_3$ | $CH_3$ | $OCF_3$ |
| X, Y and Z are N |||||||||
| $CH_2CH_3$ | $CF_3$ | $CH_3$ | $CF_3$ | $CH_2CH_3$ | $OCF_3$ | $CH_3$ | $OCF_3$ |

TABLE 14

| R¹ | R⁷ | R⁹ | Y¹ | Z¹ |
|---|---|---|---|---|
| X is N; Y and Z are CH |||||
| $CH_2CH_3$ | $CF_3$ | $CF_3$ | CH | N |
| $CH_2CH_3$ | $CF_3$ | $CF_3$ | N | CH |
| $CH_2CH_3$ | $CF_3$ | $CF_3$ | N | N |
| $CH_2CH_3$ | $CF_3$ | $OCF_3$ | CH | N |
| $CH_2CH_3$ | $CF_3$ | $OCF_3$ | N | CH |
| $CH_2CH_3$ | $CF_3$ | $OCF_3$ | N | N |
| $CH_2CH_3$ | $OCF_3$ | $CF_3$ | CH | N |
| $CH_2CH_3$ | $OCF_3$ | $CF_3$ | N | CH |
| $CH_2CH_3$ | $OCF_3$ | $CF_3$ | N | N |
| $CH_2CH_3$ | $OCF_3$ | $OCF_3$ | CH | N |
| $CH_2CH_3$ | $OCF_3$ | $OCF_3$ | N | CH |
| $CH_2CH_3$ | $OCF_3$ | $OCF_3$ | N | N |
| $CH_3$ | $CF_3$ | $CF_3$ | CH | N |
| $CH_3$ | $CF_3$ | $CF_3$ | N | CH |
| $CH_3$ | $CF_3$ | $CF_3$ | N | N |
| $CH_3$ | $CF_3$ | $OCF_3$ | CH | N |
| $CH_3$ | $CF_3$ | $OCF_3$ | N | CH |
| $CH_3$ | $CF_3$ | $OCF_3$ | N | N |
| $CH_3$ | $OCF_3$ | $CF_3$ | CH | N |
| $CH_3$ | $OCF_3$ | $CF_3$ | N | CH |
| $CH_3$ | $OCF_3$ | $CF_3$ | N | N |
| $CH_3$ | $OCF_3$ | $OCF_3$ | CH | N |
| $CH_3$ | $OCF_3$ | $OCF_3$ | N | CH |
| $CH_3$ | $OCF_3$ | $OCF_3$ | N | N |
| X and Z are CH; Y is N |||||
| $CH_2CH_3$ | $CF_3$ | $CF_3$ | CH | N |
| $CH_2CH_3$ | $CF_3$ | $CF_3$ | N | CH |
| $CH_2CH_3$ | $CF_3$ | $CF_3$ | N | N |
| $CH_2CH_3$ | $CF_3$ | $OCF_3$ | CH | N |
| $CH_2CH_3$ | $CF_3$ | $OCF_3$ | N | CH |
| $CH_2CH_3$ | $CF_3$ | $OCF_3$ | N | N |
| $CH_2CH_3$ | $OCF_3$ | $CF_3$ | CH | N |
| $CH_2CH_3$ | $OCF_3$ | $CF_3$ | N | CH |
| $CH_2CH_3$ | $OCF_3$ | $CF_3$ | N | N |
| $CH_2CH_3$ | $OCF_3$ | $OCF_3$ | CH | N |
| $CH_2CH_3$ | $OCF_3$ | $OCF_3$ | N | CH |
| $CH_2CH_3$ | $OCF_3$ | $OCF_3$ | N | N |

TABLE 14-continued

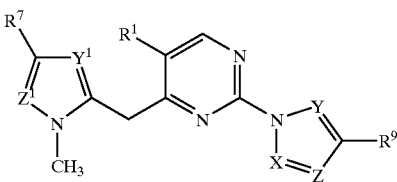

| R¹ | R⁷ | R⁹ | Y¹ | Z¹ |
|---|---|---|---|---|
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |
| X and Y are CH; Z is N | | | | |
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | CCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |
| X is CH; Y and Z are N | | | | |
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |

TABLE 15

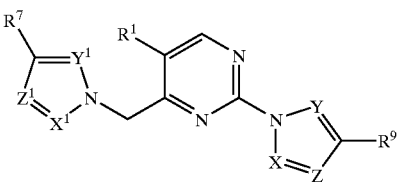

| R¹ | R⁷ | R⁹ | X¹ | Y¹ | Z¹ |
|---|---|---|---|---|---|
| X is N; Y and Z are CH | | | | | |
| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CH | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CH | N | N |
| CH₃ | OCF₃ | OCF₃ | CH | CH | N |
| CH₃ | OCF₃ | OCF₃ | CH | N | CH |
| CH₃ | OCF₃ | OCF₃ | N | CH | CH |
| CH₃ | OCF₃ | OCF₃ | CH | N | N |
| X and Z are CH; Y is N | | | | | |
| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CH | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CH | N | N |
| CH₃ | OCF₃ | OCF₃ | CH | CH | N |
| CH₃ | OCF₃ | OCF₃ | CH | N | CH |

TABLE 15-continued

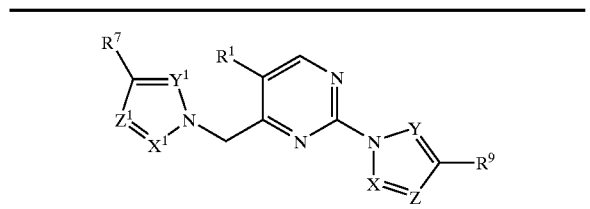

| R¹ | R⁷ | R⁹ | X¹ | Y¹ | Z¹ |
|---|---|---|---|---|---|
| CH₃ | OCF₃ | OCF₃ | CH | N | N |

X and Y are CH; Z is N

| R¹ | R⁷ | R⁹ | X¹ | Y¹ | Z¹ |
|---|---|---|---|---|---|
| CH₂CH₃ | CF₃ | CF₃ | CH | CH | N |
| CH₂CH₃ | CF₃ | CF₃ | CH | N | CH |
| CH₂CH₃ | CF₃ | CF₃ | N | CH | CH |
| CH₂CH₃ | CF₃ | CF₃ | CH | N | N |
| CH₂CH₃ | CF₃ | OCF₃ | CH | CH | N |
| CH₂CH₃ | CF₃ | OCF₃ | CH | N | CH |
| CH₂CH₃ | CF₃ | OCF₃ | N | CH | CH |
| CH₂CH₃ | CF₃ | OCF₃ | CH | N | N |
| CH₂CH₃ | OCF₃ | CF₃ | CH | CH | N |
| CH₂CH₃ | OCF₃ | CF₃ | CH | N | CH |
| CH₂CH₃ | OCF₃ | CF₃ | N | CH | CH |
| CH₂CH₃ | OCF₃ | CF₃ | CH | N | N |
| CH₂CH₃ | OCF₃ | OCF₃ | CH | CH | N |
| CH₂CH₃ | OCF₃ | OCF₃ | CH | N | CH |
| CH₂CH₃ | OCF₃ | OCF₃ | N | CH | CH |
| CH₂CH₃ | OCF₃ | OCF₃ | CH | N | N |
| CH₃ | CF₃ | CF₃ | CH | CH | N |

TABLE 15-continued

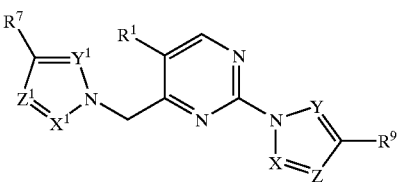

| R¹ | R⁷ | R⁹ | X¹ | Y¹ | Z¹ |
|---|---|---|---|---|---|
| CH₃ | CF₃ | CF₃ | CH | N | CH |
| CH₃ | CF₃ | CF₃ | N | CH | CH |
| CH₃ | CF₃ | CF₃ | CH | N | N |
| CH₃ | CF₃ | OCF₃ | CH | CH | N |
| CH₃ | CF₃ | OCF₃ | CH | N | CH |
| CH₃ | CF₃ | OCF₃ | N | CH | CH |
| CH₃ | CF₃ | OCF₃ | CR | N | N |
| CH₃ | OCF₃ | CF₃ | CH | CH | N |
| CH₃ | OCF₃ | CF₃ | CH | N | CH |
| CH₃ | OCF₃ | CF₃ | N | CH | CH |
| CH₃ | OCF₃ | CF₃ | CH | N | N |
| CH₃ | OCF₃ | OCF₃ | CH | CH | N |
| CH₃ | OCF₃ | OCF₃ | CH | N | CH |
| CH₃ | OCF₃ | OCF₃ | N | CH | CH |
| CH | OCF₃ | OCF₃ | CH | N | N |

TABLE 16

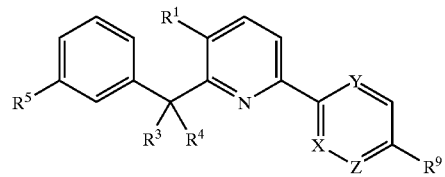

R³ is H; X, Y and Z are CH

| R¹ | R⁴ | R⁵ | R⁹ | R¹ | R⁴ | R⁵ | R⁹ |
|---|---|---|---|---|---|---|---|
| CH₂CH₃ | H | CF₃ | CF₃ | CH₂CH₃ | H | OCF₃ | CF₃ |
| CH₂CH₃ | H | CF₃ | OCF₃ | CH₂CH₃ | H | OCF₃ | OCF₃ |
| CH₂CH₃ | H | CF₃ | SCF₃ | CH₂CH₃ | H | OCF₃ | SCF₃ |
| CH₂CH₃ | H | CF₃ | OCHF₂ | CH₂CH₃ | H | OCF₃ | OCHF₂ |
| CH₂CH₃ | H | CF₃ | SCHF₂ | CH₂CH₃ | H | OCF₃ | SCHF₂ |
| CH₂CH₃ | H | CF₃ | C₂F₅ | CH₂CH₃ | H | OCF₃ | C₂F₅ |
| CH₂CH₃ | H | CF₃ | Cl | CH₂CH₃ | H | OCF₃ | Cl |
| CH₂CH₃ | H | CF₃ | SCH₂CH₃ | CH₂CH₃ | H | OCF₃ | SCH₂CH₃ |
| CH₂CH₃ | H | OCHF₂ | CF₃ | CH₂CH₃ | H | SCF₃ | CF₃ |
| CH₂CH₃ | H | OCHF₂ | OCF₃ | CH₂CH₃ | H | SCF₃ | OCF₃ |
| CH₂CH₃ | H | OCHF₂ | SCF₃ | CH₂CH₃ | H | SCF₃ | SCF₃ |
| CH₂CH₃ | H | OCHF₂ | OCHF₂ | CH₂CH₃ | H | SCF₃ | OCHF₂ |
| CH₂CH₃ | H | OCHF₂ | SCHF₂ | CH₂CH₃ | H | SCF₃ | SCHF₂ |
| CH₂CH₃ | H | OCHF₂ | C₂F₅ | CH2CH₃ | H | SCF₃ | C₂F₅ |
| CH₂CH₃ | H | OCHF₂ | Cl | CH₂CH₃ | H | SCF₃ | Cl |
| CH₂CH₃ | H | OCHF₂ | SCH₂CH₃ | CH₂CH₃ | H | SCF₃ | SCH₂CH₃ |
| CH₂CH₃ | H | SCHF₂ | CF₃ | CH₂CH₃ | H | Cl | CF₃ |
| CH₂CH₃ | H | SCHF₂ | OCF₃ | CH₂CH₃ | H | Cl | OCF₃ |

TABLE 16-continued

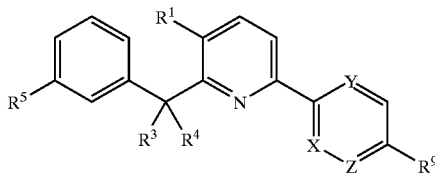

R³ is H; X, Y and Z are CH

| R¹ | R⁴ | R⁵ | R⁹ | R¹ | R⁴ | R⁵ | R⁹ |
|---|---|---|---|---|---|---|---|
| CH₂CH₃ | H | SCHF₂ | SCF₃ | CH₂CH₃ | H | Cl | SCF₃ |
| CH₂CH₃ | H | SCHF₂ | OCHF₂ | CH₂CH₃ | H | Cl | OCHF₂ |
| CH₂CH₃ | H | SCHF₂ | SCHF₂ | CH₂CH₃ | H | Cl | SCHF₂ |
| CH₂CH₃ | H | SCHF₂ | C₂F₅ | CH₂CH₃ | H | Cl | C₂F₅ |
| CH₂CH₃ | H | SCHF₂ | Cl | CH₂CH₃ | H | Cl | Cl |
| CH₂CH₃ | H | SCHF₂ | SCH₂CH₃ | CH₂CH₃ | H | Cl | SCH₂CH₃ |
| CH₂CH₃ | CH₃ | CF₃ | CF₃ | CH₂CH₃ | CH₃ | OCF₃ | CF₃ |
| CH₂CH₃ | CH₃ | CF₃ | OCF₃ | CH₂CH₃ | CH₃ | OCF₃ | OCF₃ |
| CH₂CH₃ | CH₃ | CF₃ | SCF₃ | CH₂CH₃ | CH₃ | OCF₃ | SCF₃ |
| CH₂CH₃ | CH₃ | CF₃ | OCHF₂ | CH₂CH₃ | CH₃ | OCF₃ | OCHF₂ |
| CH₂CH₃ | CH₃ | CF₃ | SCHF₂ | CH₂CH₃ | CH₃ | OCF₃ | SCHF₂ |
| CH₂CH₃ | CH₃ | CF₃ | C₂F₅ | CH₂CH₃ | CH₃ | OCF₃ | C₂F₅ |
| CH₂CH₃ | CH₃ | CF₃ | Cl | CH₂CH₃ | CH₃ | OCF₃ | Cl |
| CH₂CH₃ | CH₃ | CF₃ | SCH₂CH₃ | CH₂CH₃ | CH₃ | OCF₃ | SCH₂CH₃ |
| CH₂CH₃ | CH₃ | OCHF₂ | CF₃ | CH₂CH₃ | CH₃ | SCF₃ | CF₃ |
| CH₂CH₃ | CH₃ | OCHF₂ | OCF₃ | CH₂CH₃ | CH₃ | SCF₃ | OCF₃ |
| CH₂CH₃ | CH₃ | OCHF₂ | SCF₃ | CH₂CH₃ | CH₃ | SCF₃ | SCF₃ |
| CH₂CH₃ | CH₃ | OCHF₂ | OCHF₂ | CH₂CH₃ | CH₃ | SCF₃ | OCHF₂ |
| CH₂CH₃ | CH₃ | OCHF₂ | SCHF₂ | CH₂CH₃ | CH₃ | SCF₃ | SCHF₂ |
| CH₂CH₃ | CH₃ | OCHF₂ | C₂F₅ | CH₂CH₃ | CH₃ | SCF₃ | C₂F₅ |
| CH₂CH₃ | CH₃ | OCHF₂ | Cl | CH₂CH₃ | CH₃ | SCF₃ | Cl |
| CH₂CH₃ | CH₃ | OCHF₂ | SCH₂CH₃ | CH₂CH₃ | CH₃ | SCF₃ | SCH₂CH₃ |
| CH₂CH₃ | CH₃ | SCHF₂ | CF₃ | CH₂CH₃ | CH₃ | Cl | CF₃ |
| CH₂CH₃ | CH₃ | SCHF₂ | OCF₃ | CH₂CH₃ | CH₃ | Cl | OCF₃ |
| CH₂CH₃ | CH₃ | SCHF₂ | SCF₃ | CH₂CH₃ | CH₃ | Cl | SCF₃ |
| CH₂CH₃ | CH₃ | SCHF₂ | OCHF₂ | CH₂CH₃ | CH₃ | Cl | OCHF₂ |
| CH₂CH₃ | CH₃ | SCHF₂ | SCHF₂ | CH₂CH₃ | CH₃ | Cl | SCHF₂ |
| CH₂CH₃ | CH₃ | SCHF₂ | C₂F₅ | CH₂CH₃ | CH₃ | Cl | C₂F₅ |
| CH₂CH₃ | CH₃ | SCHF₂ | Cl | CH₂CH₃ | CH₃ | Cl | Cl |
| CH₂CH₃ | CH₃ | SCHF₂ | SCH₂CH₃ | CH₂CH₃ | CH₃ | Cl | SCH₂CH₃ |
| CH₂CH₃ | F | CF₃ | CF₃ | CH₂CH₃ | F | OCF₃ | CF₃ |
| CH₂CH₃ | F | CF₃ | OCF₃ | CH₂CH₃ | F | OCF₃ | OCF₃ |
| CH₂CH₃ | F | CF₃ | SCF₃ | CH₂CH₃ | F | OCF₃ | SCF₃ |
| CH₂CH₃ | F | CF₃ | OCHF₂ | CH₂CH₃ | F | OCF₃ | OCHF₂ |
| CH₂CH₃ | F | CF₃ | SCHF₂ | CH₂CH₃ | F | OCF₃ | SCHF₂ |
| CH₂CH₃ | F | CF₃ | C₂F₅ | CH₂CH₃ | F | OCF₃ | C₂F₅ |
| CH₂CH₃ | F | CF₃ | Cl | CH₂CH₃ | F | OCF₃ | Cl |
| CH₂CH₃ | F | CF₃ | SCH₂CH₃ | CH₂CH₃ | F | OCF₃ | SCH₂CH₃ |
| CH₂CH₃ | F | OCHF₂ | CF₃ | CH₂CH₃ | F | SCF₃ | CF₃ |
| CH₂CH₃ | F | OCHF₂ | OCF₃ | CH₂CH₃ | F | SCF₃ | OCF₃ |
| CH₂CH₃ | F | OCHF₂ | SCF₃ | CH₂CH₃ | F | SCF₃ | SCF₃ |
| CH₂CH₃ | F | OCHF₂ | OCHF₂ | CH₂CH₃ | F | SCF₃ | OCHF₂ |
| CH₂CH₃ | F | OCHF₂ | SCHF₂ | CH₂CH₃ | F | SCF₃ | SCHF₂ |
| CH₂CH₃ | F | OCHF₂ | C₂F₅ | CH₂CH₃ | F | SCF₃ | C₂F₅ |
| CH₂CH₃ | F | OCHF₂ | Cl | CH₂CH₃ | F | SCF₃ | Cl |
| CH₂CH₃ | F | OCHF₂ | SCH₂CH₃ | CH₂CH₃ | F | SCF₃ | SCH₂CH₃ |
| CH₂CH₃ | F | SCHF₂ | CF₃ | CH₂CH₃ | F | Cl | CF₃ |
| CH₂CH₃ | F | SCHF₂ | OCF₃ | CH₂CH₃ | F | Cl | OCF₃ |
| CH₂CH₃ | F | SCHF₂ | SCF₃ | CH₂CH₃ | F | Cl | SCF₃ |
| CH₂CH₃ | F | SCHF₂ | OCHF₂ | CH₂CH₃ | F | Cl | OCHF₂ |
| CH₂CH₃ | F | SCHF₂ | SCHF₂ | CH₂CH₃ | F | Cl | SCHF₂ |
| CH₂CH₃ | F | SCHF₂ | C₂F₅ | CH₂CH₃ | F | Cl | C₂F₅ |
| CH₂CH₃ | F | SCHF₂ | Cl | CH₂CH₃ | F | Cl | Cl |
| CH₂CH₃ | F | SCHF₂ | SCH₂CH₃ | CH₂CH₃ | F | Cl | SCH₂CH₃ |
| CH₂CH₃ | Cl | CF₃ | CF₃ | CH₂CH₃ | Cl | OCF₃ | CF₃ |
| CH₂CH₃ | Cl | CF₃ | OCF₃ | CH₂CH₃ | Cl | OCF₃ | OCF₃ |
| CH₂CH₃ | Cl | CF₃ | SCF₃ | CH₂CH₃ | Cl | OCF₃ | SCF₃ |
| CH₂CH₃ | Cl | CF₃ | ClCHF2 | CH₂CH₃ | Cl | OCF₃ | OCHF₂ |
| CH₂CH₃ | Cl | CF₃ | SCHF₂ | CH₂CH₃ | Cl | OCF₃ | SCHF₂ |
| CH₂CH₃ | Cl | CF₃ | C₂F₅ | CH₂CH₃ | Cl | OCF₃ | C₂F₅ |
| CH₂CH₃ | Cl | CF₃ | Cl | CH₂CH₃ | Cl | OCF₃ | Cl |
| CH₂CH₃ | Cl | CF₃ | SCH₂CH₃ | CH₂CH₃ | Cl | OCF₃ | SCH₂CH₃ |
| CH₂CH₃ | Cl | OCHF₂ | CF₃ | CH₂CH₃ | Cl | SCF₃ | CF₃ |
| CH₂CH₃ | Cl | OCHF₂ | OCF₃ | CH₂CH₃ | Cl | SCF₃ | OCF₃ |
| CH₂CH₃ | Cl | OCHF₂ | SCF₃ | CH₂CH₃ | Cl | SCF₃ | SCF₃ |

TABLE 16-continued

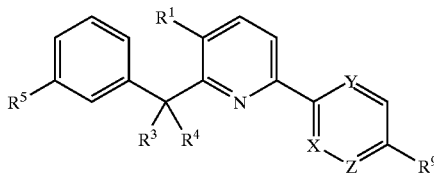

R³ is H; X, Y and Z are CH

| R¹ | R⁴ | R⁵ | R⁹ | R¹ | R⁴ | R⁵ | R⁹ |
|---|---|---|---|---|---|---|---|
| CH₂CH₃ | Cl | OCHF₂ | OCHF₂ | CH₂CH₃ | Cl | SCF₃ | OCHF₂ |
| CH₂CH₃ | Cl | OCHF₂ | SCHF₂ | CH₂CH₃ | Cl | SCF₃ | SCHF₂ |
| CH₂CH₃ | Cl | OCHF₂ | C₂F₅ | CH₂CH₃ | Cl | SCF₃ | C₂F₅ |
| CH₂CH₃ | Cl | OCHF₂ | Cl | CH₂CH₃ | Cl | SCF₃ | Cl |
| CH₂CH₃ | Cl | OCHF₂ | SCH₂CH₃ | CH₂CH₃ | Cl | SCF₃ | SCH₂CH₃ |
| CH₂CH₃ | Cl | SCHF₂ | CF₃ | CH₂CH₃ | Cl | Cl | CF₃ |
| CH₂CH₃ | Cl | SCHF₂ | OCF₃ | CH₂CH₃ | Cl | Cl | OCF₃ |
| CH₂CH₃ | Cl | SCHF₂ | SCF₃ | CH₂CH₃ | Cl | Cl | SCF₃ |
| CH₂CH₃ | Cl | SCHF₂ | OCHF₂ | CH₂CH₃ | Cl | Cl | OCHF₂ |
| CH₂CH₃ | Cl | SCHF₂ | SCHF₂ | CH₂CH₃ | Cl | Cl | SCHF₂ |
| CH₂CH₃ | Cl | SCHF₂ | C₂F₅ | CH₂CH₃ | Cl | Cl | C₂F₅ |
| CH₂CH₃ | Cl | SCHF₂ | Cl | CH₂CH₃ | Cl | Cl | Cl |
| CH₂CH₃ | Cl | SCHF₂ | SCH₂CH₃ | CH₂CH₃ | Cl | Cl | SCH₂CH₃ |
| CH₃ | H | CF₃ | CF₃ | CH₃ | H | OCF₃ | CF₃ |
| CH₃ | H | CF₃ | OCF₃ | CH₃ | H | OCF₃ | OCF₃ |
| CH₃ | H | CF₃ | SCF₃ | CH₃ | H | OCF₃ | SCF₃ |
| CH₃ | H | CF₃ | OCHF₂ | CH₃ | H | OCF₃ | OCHF₂ |
| CH₃ | H | CF₃ | SCHF₂ | CH₃ | H | OCF₃ | SCHF₂ |
| CH₃ | H | CF₃ | C₂F₅ | CH₃ | H | OCF₃ | C₂F₅ |
| CH₃ | H | CF₃ | Cl | CH₃ | H | OCF₃ | Cl |
| CH₃ | H | CF₃ | SCH₂CH₃ | CH₃ | H | OCF₃ | SCH₂CH₃ |
| CH₃ | H | OCHF₂ | CF₃ | CH₃ | H | SCF₃ | CF₃ |
| CH₃ | H | OCHF₂ | OCF₃ | CH₃ | H | SCF₃ | OCF₃ |
| CH₃ | H | OCHF₂ | SCF₃ | CH₃ | H | SCF₃ | SCF₃ |
| CH₃ | H | OCHF₂ | OCHF₂ | CH₃ | H | SCF₃ | OCHF₂ |
| CH₃ | H | OCHF₂ | SCHF₂ | CH₃ | H | SCF₃ | SCHF₂ |
| CH₃ | H | OCHF₂ | C₂F₅ | CH₃ | H | SCF₃ | C₂F₅ |
| CH₃ | H | OCHF₂ | Cl | CH₃ | H | SCF₃ | Cl |
| CH₃ | H | OCHF₂ | SCH₂CH₃ | CH₃ | H | SCF₃ | SCH₂CH₃ |
| CH₃ | H | SCHF₂ | CF₃ | CH₃ | H | Cl | CF₃ |
| CH₃ | H | SCHF₂ | OCF₃ | CH₃ | H | Cl | OCF₃ |
| CH₃ | H | SCHF₂ | SCF₃ | CH₃ | H | Cl | SCF₃ |
| CH₃ | H | SCHF₂ | OCHF₂ | CH₃ | H | Cl | OCHF₂ |
| CH₃ | H | SCHF₂ | SCHF₂ | CH₃ | H | Cl | SCHF₂ |
| CH₃ | H | SCHF₂ | C₂F₅ | CH₃ | H | Cl | C₂F₅ |
| CH₃ | H | SCHF₂ | Cl | CH₃ | H | Cl | Cl |
| CH₃ | H | SCHF₂ | SCH₂CH₃ | CH₃ | H | Cl | SCH₂CH₃ |
| CH₃ | CH₃ | CF₃ | CF₃ | CH₃ | CH₃ | OCF₃ | CF₃ |
| CH₃ | CH₃ | CF₃ | OCF₃ | CH₃ | CH₃ | OCF₃ | OCF₃ |
| CH₃ | CH₃ | CF₃ | SCF₃ | CH₃ | CH₃ | OCF₃ | SCF₃ |
| CH₃ | CH₃ | CF₃ | OCHF₂ | CH₃ | CH₃ | OCF₃ | OCHF₂ |
| CH₃ | CH₃ | CF₃ | SCHF₂ | CH₃ | CH₃ | OCF₃ | SCHF₂ |
| CH₃ | CH₃ | CF₃ | C₂F₅ | CH₃ | CH₃ | OCF₃ | C₂F₅ |
| CH₃ | CH₃ | CF₃ | Cl | CH₃ | CH₃ | OCF₃ | Cl |
| CH₃ | CH₃ | CF₃ | SCH₂CH₃ | CH₃ | CH₃ | OCF₃ | SCH₂CH₃ |
| CH₃ | CH₃ | OCHF₂ | CF₃ | CH₃ | CH₃ | SCF₃ | CF₃ |
| CH₃ | CH₃ | OCHF₂ | OCF₃ | CH₃ | CH₃ | SCF₃ | OCF₃ |
| CH₃ | CH₃ | OCHF₂ | SCF₃ | CH₃ | CH₃ | SCF₃ | SCF₃ |
| CH₃ | CH₃ | OCHF₂ | OCHF₂ | CH₃ | CH₃ | SCF₃ | OCHF₂ |
| CH₃ | CH₃ | OCHF₂ | SCHF₂ | CH₃ | CH₃ | SCF₃ | SCHF₂ |
| CH₃ | CH₃ | OCHF₂ | C₂F₅ | CH₃ | CH₃ | SCF₃ | C₂F₅ |
| CH₃ | CH₃ | OCHF₂ | Cl | CH₃ | CH₃ | SCF₃ | Cl |
| CH₃ | CH₃ | OCHF₂ | SCH₂CH₃ | CH₃ | CH₃ | SCF₃ | SCH₂CH₃ |
| CH₃ | CH₃ | SCHF₂ | CF₃ | CH₃ | CH₃ | Cl | CF₃ |
| CH₃ | CH₃ | SCHF₂ | OCF₃ | CH₃ | CH₃ | Cl | OCF₃ |
| CH₃ | CH₃ | SCHF₂ | SCF₃ | CH₃ | CH₃ | Cl | SCF₃ |
| CH₃ | CH₃ | SCHF₂ | OCHF₂ | CH₃ | CH₃ | Cl | OCHF₂ |
| CH₃ | CH₃ | SCHF₂ | SCHF₂ | CH₃ | CH₃ | Cl | SCHF₂ |
| CH₃ | CH₃ | SCHF₂ | C₂F₅ | CH₃ | CH₃ | Cl | C₂F₅ |
| CH₃ | CH₃ | SCHF₂ | Cl | CH₃ | CH₃ | Cl | Cl |
| CH₃ | CH₃ | SCHF₂ | SCH₂CH₃ | CH₃ | CH₃ | Cl | SCH₂CH₃ |
| CH₃ | F | CF₃ | CF₃ | CH₃ | F | OCF₃ | CF₃ |
| CH₃ | F | CF₃ | OCF₃ | CH₃ | F | OCF₃ | OCF₃ |
| CH₃ | F | CF₃ | SCF₃ | CH₃ | F | OCF₃ | SCF₃ |
| CH₃ | F | CF₃ | OCHF₂ | CH₃ | F | OCF₃ | OCHF₂ |

TABLE 16-continued

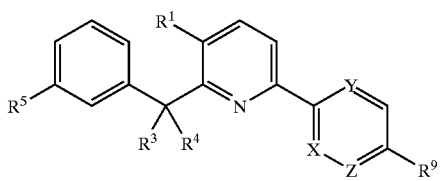

R³ is H; X, Y and Z are CH

| R¹ | R⁴ | R⁵ | R⁹ | R¹ | R⁴ | R⁵ | R⁹ |
|---|---|---|---|---|---|---|---|
| CH₃ | F | CF₃ | SCHF₂ | CH₃ | F | OCF₃ | SCHF₂ |
| CH₃ | F | CF₃ | C₂F₅ | CH₃ | F | OCF₃ | C₂F₅ |
| CH₃ | F | CF₃ | Cl | CH₃ | F | OCF₃ | Cl |
| CH₃ | F | CF₃ | SCH₂CH₃ | CH₃ | F | OCF₃ | SCH₂CH₃ |
| CH₃ | F | OCHF₂ | CF₃ | CH₃ | F | SCF₃ | CF₃ |
| CH₃ | F | OCHF₂ | OCF₃ | CH₃ | F | SCF₃ | OCF₃ |
| CH₃ | F | OCHF₂ | SCF₃ | CH₃ | F | SCF₃ | SCF₃ |
| CH₃ | F | OCHF₂ | OCHF₂ | CH₃ | F | SCF₃ | OCHF₂ |
| CH₃ | F | OCHF₂ | SCHF₂ | CH₃ | F | SCF₃ | SCHF₂ |
| CH₃ | F | OCHF₂ | C₂F₅ | CH₃ | F | SCF₃ | C₂F₅ |
| CH₃ | F | OCHF₂ | Cl | CH₃ | F | SCF₃ | Cl |
| CH₃ | F | OCHF₂ | SCH₂CH₃ | CH₃ | F | SCF₃ | SCH₂CH₃ |
| CH₃ | F | SCHF₂ | CF₃ | CH₃ | F | Cl | CF₃ |
| CH₃ | F | SCHF₂ | OCF₃ | CH₃ | F | Cl | OCF₃ |
| CH₃ | F | SCHF₂ | SCF₃ | CH₃ | F | Cl | SCF₃ |
| CH₃ | F | SCHF₂ | OCHF₂ | CH₃ | F | Cl | OCHF₂ |
| CH₃ | F | SCHF₂ | SCHF₂ | CH₃ | F | Cl | SCHF₂ |
| CH₃ | F | SCHF₂ | C₂F₅ | CH₃ | F | Cl | C₂F₅ |
| CH₃ | F | SCHF₂ | Cl | CH₃ | F | Cl | Cl |
| CH₃ | F | SCHF₂ | SCH₂CH₃ | CH₃ | F | Cl | SCH₂CH₃ |
| CH₃ | Cl | CF₃ | CF₃ | CH₃ | Cl | OCF₃ | CF₃ |
| CH₃ | Cl | CF₃ | OCF₃ | CH₃ | Cl | OCF₃ | OCF₃ |
| CH₃ | Cl | CF₃ | SCF₃ | CH₃ | Cl | OCF₃ | SCF₃ |
| CH₃ | Cl | CF₃ | OCHF₂ | CH₃ | Cl | OCF₃ | OCHF₂ |
| CH₃ | Cl | CF₃ | SCHF₂ | CH₃ | Cl | OCF₃ | SCHF₂ |
| CH₃ | Cl | CF₃ | C₂F₅ | CH₃ | Cl | OCF₃ | C₂F₅ |
| CH₃ | Cl | CF₃ | Cl | CH₃ | Cl | OCF₃ | Cl |
| CH₃ | Cl | CF₃ | SCH₂CH₃ | CH₃ | Cl | OCF₃ | SCH₂CH₃ |
| CH₃ | Cl | OCHF₂ | CF₃ | CH₃ | Cl | SCF₃ | CF₃ |
| CH₃ | Cl | OCHF₂ | OCF₃ | CH₃ | Cl | SCF₃ | OCF₃ |
| CH₃ | Cl | OCHF₂ | SCF₃ | CH₃ | Cl | SCF₃ | SCF₃ |
| CH₃ | Cl | OCHF₂ | OCHF₂ | CH₃ | Cl | SCF₃ | OCHF₂ |
| CH₃ | Cl | OCHF₂ | SCHF₂ | CH₃ | Cl | SCF₃ | SCHF₂ |
| CH₃ | Cl | OCHF₂ | C₂F₅ | CH₃ | Cl | SCF₃ | C₂F₅ |
| CH₃ | Cl | OCHF₂ | Cl | CH₃ | Cl | SCF₃ | Cl |
| CH₃ | Cl | OCHF₂ | SCH₂CH₃ | CH₃ | Cl | SCF₃ | SCH₂CH₃ |
| CH₃ | Cl | SCHF₂ | CF₃ | CH₃ | Cl | Cl | CF₃ |
| CH₃ | Cl | SCHF₂ | OCF₃ | CH₃ | Cl | Cl | OCF₃ |
| CH₃ | Cl | SCHF₂ | SCF₃ | CH₃ | Cl | Cl | SCF₃ |
| CH₃ | Cl | SCHF₂ | OCHF₂ | CH₃ | Cl | Cl | OCHF₂ |
| CH₃ | Cl | SCHF₂ | SCHF₂ | CH₃ | Cl | Cl | SCHF₂ |
| CH₃ | Cl | SCHF₂ | C₂F₅ | CH₃ | Cl | Cl | C₂F₅ |
| CH₃ | Cl | SCHF₂ | Cl | CH₃ | Cl | Cl | Cl |
| CH₃ | Cl | SCHF₂ | SCH₂CH₃ | CH₃ | Cl | Cl | SCH₂CH₃ |

TABLE 17

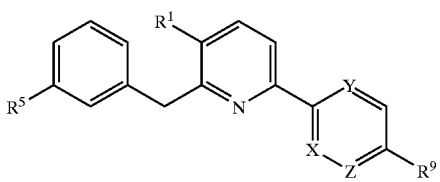

| R¹ | R⁵ | R⁹ | R¹ | R⁵ | R⁹ |
|---|---|---|---|---|---|
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |

TABLE 17-continued

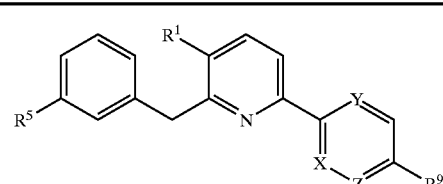

| R¹ | R⁵ | R⁹ | R¹ | R⁵ | R⁹ |
|---|---|---|---|---|---|
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 17-continued

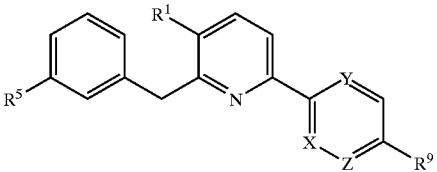

X and Z are CH; Y is N

| R¹ | R⁵ | R⁹ | R¹ | R⁵ | R⁹ |
|---|---|---|---|---|---|
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X and Y are CH; Z is N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X and Y are N; Z is CH

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X is CH; Y and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

Y is CH; X and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

X, Y and Z are N

| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 18

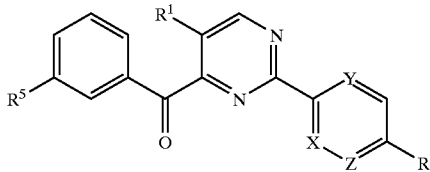

X, Y and Z are CH

| R¹ | R⁵ | R⁹ | R¹ | R⁵ | R⁹ |
|---|---|---|---|---|---|
| H | CF₃ | CF₃ | H | OCF₃ | CF₃ |
| H | CF₃ | OCF₃ | H | OCF₃ | OCF₃ |
| H | CF₃ | SCF₃ | H | OCF₃ | SCF₃ |
| H | CF₃ | OCHF₂ | H | OCF₃ | OCHF₂ |
| H | CF₃ | SCHF₂ | H | OCF₃ | SCHF₂ |
| H | CF₃ | C₂F₅ | H | OCF₃ | C₂F₅ |
| H | CF₃ | Cl | H | OCF₃ | Cl |
| H | CF₃ | SCH₂CH₃ | H | OCF₃ | SCH₂CH₃ |
| H | OCHF₂ | CF₃ | H | SCF₃ | CF₃ |
| H | OCHF₂ | OCF₃ | H | SCF₃ | OCF₃ |
| H | OCHF₂ | SCF₃ | H | SCF₃ | SCF₃ |
| H | OCHF₂ | OCHF₂ | H | SCF₃ | OCHF₂ |
| H | OCHF₂ | SCHF₂ | H | SCF₃ | SCHF₂ |
| H | OCHF₂ | C₂F₅ | H | SCF₃ | C₂F₅ |
| H | OCHF₂ | Cl | H | SCF₃ | Cl |
| H | OCHF₂ | SCH₂CH₃ | H | SCF₃ | SCH₂CH₃ |
| H | SCHF₂ | CF₃ | H | Cl | CF₃ |
| H | SCHF₂ | OCF₃ | H | Cl | OCF₃ |
| H | SCHF₂ | SCF₃ | H | Cl | SCF₃ |
| H | SCHF₂ | OCHF₂ | H | Cl | OCHF₂ |
| H | SCHF₂ | SCHF₂ | H | Cl | SCHF₂ |
| H | SCHF₂ | C₂F₅ | H | Cl | C₂F₅ |
| H | SCHF₂ | Cl | H | Cl | Cl |
| H | SCHF₂ | SCH₂CH₃ | H | Cl | SCH₂CH₃ |
| CH₃ | CF₃ | CF₃ | CH₃ | OCF₃ | CF₃ |
| CH₃ | CF₃ | OCF₃ | CH₃ | OCF₃ | OCF₃ |
| CH₃ | CF₃ | SCF₃ | CH₃ | OCF₃ | SCF₃ |
| CH₃ | CF₃ | OCHF₂ | CH₃ | OCF₃ | OCHF₂ |
| CH₃ | CF₃ | SCHF₂ | CH₃ | OCF₃ | SCHF₂ |
| CH₃ | CF₃ | C₂F₅ | CH₃ | OCF₃ | C₂F₅ |
| CH₃ | CF₃ | Cl | CH₃ | OCF₃ | Cl |
| CH₃ | CF₃ | SCH₂CH₃ | CH₃ | OCF₃ | SCH₂CH₃ |
| CH₃ | OCHF₂ | CF₃ | CH₃ | SCF₃ | CF₃ |
| CH₃ | OCHF₂ | OCF₃ | CH₃ | SCF₃ | OCF₃ |
| CH₃ | OCHF₂ | SCF₃ | CH₃ | SCF₃ | SCF₃ |
| CH₃ | OCHF₂ | OCHF₂ | CH₃ | SCF₃ | OCHF₂ |
| CH₃ | OCHF₂ | SCHF₂ | CH₃ | SCF₃ | SCHF₂ |
| CH₃ | OCHF₂ | C₂F₅ | CH₃ | SCF₃ | C₂F₅ |
| CH₃ | OCHF₂ | Cl | CH₃ | SCF₃ | Cl |
| CH₃ | OCHF₂ | SCH₂CH₃ | CH₃ | SCF₃ | SCH₂CH₃ |
| CH₃ | SCHF₂ | CF₃ | CH₃ | Cl | CF₃ |
| CH₃ | SCHF₂ | OCF₃ | CH₃ | Cl | OCF₃ |
| CH₃ | SCHF₂ | SCF₃ | CH₃ | Cl | SCF₃ |
| CH₃ | SCHF₂ | OCHF₂ | CH₃ | Cl | OCHF₂ |
| CH₃ | SCHF₂ | SCHF₂ | CH₃ | Cl | SCHF₂ |
| CH₃ | SCHF₂ | C₂F₅ | CH₃ | Cl | C₂F₅ |
| CH₃ | SCHF₂ | Cl | CH₃ | Cl | Cl |
| CH₃ | SCHF₂ | SCH₂CH₃ | CH₃ | Cl | SCH₂CH₃ |
| OCH₃ | CF₃ | CF₃ | OCH₃ | OCF₃ | CF₃ |
| OCH₃ | CF₃ | OCF₃ | OCH₃ | OCF₃ | OCF₃ |
| OCH₃ | CF₃ | SCF₃ | OCH₃ | OCF₃ | SCF₃ |
| OCH₃ | CF₃ | OCHF₂ | OCH₃ | OCF₃ | OCHF₂ |
| OCH₃ | CF₃ | SCHF₂ | OCH₃ | OCF₃ | SCHF₂ |
| OCH₃ | CF₃ | C₂F₅ | OCH₃ | OCF₃ | C₂F₅ |
| OCH₃ | CF₃ | Cl | OCH₃ | OCF₃ | Cl |
| OCH₃ | CF₃ | SCH₂CH₃ | OCH₃ | OCF₃ | SCH₂CH₃ |
| OCH₃ | OCHF₂ | CF₃ | OCH₃ | SCF₃ | CF₃ |
| OCH₃ | OCHF₂ | OCF₃ | OCH₃ | SCF₃ | OCF₃ |
| OCH₃ | OCHF₂ | SCF₃ | OCH₃ | SCF₃ | SCF₃ |
| OCH₃ | OCHF₂ | OCHF₂ | OCH₃ | SCF₃ | OCHF₂ |
| OCH₃ | OCHF₂ | SCHF₂ | OCH₃ | SCF₃ | SCHF₂ |
| OCH₃ | OCHF₂ | C₂F₅ | OCH₃ | SCF₃ | C₂F₅ |
| OCH₃ | OCHF₂ | Cl | OCH₃ | SCF₃ | Cl |
| OCH₃ | OCHF₂ | SCH₂CH₃ | OCH₃ | SCF₃ | SCH₂CH₃ |
| OCH₃ | SCHF₂ | CF₃ | OCH₃ | Cl | CF₃ |
| OCH₃ | SCHF₂ | OCF₃ | OCH₃ | Cl | OCF₃ |
| OCH₃ | SCHF₂ | SCF₃ | OCH₃ | Cl | SCF₃ |
| OCH₃ | SCHF₂ | OCHF₂ | OCH₃ | Cl | OCHF₂ |
| OCH₃ | SCHF₂ | SCHF₂ | OCH₃ | Cl | SCHF₂ |
| OCH₃ | SCHF₂ | C₂F₅ | OCH₃ | Cl | C₂F₅ |
| OCH₃ | SCHF₂ | Cl | OCH₃ | Cl | Cl |
| OCH₃ | SCHF₂ | SCH₂CH₃ | OCH₃ | Cl | SCH₂CH₃ |
| CH₂CH₃ | CF₃ | CF₃ | CH₂CH₃ | OCF₃ | CF₃ |
| CH₂CH₃ | CF₃ | OCF₃ | CH₂CH₃ | OCF₃ | OCF₃ |
| CH₂CH₃ | CF₃ | SCF₃ | CH₂CH₃ | OCF₃ | SCF₃ |
| CH₂CH₃ | CF₃ | OCHF₂ | CH₂CH₃ | OCF₃ | OCHF₂ |
| CH₂CH₃ | CF₃ | SCHF₂ | CH₂CH₃ | OCF₃ | SCHF₂ |
| CH₂CH₃ | CF₃ | C₂F₅ | CH₂CH₃ | OCF₃ | C₂F₅ |
| CH₂CH₃ | CF₃ | Cl | CH₂CH₃ | OCF₃ | Cl |
| CH₂CH₃ | CF₃ | SCH₂CH₃ | CH₂CH₃ | OCF₃ | SCH₂CH₃ |

TABLE 18-continued

Structure: phenyl-C(=O)-pyrimidine(R1)-heterocycle(X,Y,Z)-R9, with R5 on phenyl

X, Y and Z are CH

| R¹ | R⁵ | R⁹ | R¹ | R⁵ | R⁹ |
|---|---|---|---|---|---|
| CH₂CH₃ | OCHF₂ | CF₃ | CH₂CH₃ | SCF₃ | CF₃ |
| CH₂CH₃ | OCHF₂ | OCF₃ | CH₂CH₃ | SCF₃ | OCF₃ |
| CH₂CH₃ | OCHF₂ | SCF₃ | CH₂CH₃ | SCF₃ | SCF₃ |
| CH₂CH₃ | OCHF₂ | OCHF₂ | CH₂CH₃ | SCF₃ | OCHF₂ |
| CH₂CH₃ | OCHF₂ | SCHF₂ | CH₂CH₃ | SCF₃ | SCHF₂ |
| CH₂CH₃ | OCHF₂ | C₂F₅ | CH₂CH₃ | SCF₃ | C₂F₅ |
| CH₂CH₃ | OCHF₂ | Cl | CH₂CH₃ | SCF₃ | Cl |
| CH₂CH₃ | OCHF₂ | SCH₂CH₃ | CH₂CH₃ | SCF₃ | SCH₂CH₃ |
| CH₂CH₃ | SCHF₂ | CF₃ | CH₂CH₃ | Cl | CF₃ |
| CH₂CH₃ | SCHF₂ | OCF₃ | CH₂CH₃ | Cl | OCF₃ |
| CH₂CH₃ | SCHF₂ | SCF₃ | CH₂CH₃ | Cl | SCF₃ |
| CH₂CH₃ | SCHF₂ | OCHF₂ | CH₂CH₃ | Cl | OCHF₂ |
| CH₂CH₃ | SCHF₂ | SCHF₂ | CH₂CH₃ | Cl | SCHF₂ |
| CH₂CH₃ | SCHF₂ | C₂F₅ | CH₂CH₃ | Cl | C₂F₅ |
| CH₂CH₃ | SCHF₂ | Cl | CH₂CH₃ | Cl | Cl |
| CH₂CH₃ | SCHF₂ | SCH₂CH₃ | CH₂CH₃ | Cl | SCH₂CH₃ |

TABLE 19

Structure: phenyl-C(=O)-pyrimidine(R1)-heterocycle(X,Y,Z)-R9, with R5 on phenyl

| R¹ | R⁵ | R⁹ | R¹ | R⁵ | R⁹ |
|---|---|---|---|---|---|
| *X is N; Y and Z are CH* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X and Y are CH; Z is N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X and Y are N; Z is CH* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X is CH; Y and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *Y is CH; X and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X, Y and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 20

Structure: pyridine(R5)-C(=O)-pyrimidine(R1)-heterocycle(X,Y,Z)-R9

| R¹ | R⁵ | R⁹ | R¹ | R⁵ | R⁹ |
|---|---|---|---|---|---|
| *X, Y and Z are CH* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X and Z are CH; Y is N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X and Y are CH; Z is N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X and Y are N; Z is CH* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X is CH; Y and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *Y is CH; X and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| *X, Y and Z are N* | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 19-continued

| R¹ | R⁵ | R⁹ | R¹ | R⁵ | R⁹ |
|---|---|---|---|---|---|
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 21

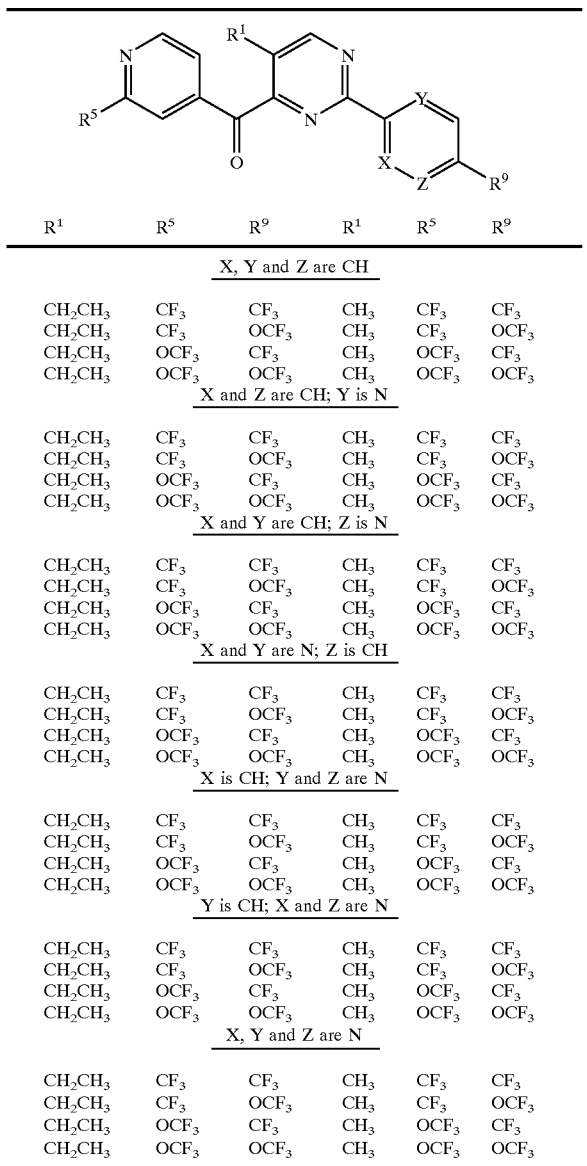

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 22

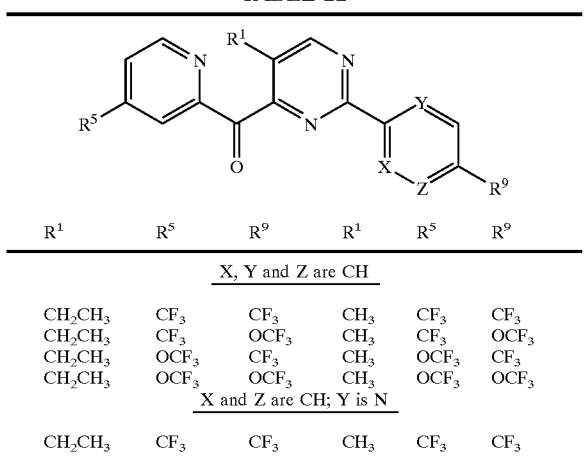

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 23

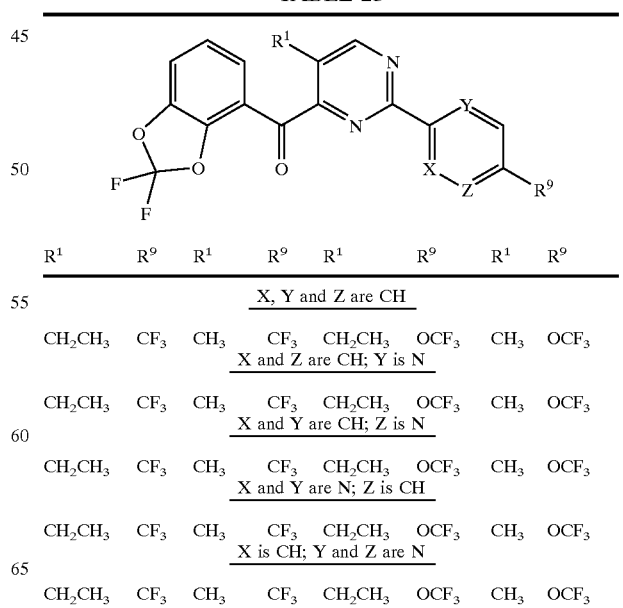

| R¹ | R⁹ | R¹ | R⁹ | R¹ | R⁹ | R¹ | R⁹ |
|---|---|---|---|---|---|---|---|
| X, Y and Z are CH | | | | | | | |
| CH₂CH₃ | CF₃ | CH₃ | CF₃ | CH₂CH₃ | OCF₃ | CH₃ | OCF₃ |
| X and Z are CH; Y is N | | | | | | | |
| CH₂CH₃ | CF₃ | CH₃ | CF₃ | CH₂CH₃ | OCF₃ | CH₃ | OCF₃ |
| X and Y are CH; Z is N | | | | | | | |
| CH₂CH₃ | CF₃ | CH₃ | CF₃ | CH₂CH₃ | OCF₃ | CH₃ | OCF₃ |
| X and Y are N; Z is CH | | | | | | | |
| CH₂CH₃ | CF₃ | CH₃ | CF₃ | CH₂CH₃ | OCF₃ | CH₃ | OCF₃ |
| X is CH; Y and Z are N | | | | | | | |
| CH₂CH₃ | CF₃ | CH₃ | CF₃ | CH₂CH₃ | OCF₃ | CH₃ | OCF₃ |

TABLE 23-continued

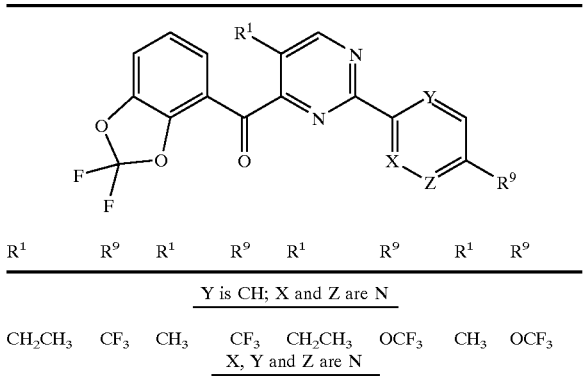

| R¹ | R⁹ | R¹ | R⁹ | R¹ | R⁹ | R¹ | R⁹ |
|---|---|---|---|---|---|---|---|
| Y is CH; X and Z are N ||||||||
| CH₂CH₃ | CF₃ | CH₃ | CF₃ | CH₂CH₃ | OCF₃ | CH₃ | OCF₃ |
| X, Y and Z are N ||||||||
| CH₂CH₃ | CF₃ | CH₃ | CF₃ | CH₂CH₃ | OCF₃ | CH₃ | OCF₃ |

TABLE 24

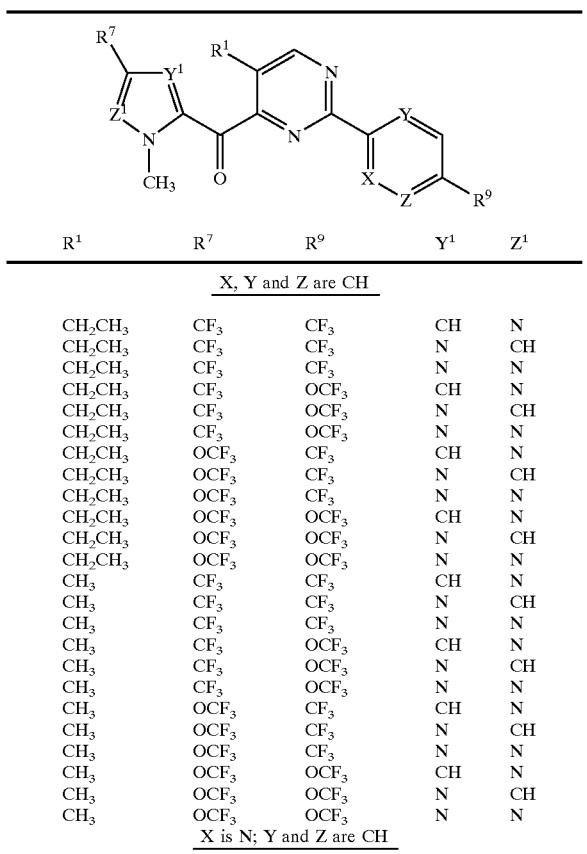

| R¹ | R⁷ | R⁹ | Y¹ | Z¹ |
|---|---|---|---|---|
| X, Y and Z are CH |||||
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |
| X is N; Y and Z are CH |||||
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |

TABLE 24-continued

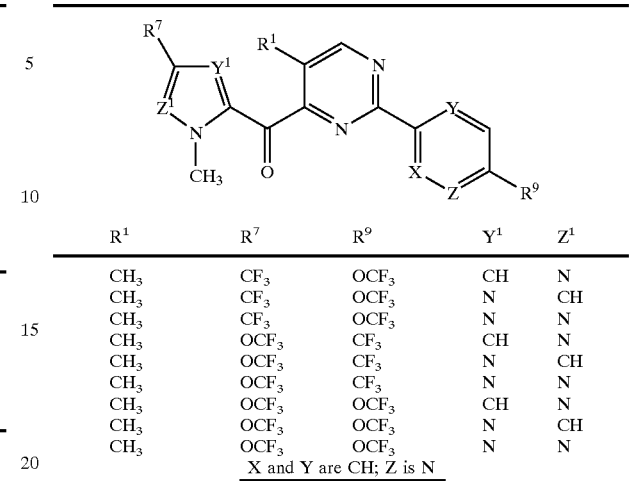

| R¹ | R⁷ | R⁹ | Y¹ | Z¹ |
|---|---|---|---|---|
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |
| X and Y are CH; Z is N |||||
| CH₂CH₃ | CF₃ | CF₃ | CH | N |
| CH₂CH₃ | CF₃ | CF₃ | N | CH |
| CH₂CH₃ | CF₃ | CF₃ | N | N |
| CH₂CH₃ | CF₃ | OCF₃ | CH | N |
| CH₂CH₃ | CF₃ | OCF₃ | N | CH |
| CH₂CH₃ | CF₃ | OCF₃ | N | N |
| CH₂CH₃ | OCF₃ | CF₃ | CH | N |
| CH₂CH₃ | OCF₃ | CF₃ | N | CH |
| CH₂CH₃ | OCF₃ | CF₃ | N | N |
| CH₂CH₃ | OCF₃ | OCF₃ | CH | N |
| CH₂CH₃ | OCF₃ | OCF₃ | N | CH |
| CH₂CH₃ | OCF₃ | OCF₃ | N | N |
| CH₃ | CF₃ | CF₃ | CH | N |
| CH₃ | CF₃ | CF₃ | N | CH |
| CH₃ | CF₃ | CF₃ | N | N |
| CH₃ | CF₃ | OCF₃ | CH | N |
| CH₃ | CF₃ | OCF₃ | N | CH |
| CH₃ | CF₃ | OCF₃ | N | N |
| CH₃ | OCF₃ | CF₃ | CH | N |
| CH₃ | OCF₃ | CF₃ | N | CH |
| CH₃ | OCF₃ | CF₃ | N | N |
| CH₃ | OCF₃ | OCF₃ | CH | N |
| CH₃ | OCF₃ | OCF₃ | N | CH |
| CH₃ | OCF₃ | OCF₃ | N | N |

TABLE 25

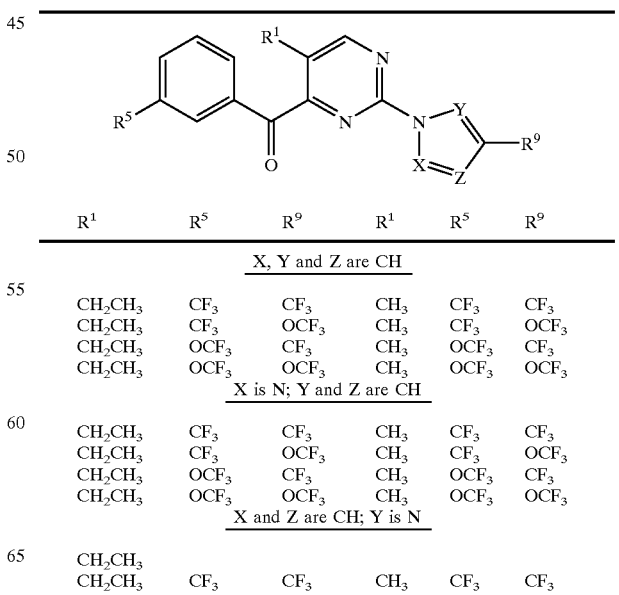

| R¹ | R⁵ | R⁹ | R¹ | R⁵ | R⁹ |
|---|---|---|---|---|---|
| X, Y and Z are CH ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH ||||||
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N ||||||
| CH₂CH₃ |  |  |  |  |  |
| CH₂CH₃ | CF₃ | CF₃ | CH₃ | CF₃ | CF₃ |

TABLE 25-continued

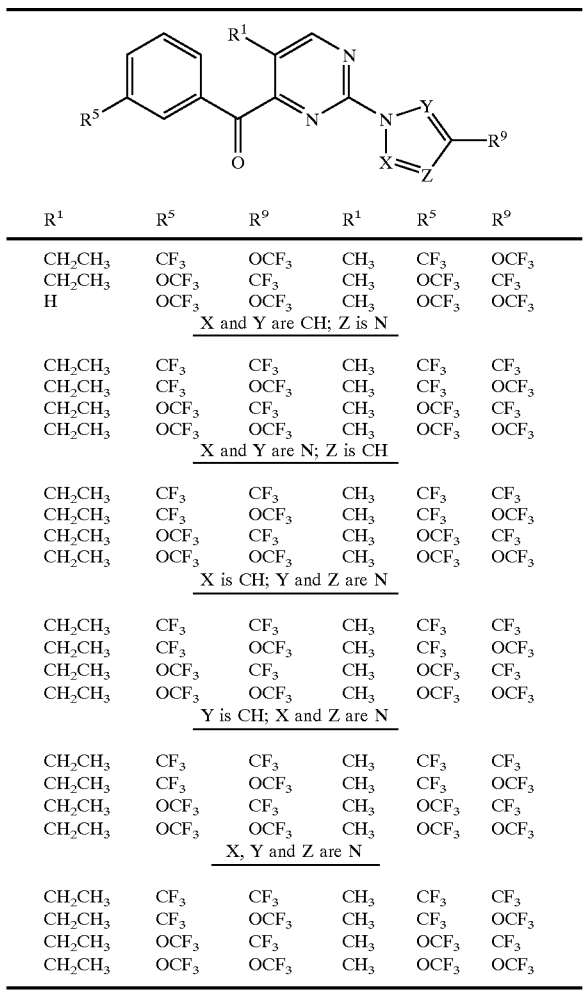

| R¹ | R⁵ | R⁹ | R¹ | R⁵ | R⁹ |
|---|---|---|---|---|---|
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| H | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 26

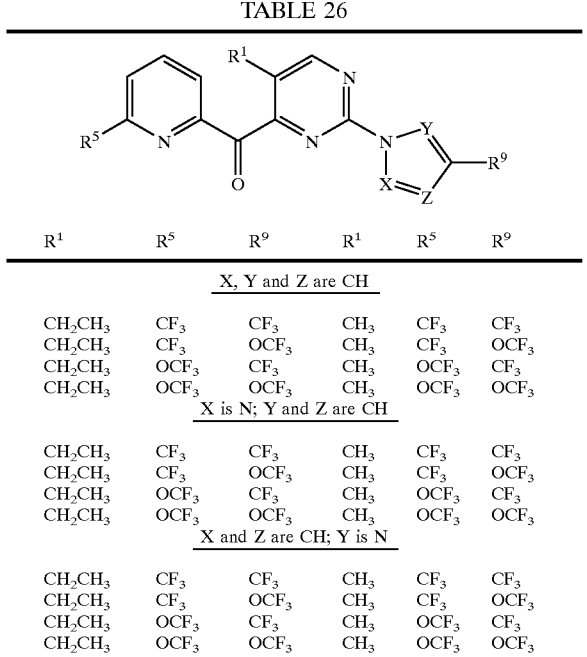

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 26-continued

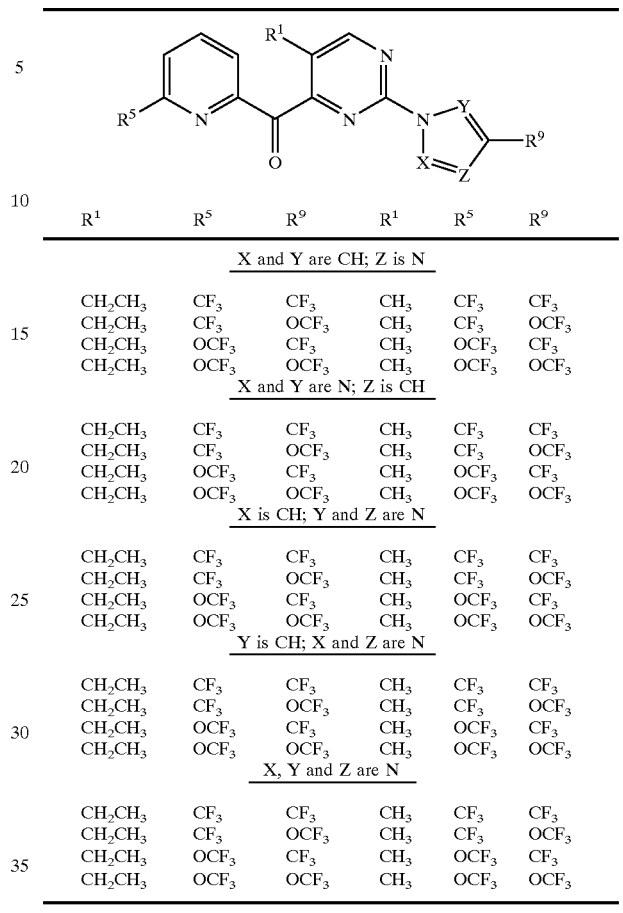

| R¹ | R⁵ | R⁹ | R¹ | R⁵ | R⁹ |
|---|---|---|---|---|---|
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 27

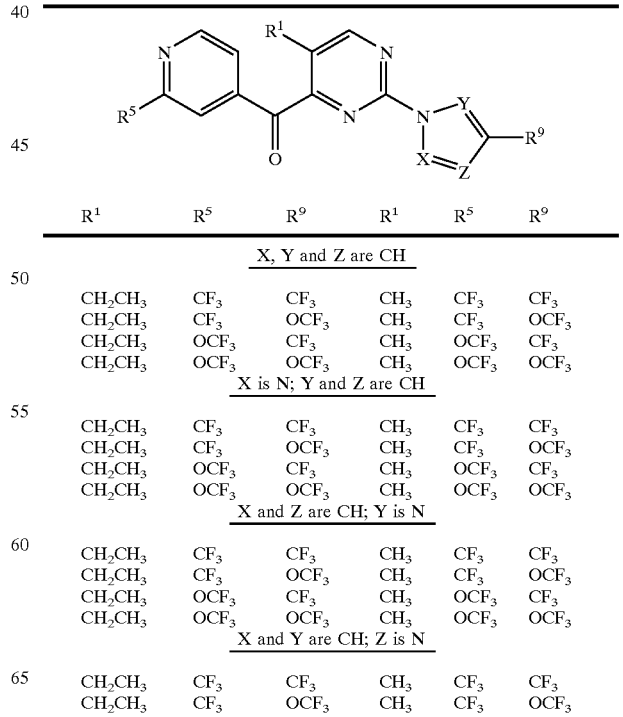

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |

TABLE 27-continued

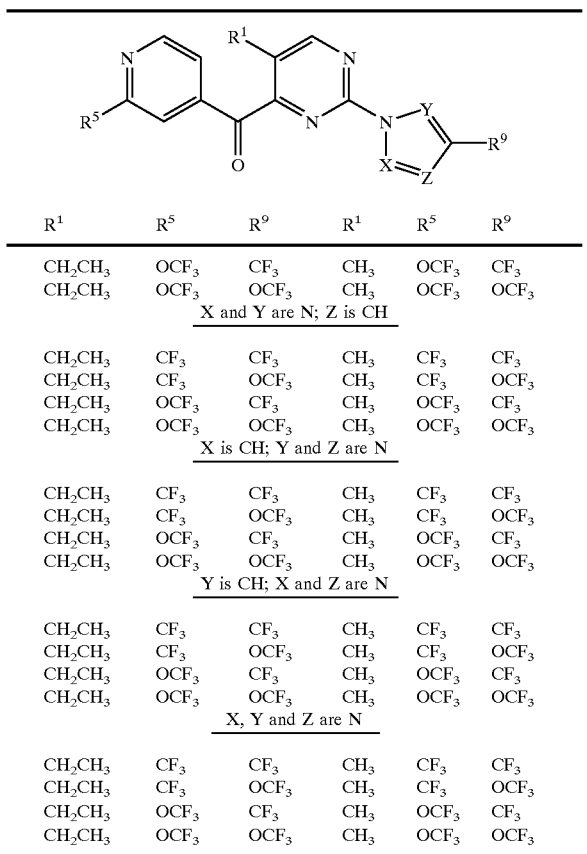

| R¹ | R⁵ | R⁹ | R¹ | R⁵ | R⁹ |
|---|---|---|---|---|---|
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 28

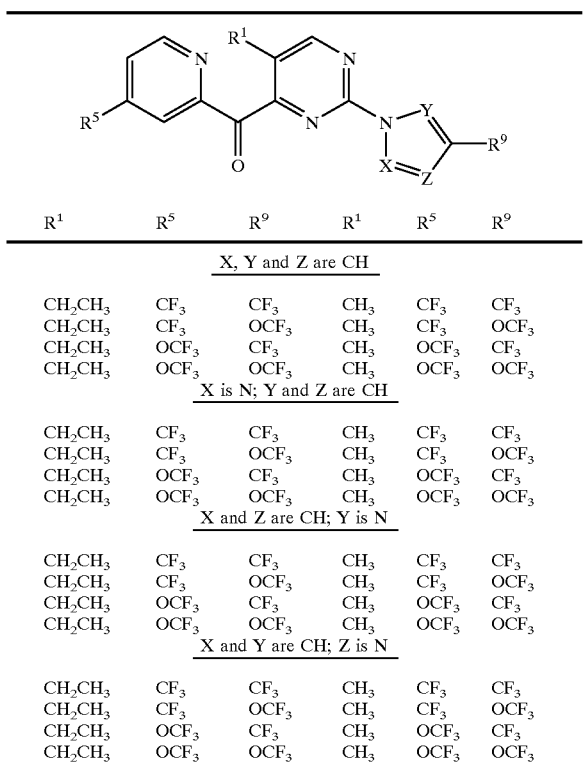

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Z are CH; Y is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 28-continued

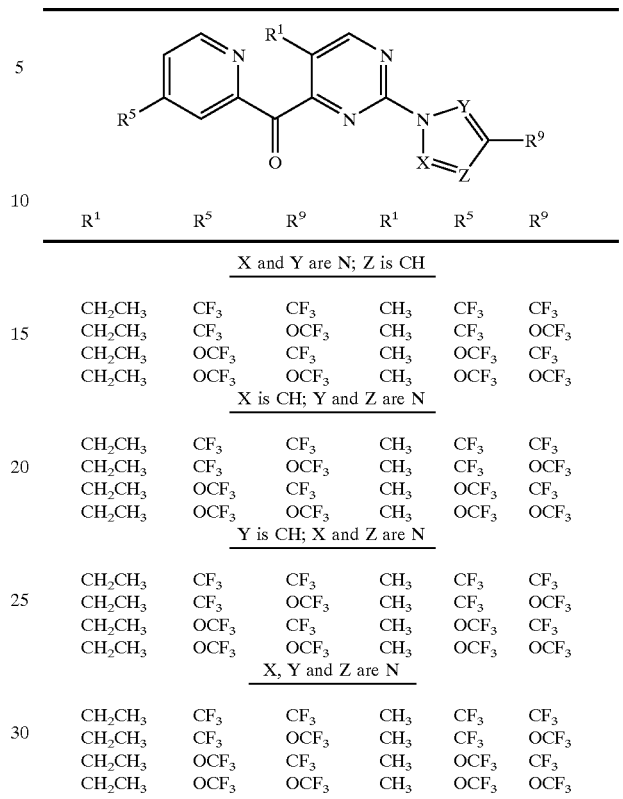

| R¹ | R⁵ | R⁹ | R¹ | R⁵ | R⁹ |
|---|---|---|---|---|---|
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 29

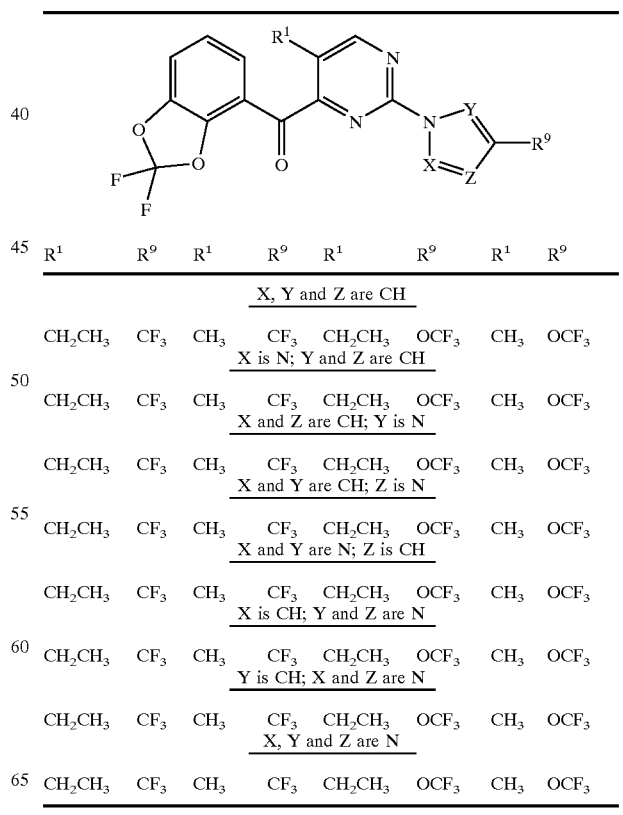

| R¹ | R⁹ | R¹ | R⁹ | R¹ | R⁹ | R¹ | R⁹ |
|---|---|---|---|---|---|---|---|
| X, Y and Z are CH | | | | | | | |
| CH₂CH₃ | CF₃ | CH₃ | CF₃ | CH₂CH₃ | OCF₃ | CH₃ | OCF₃ |
| X is N; Y and Z are CH | | | | | | | |
| CH₂CH₃ | CF₃ | CH₃ | CF₃ | CH₂CH₃ | OCF₃ | CH₃ | OCF₃ |
| X and Z are CH; Y is N | | | | | | | |
| CH₂CH₃ | CF₃ | CH₃ | CF₃ | CH₂CH₃ | OCF₃ | CH₃ | OCF₃ |
| X and Y are CH; Z is N | | | | | | | |
| CH₂CH₃ | CF₃ | CH₃ | CF₃ | CH₂CH₃ | OCF₃ | CH₃ | OCF₃ |
| X and Y are N; Z is CH | | | | | | | |
| CH₂CH₃ | CF₃ | CH₃ | CF₃ | CH₂CH₃ | OCF₃ | CH₃ | OCF₃ |
| X is CH; Y and Z are N | | | | | | | |
| CH₂CH₃ | CF₃ | CH₃ | CF₃ | CH₂CH₃ | OCF₃ | CH₃ | OCF₃ |
| Y is CH; X and Z are N | | | | | | | |
| CH₂CH₃ | CF₃ | CH₃ | CF₃ | CH₂CH₃ | OCF₃ | CH₃ | OCF₃ |
| X, Y and Z are N | | | | | | | |
| CH₂CH₃ | CF₃ | CH₃ | CF₃ | CH₂CH₃ | OCF₃ | CH₃ | OCF₃ |

TABLE 30

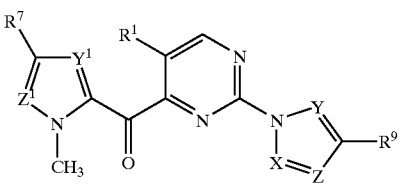

| R$^1$ | R$^7$ | R$^9$ | Y$^1$ | Z$^1$ |
|---|---|---|---|---|
| X is N; Y and Z are CH ||||| 
| CH$_2$CH$_3$ | CF$_3$ | CF$_3$ | CH | N |
| CH$_2$CH$_3$ | CF$_3$ | CF$_3$ | N | CH |
| CH$_2$CH$_3$ | CF$_3$ | CF$_3$ | N | N |
| CH$_2$CH$_3$ | CF$_3$ | OCF$_3$ | CH | N |
| CH$_2$CH$_3$ | CF$_3$ | OCF$_3$ | N | CH |
| CH$_2$CH$_3$ | CF$_3$ | OCF$_3$ | N | N |
| CH$_2$CH$_3$ | OCF$_3$ | CF$_3$ | CH | N |
| CH$_2$CH$_3$ | OCF$_3$ | CF$_3$ | N | CH |
| CH$_2$CH$_3$ | OCF$_3$ | CF$_3$ | N | N |
| CH$_2$CH$_3$ | OCF$_3$ | OCF$_3$ | CH | N |
| CH$_2$CH$_3$ | OCF$_3$ | OCF$_3$ | N | CH |
| CH$_2$CH$_3$ | OCF$_3$ | OCF$_3$ | N | N |
| CH$_3$ | CF$_3$ | CF$_3$ | CH | N |
| CH$_3$ | CF$_3$ | CF$_3$ | N | CH |
| CH$_3$ | CF$_3$ | CF$_3$ | N | N |
| CH$_3$ | CF$_3$ | OCF$_3$ | CH | N |
| CH$_3$ | CF$_3$ | OCF$_3$ | N | CH |
| CH$_3$ | CF$_3$ | OCF$_3$ | N | N |
| CH$_3$ | OCF$_3$ | CF$_3$ | CH | N |
| CH$_3$ | OCF$_3$ | CF$_3$ | N | CH |
| CH$_3$ | OCF$_3$ | CF$_3$ | N | N |
| CH$_3$ | OCF$_3$ | OCF$_3$ | CH | N |
| CH$_3$ | OCF$_3$ | OCF$_3$ | N | CH |
| CH$_3$ | OCF$_3$ | OCF$_3$ | N | N |
| X and Z are CH; Y is N ||||| 
| CH$_2$CH$_3$ | CF$_3$ | CF$_3$ | CH | N |
| CH$_2$CH$_3$ | CF$_3$ | CF$_3$ | N | CH |
| CH$_2$CH$_3$ | CF$_3$ | CF$_3$ | N | N |
| CH$_2$CH$_3$ | CF$_3$ | OCF$_3$ | CH | N |
| CH$_2$CH$_3$ | CF$_3$ | OCF$_3$ | N | CH |
| CH$_2$CH$_3$ | CF$_3$ | OCF$_3$ | N | N |
| CH$_2$CH$_3$ | OCF$_3$ | CF$_3$ | CH | N |
| CH$_2$CH$_3$ | OCF$_3$ | CF$_3$ | N | CH |
| CH$_2$CH$_3$ | OCF$_3$ | CF$_3$ | N | N |
| CH$_2$CH$_3$ | OCF$_3$ | OCF$_3$ | CH | N |
| CH$_2$CH$_3$ | OCF$_3$ | OCF$_3$ | N | CH |
| CH$_2$CH$_3$ | OCF$_3$ | OCF$_3$ | N | N |
| CH$_3$ | CF$_3$ | CF$_3$ | CH | N |
| CH$_3$ | CF$_3$ | CF$_3$ | N | CH |
| CH$_3$ | CF$_3$ | CF$_3$ | N | N |
| CH$_3$ | CF$_3$ | OCF$_3$ | CH | N |
| CH$_3$ | CF$_3$ | OCF$_3$ | N | CH |
| CH$_3$ | CF$_3$ | OCF$_3$ | N | N |
| CH$_3$ | OCF$_3$ | CF$_3$ | CH | N |
| CH$_3$ | OCF$_3$ | CF$_3$ | N | CH |
| CH$_3$ | OCF$_3$ | CF$_3$ | N | N |
| CH$_3$ | OCF$_3$ | OCF$_3$ | CH | N |
| CH$_3$ | OCF$_3$ | OCF$_3$ | N | CH |
| CH$_3$ | OCF$_3$ | OCF$_3$ | N | N |
| X and Y are CH; Z is N ||||| 
| CH$_2$CH$_3$ | CF$_3$ | CF$_3$ | CH | N |
| CH$_2$CH$_3$ | CF$_3$ | CF$_3$ | N | CH |
| CH$_2$CH$_3$ | CF$_3$ | CF$_3$ | N | N |
| CH$_2$CH$_3$ | CF$_3$ | OCF$_3$ | CH | N |
| CH$_2$CH$_3$ | CF$_3$ | OCF$_3$ | N | CH |
| CH$_2$CH$_3$ | CF$_3$ | OCF$_3$ | N | N |
| CH$_2$CH$_3$ | OCF$_3$ | CF$_3$ | CH | N |
| CH$_2$CH$_3$ | OCF$_3$ | CF$_3$ | N | CH |
| CH$_2$CH$_3$ | OCF$_3$ | CF$_3$ | N | N |
| CH$_2$CH$_3$ | OCF$_3$ | OCF$_3$ | CH | N |
| CH$_2$CH$_3$ | OCF$_3$ | OCF$_3$ | N | CH |
| CH$_2$CH$_3$ | OCF$_3$ | OCF$_3$ | N | N |
| CH$_3$ | CF$_3$ | CF$_3$ | CH | N |

TABLE 30-continued

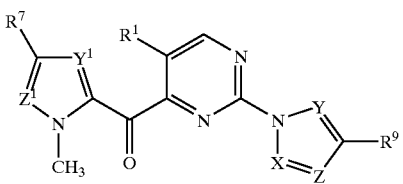

| R$^1$ | R$^7$ | R$^9$ | Y$^1$ | Z$^1$ |
|---|---|---|---|---|
| CH$_3$ | CF$_3$ | CF$_3$ | N | CH |
| CH$_3$ | CF$_3$ | CF$_3$ | N | N |
| CH$_3$ | CF$_3$ | OCF$_3$ | CH | N |
| CH$_3$ | CF$_3$ | OCF$_3$ | N | CH |
| CH$_3$ | CF$_3$ | OCF$_3$ | N | N |
| CH$_3$ | OCF$_3$ | CF$_3$ | CH | N |
| CH$_3$ | OCF$_3$ | CF$_3$ | N | CH |
| CH$_3$ | OCF$_3$ | CF$_3$ | N | N |
| CH$_3$ | OCF$_3$ | OCF$_3$ | CH | N |
| CH$_3$ | OCF$_3$ | OCF$_3$ | N | CH |
| CH$_3$ | OCF$_3$ | OCF$_3$ | N | N |
| X is CH; Y and Z are N ||||| 
| CH$_2$CH$_3$ | CF$_3$ | CF$_3$ | CH | N |
| CH$_2$CH$_3$ | CF$_3$ | CF$_3$ | N | CH |
| CH$_2$CH$_3$ | CF$_3$ | CF$_3$ | N | N |
| CH$_2$CH$_3$ | CF$_3$ | OCF$_3$ | CH | N |
| CH$_2$CH$_3$ | CF$_3$ | OCF$_3$ | N | CH |
| CH$_2$CH$_3$ | CF$_3$ | OCF$_3$ | N | N |
| CH$_2$CH$_3$ | OCF$_3$ | CF$_3$ | CH | N |
| CH$_2$CH$_3$ | OCF$_3$ | CF$_3$ | N | CH |
| CH$_2$CH$_3$ | OCF$_3$ | CF$_3$ | N | N |
| CH$_2$CH$_3$ | OCF$_3$ | OCF$_3$ | CH | N |
| CH$_2$CH$_3$ | OCF$_3$ | OCF$_3$ | N | CH |
| CH$_2$CH$_3$ | OCF$_3$ | OCF$_3$ | N | N |
| CH$_3$ | CF$_3$ | CF$_3$ | CH | N |
| CH$_3$ | CF$_3$ | CF$_3$ | N | CH |
| CH$_3$ | CF$_3$ | CF$_3$ | N | N |
| CH$_3$ | CF$_3$ | OCF$_3$ | CH | N |
| CH$_3$ | CF$_3$ | OCF$_3$ | N | CH |
| CH$_3$ | CF$_3$ | OCF$_3$ | N | N |
| CH$_3$ | OCF$_3$ | CF$_3$ | CH | N |
| CH$_3$ | OCF$_3$ | CF$_3$ | N | CH |
| CH$_3$ | OCF$_3$ | CF$_3$ | N | N |
| CH$_3$ | OCF$_3$ | OCF$_3$ | CH | N |
| CH$_3$ | OCF$_3$ | OCF$_3$ | N | CH |
| CH$_3$ | OCF$_3$ | OCF$_3$ | N | N |

TABLE 31

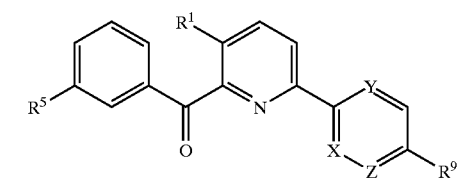

X, Y and Z are CH

| R$^1$ | R$^5$ | R$^9$ | R$^1$ | R$^5$ | R$^9$ |
|---|---|---|---|---|---|
| CH$_2$CH$_3$ | CF$_3$ | CF$_3$ | CH$_2$CH$_3$ | OCF$_3$ | CF$_3$ |
| CH$_2$CH$_3$ | CF$_3$ | OCF$_3$ | CH$_2$CH$_3$ | OCF$_3$ | OCF$_3$ |
| CH$_2$CH$_3$ | CF$_3$ | SCF$_3$ | CH$_2$CH$_3$ | OCF$_3$ | SCF$_3$ |
| CH$_2$CH$_3$ | CF$_3$ | OCHF$_2$ | CH$_2$CH$_3$ | OCF$_3$ | OCHF$_2$ |
| CH$_2$CH$_3$ | CF$_3$ | SCHF$_2$ | CH$_2$CH$_3$ | OCF$_3$ | SCHF$_2$ |
| CH$_2$CH$_3$ | CF$_3$ | C$_2$F$_5$ | CH$_2$CH$_3$ | OCF$_3$ | C$_2$F$_5$ |
| CH$_2$CH$_3$ | CF$_3$ | Cl | CH$_2$CH$_3$ | OCF$_3$ | Cl |
| CH$_2$CH$_3$ | CF$_3$ | SCH$_2$CH$_3$ | CH$_2$CH$_3$ | OCF$_3$ | SCH$_2$CH$_3$ |
| CH$_2$CH$_3$ | OCHF$_2$ | CF$_3$ | CH$_2$CH$_3$ | SCF$_3$ | CF$_3$ |
| CH$_2$CH$_3$ | OCHF$_2$ | OCF$_3$ | CH$_2$CH$_3$ | SCF$_3$ | OCF$_3$ |
| CH$_2$CH$_3$ | OCHF$_2$ | SCF$_3$ | CH$_2$CH$_3$ | SCF$_3$ | SCF$_3$ |
| CH$_2$CH$_3$ | OCHF$_2$ | OCHF$_2$ | CH$_2$CH$_3$ | SCF$_3$ | OCHF$_2$ |
| CH$_2$CH$_3$ | OCHF$_2$ | SCHF$_2$ | CH$_2$CH$_3$ | SCF$_3$ | SCHF$_2$ |

TABLE 31-continued

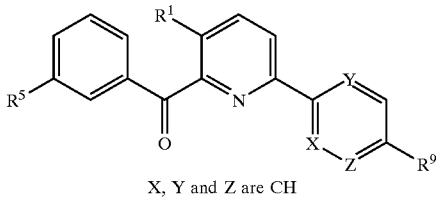

X, Y and Z are CH

| R¹ | R⁵ | R⁹ | R¹ | R⁵ | R⁹ |
|---|---|---|---|---|---|
| CH$_2$CH$_3$ | OCHF$_2$ | C$_2$F$_5$ | CH$_2$CH$_3$ | SCF$_3$ | C$_2$F$_5$ |
| CH$_2$CH$_3$ | OCHF$_2$ | Cl | CH$_2$CH$_3$ | SCF$_3$ | Cl |
| CH$_2$CH$_3$ | OCHF$_2$ | SCH$_2$CH$_3$ | CH$_2$CH$_3$ | SCF$_3$ | SCH$_2$CH$_3$ |
| CH$_2$CH$_3$ | SCHF$_2$ | CF$_3$ | CH$_2$CH$_3$ | Cl | CF$_3$ |
| CH$_2$CH$_3$ | SCHF$_2$ | OCF$_3$ | CH$_2$CH$_3$ | Cl | OCF$_3$ |
| CH$_2$CH$_3$ | SCHF$_2$ | SCF$_3$ | CH$_2$CH$_3$ | Cl | SCF$_3$ |
| CH$_2$CH$_3$ | SCHF$_2$ | OCHF$_2$ | CH$_2$CH$_3$ | Cl | OCHF$_2$ |
| CH$_2$CH$_3$ | SCHF$_2$ | SCHF$_2$ | CH$_2$CH$_3$ | Cl | SCHF$_2$ |
| CH$_2$CH$_3$ | SCHF$_2$ | C$_2$F$_5$ | CH$_2$CH$_3$ | Cl | C$_2$F$_5$ |
| CH$_2$CH$_3$ | SCHF$_2$ | Cl | CH$_2$CH$_3$ | Cl | Cl |
| CH$_2$CH$_3$ | SCHF$_2$ | SCH$_2$CH$_3$ | CH$_2$CH$_3$ | Cl | SCH$_2$CH$_3$ |
| CH$_3$ | CF$_3$ | CF$_3$ | CH$_3$ | OCF$_3$ | CF$_3$ |
| CH$_3$ | CF$_3$ | OCF$_3$ | CH$_3$ | OCF$_3$ | OCF$_3$ |
| CH$_3$ | CF$_3$ | SCF$_3$ | CH$_3$ | OCF$_3$ | SCF$_3$ |
| CH$_3$ | CF$_3$ | OCHF$_2$ | CH$_3$ | OCF$_3$ | OCHF$_2$ |
| CH$_3$ | CF$_3$ | SCHF$_2$ | CH$_3$ | OCF$_3$ | SCHF$_2$ |
| CH$_3$ | CF$_3$ | C$_2$F$_5$ | CH$_3$ | OCF$_3$ | C$_2$F$_5$ |
| CH$_3$ | CF$_3$ | Cl | CH$_3$ | OCF$_3$ | Cl |
| CH$_3$ | CF$_3$ | SCH$_2$CH$_3$ | CH$_3$ | OCF$_3$ | SCH$_2$CH$_3$ |
| CH$_3$ | OCHF$_2$ | CF$_3$ | CH$_3$ | SCF$_3$ | CF$_3$ |
| CH$_3$ | OCHF$_2$ | OCF$_3$ | CH$_3$ | SCF$_3$ | OCF$_3$ |
| CH$_3$ | OCHF$_2$ | SCF$_3$ | CH$_3$ | SCF$_3$ | SCF$_3$ |
| CH$_3$ | OCHF$_2$ | OCHF$_2$ | CH$_3$ | SCF$_3$ | OCHF$_2$ |
| CH$_3$ | OCHF$_2$ | SCHF$_2$ | CH$_3$ | SCF$_3$ | SCHF$_2$ |
| CH$_3$ | OCHF$_2$ | C$_2$F$_5$ | CH$_3$ | SCF$_3$ | C$_2$F$_5$ |
| CH$_3$ | OCHF$_2$ | Cl | CH$_3$ | SCF$_3$ | Cl |
| CH$_3$ | OCHF$_2$ | SCH$_2$CH$_3$ | CH$_3$ | SCF$_3$ | SCH$_2$CH$_3$ |
| CH$_3$ | SCHF$_2$ | CF$_3$ | CH$_3$ | Cl | CF$_3$ |
| CH$_3$ | SCHF$_2$ | OCF$_3$ | CH$_3$ | Cl | OCF$_3$ |
| CH$_3$ | SCHF$_2$ | SCF$_3$ | CH$_3$ | Cl | SCF$_3$ |
| CH$_3$ | SCHF$_2$ | OCHF$_2$ | CH$_3$ | Cl | OCHF$_2$ |
| CH$_3$ | SCHF$_2$ | SCHF$_2$ | CH$_3$ | Cl | SCHF$_2$ |
| CH$_3$ | SCHF$_2$ | C$_2$F$_5$ | CH$_3$ | Cl | C$_2$F$_5$ |
| CH$_3$ | SCHF$_2$ | Cl | CH$_3$ | Cl | Cl |
| CH$_3$ | SCHF$_2$ | SCH$_2$CH$_3$ | CH$_3$ | Cl | SCH$_2$CH$_3$ |

TABLE 32

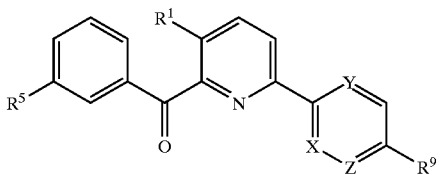

| R¹ | R⁵ | R⁹ | R¹ | R⁵ | R⁹ |
|---|---|---|---|---|---|
| X is N; Y and Z are CH ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X and Z are CH; Y is N ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X and Y are CH; Z is N ||||||
| CH$_2$CH$_3$ | CF$_3$ | CF$_3$ | CH$_3$ | CF$_3$ | CF$_3$ |

TABLE 32-continued

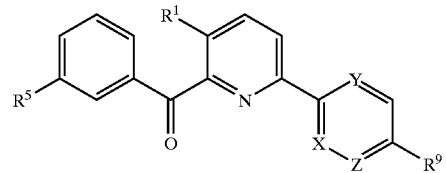

| R¹ | R⁵ | R⁹ | R¹ | R⁵ | R⁹ |
|---|---|---|---|---|---|
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X and Y are N; Z is CH ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X is CH; Y and Z are N ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| Y is CH; X and Z are N ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X, Y and Z are N ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |

TABLE 33

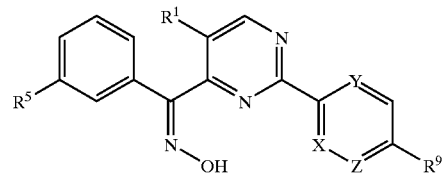

| R¹ | R⁵ | R⁹ | R¹ | R⁵ | R⁹ |
|---|---|---|---|---|---|
| X, Y and Z are CH ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X is N; Y and Z are CH ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X and Y are CH; Z is N ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |
| X and Y are N; Z is CH ||||||
| CH$_2$CH$_3$ | CF$_3$ | CF$_3$ | CH$_3$ | CF$_3$ | CF$_3$ |
| CH$_2$CH$_3$ | CF$_3$ | OCF$_3$ | CH$_3$ | CF$_3$ | OCF$_3$ |
| CH$_2$CH$_3$ | OCF$_3$ | CF$_3$ | CH$_3$ | OCF$_3$ | CF$_3$ |
| CH$_2$CH$_3$ | OCF$_3$ | OCF$_3$ | CH$_3$ | OCF$_3$ | OCF$_3$ |

TABLE 33-continued

Structure: phenyl(R⁵)-C(=N-OH)-pyrimidine(R¹)-pyrimidine/pyridine(X,Y,Z,R⁹)

| R¹ | R⁵ | R⁹ | R¹ | R⁵ | R⁹ |
|---|---|---|---|---|---|
| \multicolumn{6}{X is CH; Y and Z are N} |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| \multicolumn{6}{Y is CH; X and Z are N} |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| \multicolumn{6}{X, Y and Z are N} |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

TABLE 34

Structure: phenyl(R⁵)-CH(OH)-pyrimidine(R¹)-ring(X,Y,Z,R⁹)

| R¹ | R⁵ | R⁹ | R¹ | R⁵ | R⁹ |
|---|---|---|---|---|---|
| X, Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is N; Y and Z are CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are CH; Z is N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X and Y are N; Z is CH | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X is CH; Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| Y is CH; X and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |
| X, Y and Z are N | | | | | |
| CH₂CH₃ | CF₃ | CF₃ | CH₃ | CF₃ | CF₃ |
| CH₂CH₃ | CF₃ | OCF₃ | CH₃ | CF₃ | OCF₃ |
| CH₂CH₃ | OCF₃ | CF₃ | CH₃ | OCF₃ | CF₃ |
| CH₂CH₃ | OCF₃ | OCF₃ | CH₃ | OCF₃ | OCF₃ |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkings, et al., *Handbook of Insecticide Dust Diluents and Carriers,* 2nd Ed., Dorland Books, Caldwell, N.J. Typical liquid diluents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenze sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, silica, talc, diatomaceous earth, urea, calcium carbonate, sodium carbonate and bicarbonate, and sodium sulfate. Liquid diluents include, for example, water, N,N,-dimethylformamide, dimethyl sulfoxide, N-alkypyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example. U.S. Pat. No. 3,060,084. Granules and pellets can be prepared by spraying the active material upon preformed granular carriers or by agglomeration techniques. See Browing, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A.

Example A

High Strength Concentrate

| | |
|---|---|
| Compound 1 | 98.5% |
| silica aerogel | 0.5% |
| synthetic amorphous fine silica | 1.0%. |

Example B

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| Compound 1 | 10.0% |
| attapulgite granules (low volatile matter, 0.71/0.30 mm; U.S.S. No. 25–50 sieves) | 90.0%. |

Example D

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postmergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g. loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azafenidin, azimsulfuron, benazolin, benazolin-ethyl, benfluralin, benfuresate, bensulfuron-methyl, bensulide, bentazone, bifenox, bispyribac and its sodium salt, bromacil bromoxynil, bromoxynil octanoate, butachlor, butralin, butroxydim (ICIA0500), butylate, caloxydim (BAS 620H), carfentrazone-ethyl, chlomethoxyfen, chloramben, chlorbromuron, choridazon, chlorimuron-ethyl, chlornitrofen, chlorotoluron, chlorpropham, chlorsulfuron, chlorthal-dimethyl, cimmethylin, cinosulfuron, clethodim, clomazone, clopyralid, clopyralid-olamine, cyanazine, cycloate, cyslosulfamuron, 2,4-D and butotyl, butyl, isoctyl and isopropyl esters and its dimethylammonium, diolamine and trolamine salts, daimuroin, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methylethyl)-5-oxo-1H-imidazol-2-yl]-5-methyl-3-pyridine-carboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethoxysulfuron, fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentlyl, flumioxazin, fluometuron, fluroglycofen-ethyl, flupoxam, flupysulfuron-methyl and its sodium salt, fluridone, flurochloridone, fluroxypyr, fluthiacet-methyl, fomesafen, fosamine-ammonium, glufosinate, glufosinate-ammonium, glyphosate, glyphosate-isopropylammoinium, glyphosate-sesquisodium, glyphosate-trimesium, halosulfuron-methyl, haloxyfop-etotyl, haloxyfop-methyl, hexazinone, imazamethabenz-methyl, imazamox, imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole, lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy] acetate (AKH-7088), methyl 5-[[[[(4,6-dimethyl-2-pyrimidinyl)amino]carbonyl]amino]sulfonyl]-1-(2-pyridinyl)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosuilfron, norflurazon, oryzalin, oxadiazon, oxasulfuron, oxyfluorfen, paraquat dichloride, pebulate, pendimethalin, pentoxazone (KPP-314), perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyriminobac-methyl, pyrithiobac, pyrithiobac-sodium, quinclorac, quizalofop-ethyl, quizalofop-P-ethyl, quizalofop-P-tefuryl, rimsulfiiron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, triaziflam, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

The following Tests demonstrate the control efficacy of the compounds of this invention against specific weeds. The weed control afforded by the compounds is not limited, however, to these species. See Index Tables A–D for compound descriptions. The abbreviation "Ex." stands for "Example" and is followed by a number indicating in which example the compound is prepared.

INDEX TABLE A

| Cmpd | J | $R^1$ | $R^3$ | $R^4$ | A | mp (° C.) |
|---|---|---|---|---|---|---|
| 1 (Ex. 1) | 3-CF$_3$-phenyl | CH$_3$ | H | H | 4-CF$_3$-phenyl | 112–113 |
| 2 (Ex. 2) | 3-CF$_3$-phenyl | CH$_3$ | H | H | 3-CF$_3$-pyrazol-1-yl | 90–92* |

INDEX TABLE A-continued
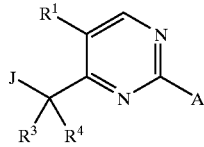
| Cmpd | J | R¹ | R³ | R⁴ | A | mp (° C.) |
|---|---|---|---|---|---|---|
| 3 | 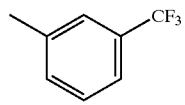 | H | H | H | 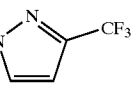 | oil* |
| 4 | 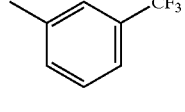 | CH₃ | H | H | 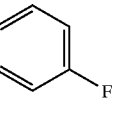 | 82–91 |
| 5 | 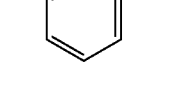 | CH₃ | H | H | 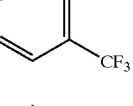 | 98–100 |
| 6 | 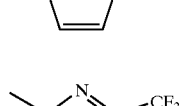 | CH₃ | H | H | 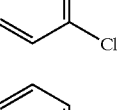 | 112–114 |
| 7 | 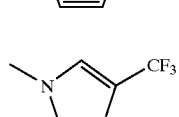 | CH₃ | H | H | 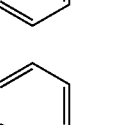 | 84–89 |
| 8 | 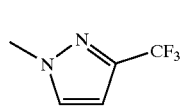 | CH₃ | H | H | 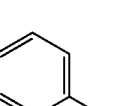 | solid* |
| 9 (Ex. 3) | 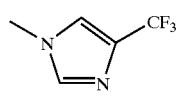 | CH₃ | H | H | 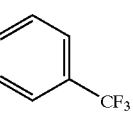 | 112–114 |
| 10 | 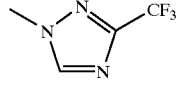 | CH₃ | H | H | 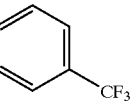 | 134–142 |
| 11 | 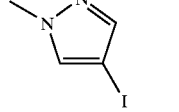 | CH₃ | H | H | 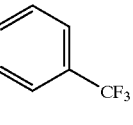 | 121–128 |
| 12 | 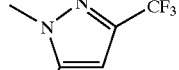 | CH₃ | H | H | 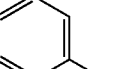 | 157–160 |
| 13 |  | CH₃ | H | H |  | 121–123 |

INDEX TABLE A-continued
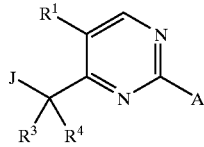
| Cmpd | J | R¹ | R³ | R⁴ | A | mp (° C.) |
|---|---|---|---|---|---|---|
| 14 | 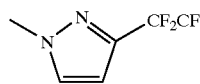 | CH₃ | H | H |  | 114–116 |
| 15 | 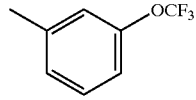 | CH₃ | H | H |  | 71–76 |
| 16 | 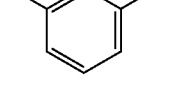 | CH₃ | H | H |  | 58–66 |
| 17 | 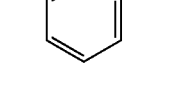 | CH₃ | CN | H |  | 156–157 |
| 18 | 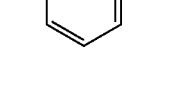 | CH₃ | COOCH₃ | H |  | 127–129 |
| 19 | 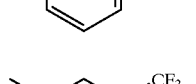 | CH₃ | CH₃ | H |  | 102–104 |
| 20 | 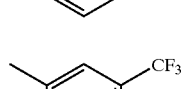 | CH₃ | H | OCH₃ |  | 78–82 |
| 21 | 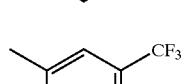 | CH₃ | Cl | H |  | 105–109 |
| 22 | 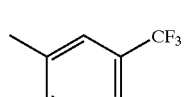 | CH₂CH₃ | H | H |  | 73–75 |
| 23 | 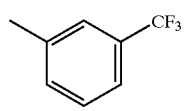 | OCH₃ | H | H |  | 92–93 |
| 24 |  | CH₃ | H | H |  | 65–67 |

INDEX TABLE A-continued

| Cmpd | J | R¹ | R³ | R⁴ | A | mp (° C.) |
|---|---|---|---|---|---|---|
| 25 | 3-CF₃-C₆H₄ | CH₃ | H | H | 3-Cl-4-F-C₆H₃ | 72–74 |
| 26 | 3-CF₃-C₆H₄ | CH₃ | H | H | 2-F-C₆H₄ | 58–60 |
| 27 | 3-CF₃-C₆H₄ | CH₃ | H | H | 3,4-Cl₂-C₆H₃ | 75–77 |
| 28 | 3-CF₃-C₆H₄ | CH₃ | H | H | 4-Cl-C₆H₄ | 93–95 |
| 29 | 3-CF₃-C₆H₄ | CH₃ | H | H | 2-F-4-Cl-C₆H₃ | 78–80 |
| 30 | 3-CF₃-C₆H₄ | CH₃ | H | H | 4-CN-C₆H₄ | 128–132 |
| 31 | 3-CF₃-C₆H₄ | CH₃ | H | H | 2,4-F₂-C₆H₃ | 48–50 |
| 32 | 3-CN-C₆H₄ | CH₃ | H | H | 4-CF₃-C₆H₄ | 152–154 |
| 33 | 3-CN-C₆H₄ | CH₃ | H | H | 4-Cl-C₆H₄ | 150–152 |
| 34 | 3-CN-C₆H₄ | CH₃ | H | H | 2,4-F₂-C₆H₃ | 145–146 |
| 35 | 3-CN-C₆H₄ | CH₃ | H | H | 2-F-4-Cl-C₆H₃ | 137–138 |

INDEX TABLE A-continued
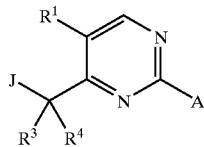
| Cmpd | J | R¹ | R³ | R⁴ | A | mp (° C.) |
|---|---|---|---|---|---|---|
| 36 | 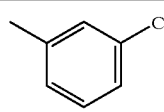 | CH₃ | H | H | 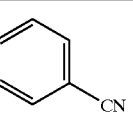 | 164 |
| 37 | 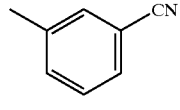 | CH₃ | H | H | 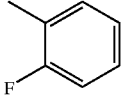 | 114–115 |
| 38 | 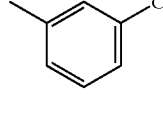 | CH₃ | H | H | 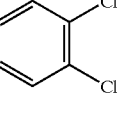 | 134–136 |
| 39 | 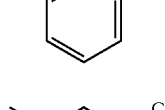 | CH₃ | H | H | 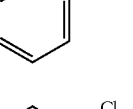 | 131–132 |
| 40 | 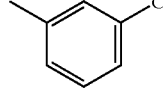 | CH₃ | H | H | 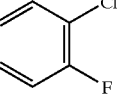 | 135–138 |
| 41 | 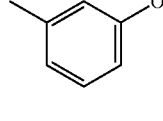 | CH₂CH₃ | H | H | 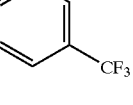 | 59–61 |
| 42 | 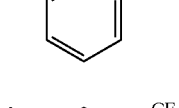 | CH₃ | H | H | 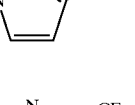 | 72–74 |
| 43 | 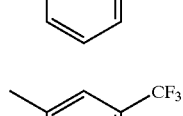 | CH₃ | H | H | 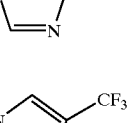 | 103–104 |
| 44 | 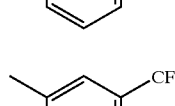 | CH₃ | H | H | 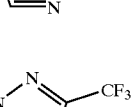 | 89–94 |
| 45 | 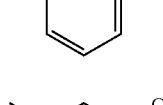 | OCH₃ | H | H | 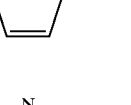 | 80–85 |
| 46 | 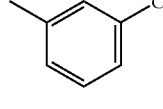 | CH₂CH₃ | H | H | 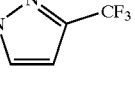 | 76–77 |

INDEX TABLE A-continued

| Cmpd | J | R¹ | R³ | R⁴ | A | mp (° C.) |
|---|---|---|---|---|---|---|
| 47 | 3-(OCF₃)phenyl | CH₂CH₃ | H | H | 1-methyl-3-(CF₃)pyrazol-5-yl | oil* |
| 48 | 3-(OCF₃)phenyl | CH₂CH₂CH₃ | H | H | 1-methyl-3-(CF₃)pyrazol-5-yl | |
| 49 | 3-(OCF₃)phenyl | CH₂CH₃ | H | H | 1-methyl-4-(CF₃)imidazol-2-yl | oil* |
| 50 | 3-(OCF₃)phenyl | CH₂CH₃ | H | H | 1-methyl-3-(CF₃)-1,2,4-triazol-5-yl | oil* |
| 51 | 1-methyl-3-(CF₃)pyrazol-5-yl | CH₃ | H | H | 1-methyl-3-(CF₃)-1,2,4-triazol-5-yl | 104–106 |
| 52 | 1-methyl-3-(CF₃)pyrazol-5-yl | CH₃ | H | H | 1-methyl-3-(CF₃)pyrazol-5-yl | 93–97 |
| 53 | 1-methyl-3-(CN)pyrazol-5-yl | CH₃ | H | H | 4-(CF₃)phenyl | 150–152 |
| 54 | 1-methyl-4-Br-pyrazol-5-yl | CH₃ | H | H | 4-(CF₃)phenyl | 139–141 |
| 55 | 3-(CF₃)phenyl | CH₃ | H | H | 1-methyl-3-(CF₃)pyrazol-5-yl | 100–102 |
| 56 | 3-(CF₃)phenyl | CH₂CH₂CH₃ | H | H | 4-(CF₃)phenyl | 81–84 |
| 57 | 3-(OCF₃)phenyl | CH₂CH₂CH₃ | H | H | 4-(CF₃)phenyl | 63–65 |

INDEX TABLE A-continued

Structure: pyrimidine with R¹ at 5-position, at 4-position a carbon bearing J, R³, R⁴; at 2-position A.

| Cmpd | J | R¹ | R³ | R⁴ | A | mp (° C.) |
|---|---|---|---|---|---|---|
| 58 | 3-(CF₃)phenyl-CH₂ | CH₂CH₂CH₃ | H | H | 1-methyl-3-(CF₃)pyrazol-5-yl | oil* |

*See Index Table B for ¹H NMR data.

INDEX TABLE B

| Cmpd No. | ¹H NMR Data (CDCl₃ solution unless indicated otherwise)[a] |
|---|---|
| 2 | δ 8.55(t,2H), 7.55–7.50(m,2H), 7.45–7.40(m,2H), 6.72(d,1H), 4.26(s,2H), 2.32(s,3H). |
| 3 | δ 8.70(d,1H), 8.65(d,1H), 7.60–7.55(m,2H), 7.50–7.45(m,2H), 7.05(d,1H), 6.75(d,1H), 4.28(s,2H). |
| 8 | δ 8.62(s,1H), 8.27(m,2H), 7.7(s,1H), 7.47(m,3H), 7.4(s,1H), 5.28(s,2H), 2.36(s,3H). |
| 47 | δ 8.59(m,2H), 7.40–7.10(m,4H), 6.71(d,1H), 4.24(s,2H), 2.70(q,2H), 1.20(t,3H). |
| 48 | δ 8.56(s,2H), 7.34(t,1H), 7.15(m,3H), 6.72(m,1H), 4.24(s,2H), 2.65(t,2H), 1.57(m,2H), 0.98(t,3H). |
| 49 | δ 8.65(s,1H), 8.47(s,1H), 8.17(s,1H), 7.40–7.15(m,4H), 4.20(s,2H), 2.70(q,2H), 1.25(t,3H). |
| 50 | δ 9.20(s,1H), 8.60(s,1H), 7.41(t,1H), 7.15(m,3H), 4.25(s,2H), 2.80(q,2H), 1.24(t,3H.). |
| 58 | δ 8.57(s,1H), 8.54(m,1H), 7.53(m,2H), 7.43(m,2H), 6.71(d,1H), 4.28(s,2H), 2.65(t,2H), 1.61(m,2H), 0.98(t,3H). |

INDEX TABLE C

Structure: pyrimidine with R¹ at 5-position, at 4-position a C(=O) bearing J; at 2-position A.

| Cmpd | J | R¹ | A | mp (° C.) |
|---|---|---|---|---|
| 59 (Ex. 4) | 3-(CF₃)phenyl-CH₂ | CH₃ | 1-methyl-3-(CF₃)pyrazol-5-yl | 113–116 |
| 60 | 3-(CF₃)phenyl-CH₂ | OCH₃ | 1-methyl-3-(CF₃)pyrazol-5-yl | 183–185 |
| 61 | 3-(CF₃)phenyl-CH₂ | CH₃ | 1-methyl-4-(CF₃)imidazol-5-yl | 80–82 |

INDEX TABLE C-continued

| Cmpd | J | R¹ | A | mp (° C.) |
|---|---|---|---|---|
| 62 | 3-(OCF₃)phenyl | CH₃ | 1-methyl-3-(CF₂CF₃)pyrazol-5-yl | 85–87 |
| 63 | 3-(OCF₃)phenyl | CH₃ | 1-methyl-4-(CF₃)imidazol-5-yl | oil* |
| 64 | 3-(OCF₃)phenyl | CH₃ | 1-methyl-3-(CF₃)-1,2,4-triazol-5-yl | 120–123 |
| 65 | 4-(CF₃)phenyl | CH₃ | 1-methyl-3-(CF₃)pyrazol-5-yl | 144–146 |
| 66 | 3-(OCF₃)phenyl | CH₃ | 1-methyl-3-(CF₃)pyrazol-5-yl | 85–88 |
| 67 | 3-(CF₃)phenyl | CH₃ | 1-methyl-3-(CF₃)-1,2,4-triazol-5-yl | oil* |
| 68 | 3-(CF₃)phenyl | CH₃ | 1-methyl-3-(CF₂CF₃)pyrazol-5-yl | 79–85 |
| 69 | 3-(CF₃)phenyl | CH₂CH₃ | 1-methyl-3-(CF₃)pyrazol-5-yl | 95–99 |
| 70 | 3-(CF₃)phenyl | H | 1-methyl-3-(CF₃)pyrazol-5-yl | oil* |
| 71 | 3-(OCF₃)phenyl | CH₂CH₃ | 1-methyl-4-(CF₃)imidazol-5-yl | oil* |

INDEX TABLE C-continued

Structure: pyrimidine with R¹ at 5-position, J-C(=O)- at 4-position, A at 2-position

| Cmpd | J | R¹ | A | mp (° C.) |
|---|---|---|---|---|
| 72 | 3-CN-phenyl | CH₂CH₃ | 1-(3-CF₃-pyrazolyl) | 150–153 |
| 73 (Ex. 5) | 3-CF₃-phenyl | CH₃ | 4-CF₃-phenyl | 159–161 |
| 74 | 4-CF₃-phenyl | CH₃ | 4-CF₃-phenyl | 155–157 |
| 75 | 3-OCF₃-phenyl | CH₃ | 4-CF₃-phenyl | 122–123 |
| 76 | 3-CF₃-phenyl | H | 2,4-difluorophenyl | 62–64 |
| 77 | 3-CF₃-phenyl | H | 4-CF₃-phenyl | 96–100 |
| 78 | 3-CF₃-phenyl | H | 4-CN-phenyl | 122–124 |

*See Index Table D for ¹H NMR data.

INDEX TABLE D

| Cmpd No. | ¹H NMR Data (CDCl₃ solution unless indicated otherwise)[a] |
|---|---|
| 63 | δ 8.77(s,1H), 8.57(s,1H), 8.17(s,1H), 7.77–7.85(m,2H), 7.50–7.60(m,2H), 2.42(s,3H). |
| 67 | δ (s,1H), 8.93(s,1H), 8.25(s,1H), 8.07(d,1H), 7.97(d,1H), 7.68(m,1H), 2.48(s,3H). |
| 70 | δ 9.13(d,1H), 8.60(m,2H), 8.42(d,1H), 7.91(m,2H), 7.72(t,1H), 6.70(d,1H). |
| 71 | δ 8.81(s,1H), 8.58(s,1H), 8.18(s,1H), 7.81(s,1H), 7.77(m,1H), 7.57(m,2H), 2.77(q,2H), 1.28(t,3H). |

[a] ¹H NMR data are in ppm downfield from tetramethylsilane. Couplings are designated by (s)-singlet, (d)-doublet, (t)-triplet, (q)-quartet, (m)-multiplet, (dd)-doublet of doublets, (dt)-doublet of triplets, (br s)-broad singlet.

Biological Examples of the Invention

Test A

Seeds of barnyardgrass (*Echinochloa crus-galli*), crabgrass (*Digitaria* spp.), morningglory (*Ipomoea* spp.), and velvetleaf (*Abutilon theophrasti*) were planted into a sandy loam soil and treated preemergence by soil drench with test chemicals formulated in a non-phytotoxic solvent mixture which includes a surfactant. At the same time, these crop and weed species were also treated postemergence sprayed to runoff, with test chemicals formulated in the same manner.

Plants ranged in height from two to eighteen cm and were in the one to two leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (–) response means no test results.

TABLE A

| PRE SOIL DRENCH | COMPOUND | | | | | | | | | |
|---|---|---|---|---|---|---|---|---|---|---|
| | Rate 2000 g/ha | | | | | | | | | Rate 1000 g/ha |
| | 1 | 6 | 8 | 12 | 13 | 59 | 65 | 73 | 74 | 8 |
| Barnyardgrass | 10 | 8 | 7 | 7 | 9 | 10 | 5 | 9 | 1 | 4 |
| Crabgrass | 10 | 9 | 10 | 9 | 10 | 10 | 8 | 10 | 7 | 9 |
| Morningglory | 8 | 5 | 8 | 3 | 3 | 9 | 4 | 9 | 1 | 9 |
| Velvetleaf | 9 | 8 | 3 | 5 | 9 | 10 | 4 | 9 | 4 | 2 |

| SPRAYED TO RUNOFF | COMPOUND | | | | | | | | | |
|---|---|---|---|---|---|---|---|---|---|---|
| | Rate 1000 g/ha | | | | | | | | | Rate 500 g/ha |
| | 1 | 6 | 8 | 12 | 13 | 59 | 65 | 73 | 74 | 8 |
| Barnyardgrass | 9 | 8 | 3 | 5 | 6 | 9 | 4 | 8 | 5 | 3 |
| Crabgrass | 9 | 9 | 5 | 8 | 9 | 9 | 5 | 9 | 8 | 8 |
| Morningglory | 9 | 6 | 7 | 2 | 2 | 8 | 10 | 9 | 10 | 3 |
| Velvetleaf | 9 | 9 | 2 | 6 | 8 | 9 | 5 | 9 | 5 | 1 |

Test B

Seeds of bedstraw (*Galium aparine*), blackgrass (*Alopecurus myosuroides*), broadleaf signalgrass (*Brachiaria decumbens*), cocklebur (*Xanthium strumarium*), corn (*Zea mays*), crabgrass (*Digitaria sanguinalis*), giant foxtail (*Setaria faberii*), lambsquarters (*Chenopodium album*), morningglory (*Ipomoea hederacea*), pigweed (*Amaranthus retroflexus*), rape (*Brassica napus*), soybean (*Glycine max*), sugar beet (*Beta vulgaris*), velvetleaf (*Abutilon theophrasti*), wheat (*Triticum aestivum*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from 2 to 18 cm (1- to 4-leaf stage) for postemergence treatments. Plant species in the flood test consisted of rice (*Oryza sativa*), smallflower flatsedge (*Cyperus difformis*), duck salad (*Heteranthera limosa*) and barnyardgrass (*Echinochloa crus-galli*) grown to the 2-leaf stage for testing. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (–) response means no test result.

TABLE B

| Rate 500 g/ha | | | | | | | | | | | | | | | | COMPOUND | | | | | | | | | | | |
|---|---|---|---|---|---|---|---|---|---|---|---|---|---|---|---|---|---|---|---|---|---|---|---|---|---|---|---|
| Postemergence | 1 | 2 | 3 | 4 | 5 | 6 | 7 | 9 | 10 | 11 | 12 | 13 | 14 | 16 | 32 | 52 | 53 | 54 | 59 | 61 | 62 | 63 | 64 | 65 | 66 | 67 | 68 | 73 | 74 |
| B. signalgrass | 9 | — | 3 | 3 | 5 | — | 1 | 9 | 3 | 7 | 7 | 8 | 4 | 1 | 9 | 9 | 2 | 5 | 3 | 5 | 3 | 5 | 8 | 1 | 5 | 9 | 5 | 8 | 2 |
| Barnyardgrass | — | 6 | 6 | 8 | 3 | 3 | 2 | 8 | 4 | — | 3 | 3 | 6 | 4 | 4 | 8 | 2 | 4 | 8 | 4 | 4 | 3 | 5 | 0 | 4 | 6 | 4 | 4 | 0 |
| Bedstraw | 10 | 9 | 9 | 9 | 9 | 8 | 3 | 10 | 10 | 10 | 10 | 10 | 10 | 5 | — | 10 | 10 | 9 | 9 | 9 | 4 | 8 | 9 | 7 | 8 | 10 | 10 | 9 | 6 |
| Blackgrass | 9 | 9 | 3 | 7 | 5 | 2 | 1 | 9 | 3 | 5 | 4 | 5 | 3 | 6 | — | 9 | 6 | 3 | 6 | 8 | 4 | 6 | 9 | 0 | 6 | 10 | 5 | 9 | 1 |
| Cocklebur | 10 | 9 | 6 | — | 8 | 7 | — | 9 | 9 | 9 | 8 | 9 | 7 | 3 | — | 9 | 6 | 9 | 8 | 8 | 7 | 8 | 8 | 2 | 5 | 10 | 7 | 8 | 5 |
| Corn | 7 | 7 | 3 | 4 | 4 | 3 | 2 | 5 | 3 | 3 | 3 | 4 | 3 | 1 | — | 7 | 1 | 5 | 4 | 4 | 2 | 2 | 2 | 0 | 1 | 3 | 2 | 3 | 1 |
| Crabgrass | 9 | 10 | 3 | 9 | 8 | 9 | 2 | 10 | 6 | — | 2 | 9 | 4 | 7 | — | 9 | 4 | 3 | 9 | 9 | 4 | 6 | 6 | 9 | 3 | 7 | 10 | 9 | 3 |
| Ducksalad | — | 2 | 6 | 5 | 2 | 6 | 2 | 6 | 5 | 7 | 2 | 3 | 3 | 2 | 6 | 9 | 7 | 3 | 7 | 5 | 8 | 6 | 2 | 5 | 1 | 10 | 8 | 3 | 3 |
| Giant foxtail | 9 | 10 | 5 | 8 | 6 | 1 | 2 | 9 | 6 | — | 4 | 5 | 3 | 2 | — | 9 | 2 | 4 | 9 | 5 | 2 | 3 | 3 | 5 | 0 | 4 | 9 | 3 | 0 |
| Morningglory | 10 | 9 | 8 | 9 | 4 | 8 | 5 | 10 | 9 | 9 | 9 | 9 | 8 | 1 | — | 10 | 2 | 4 | 9 | 9 | 3 | 3 | 3 | 8 | 1 | 4 | 10 | 3 | 1 |
| Nutsedge | 2 | 2 | 0 | 0 | 0 | 3 | 0 | 3 | 3 | — | 0 | 0 | 0 | 1 | — | 3 | 3 | 10 | 0 | — | 10 | 10 | 10 | 8 | 10 | 10 | 10 | 10 | 7 |
| Rape | 9 | 10 | 7 | 10 | 10 | 9 | 7 | 10 | 9 | 10 | 9 | 9 | 7 | 5 | — | 10 | 9 | 9 | 7 | 9 | 3 | 8 | 8 | 4 | 7 | 10 | 7 | — | 3 |
| Redroot pigweed | 10 | 9 | 9 | 10 | 9 | 9 | 7 | 10 | 9 | 10 | 9 | 10 | 9 | 5 | — | 10 | 7 | 7 | 9 | 9 | 10 | 9 | 9 | 10 | 7 | 10 | 10 | 10 | 8 |
| Rice | — | 6 | 6 | 7 | 3 | 3 | 4 | 8 | 3 | — | 3 | 1 | 5 | 4 | 2 | 7 | 2 | 4 | 4 | 9 | 2 | 0 | 1 | 3 | 0 | 2 | 4 | 3 | 0 |
| S. Flatsedge | — | 9 | 9 | 8 | 5 | 7 | 4 | 10 | 9 | — | 8 | 5 | 9 | 3 | 7 | 9 | 9 | 4 | 9 | 6 | 8 | 8 | 9 | 9 | 7 | 9 | 9 | 6 | 3 |
| Soybean | 9 | 8 | 8 | 8 | 6 | 6 | 5 | 9 | 8 | 9 | 5 | 5 | 5 | 4 | — | 9 | 7 | 9 | 9 | 9 | 2 | 2 | 2 | 6 | 2 | 7 | 9 | 8 | 3 |
| Sugarbeets | 10 | 9 | 9 | 10 | 10 | 9 | 8 | 10 | 9 | 10 | 9 | 10 | 9 | 9 | — | 10 | 10 | 9 | 9 | 10 | 8 | 9 | 9 | 10 | 8 | 10 | 9 | 9 | 7 |
| Velvetleaf | 10 | 9 | 4 | 10 | 9 | 8 | 8 | 9 | 9 | 9 | 8 | 8 | 4 | 2 | — | 9 | 7 | 3 | 8 | 8 | 3 | 8 | 8 | 9 | 5 | 8 | 8 | 10 | 2 |
| Wheat | 5 | 5 | 3 | 2 | 4 | 3 | 0 | 6 | 3 | 3 | 4 | 4 | 3 | 1 | — | 8 | 2 | 2 | 3 | 4 | 3 | 3 | 2 | 5 | 2 | 3 | 6 | 6 | 2 |
| Wild oats | 9 | 7 | 3 | 3 | 5 | 3 | 0 | 8 | 3 | 5 | 5 | 4 | 3 | 1 | — | 9 | 2 | 3 | 6 | 5 | 3 | 2 | 2 | 7 | 1 | 3 | 8 | 9 | 1 |

| Rate 500 g/ha | | | | | | | | | | | | | | | | COMPOUND | | | | | | | | | | | |
|---|---|---|---|---|---|---|---|---|---|---|---|---|---|---|---|---|---|---|---|---|---|---|---|---|---|---|---|
| Preemergence | 1 | 2 | 3 | 4 | 5 | 6 | 7 | 9 | 10 | 11 | 12 | 13 | 14 | 16 | 52 | 53 | 54 | 59 | 61 | 62 | 63 | 64 | 65 | 66 | 67 | 68 | 73 | 74 | 75 |
| B. signalgrass | 9 | 9 | 5 | — | 9 | 9 | 0 | 10 | 4 | 8 | 9 | 9 | 5 | 7 | 6 | 6 | 5 | 9 | 9 | 9 | 9 | 10 | 2 | 10 | 10 | 10 | 10 | 0 | 9 |
| Bedstraw | 9 | 10 | 5 | 8 | 7 | 5 | 0 | 9 | 10 | 9 | 8 | 6 | 2 | 1 | 10 | 8 | 4 | 8 | 6 | 8 | 9 | 9 | 0 | 8 | 10 | 6 | 10 | 0 | 8 |
| Blackgrass | 10 | 10 | 10 | 10 | 7 | 4 | 0 | 10 | 10 | 5 | 6 | 9 | 3 | 4 | 10 | 2 | 4 | 9 | 8 | 5 | 9 | 9 | 0 | 10 | 9 | 7 | 10 | 0 | 10 |
| Cocklebur | 10 | 3 | 0 | 1 | — | 0 | 0 | 9 | 3 | — | 3 | 7 | — | 0 | 10 | 1 | 0 | 2 | 0 | 1 | 7 | 7 | 0 | 3 | 5 | 8 | — | — | 9 |
| Corn | 2 | 2 | 1 | 2 | 1 | 0 | 0 | 4 | 1 | 0 | 2 | 2 | 3 | 0 | 8 | 0 | 1 | 3 | 2 | 2 | 4 | 0 | 0 | 3 | 7 | — | 2 | 0 | 2 |
| Crabgrass | 10 | 10 | 5 | 10 | 9 | 9 | 2 | 10 | 9 | 10 | 10 | 10 | 3 | 8 | 10 | 8 | 10 | 10 | 10 | 9 | 10 | 10 | 5 | 9 | 10 | 10 | 10 | 1 | 10 |
| Giant foxtail | 10 | 10 | 10 | 10 | 10 | 10 | 5 | 10 | 9 | 10 | 9 | 10 | 8 | 8 | 10 | 10 | 2 | 10 | 10 | 4 | 10 | 6 | 0 | 4 | 10 | 10 | 10 | 0 | 10 |
| Morningglory | 10 | 10 | 10 | 8 | 9 | 10 | 0 | 10 | 0 | 10 | 10 | 10 | 0 | 1 | 10 | 5 | 2 | 10 | 7 | 10 | 10 | 10 | 5 | 4 | 10 | 9 | 10 | 1 | 10 |
| Nutsedge | 1 | 0 | 5 | 0 | 1 | 2 | 0 | 0 | 0 | 0 | 0 | 0 | 0 | 1 | 1 | 2 | 7 | 0 | 10 | 3 | 2 | 10 | 0 | 9 | 10 | 0 | 0 | 0 | 4 |
| Rape | 10 | 10 | 7 | 9 | 10 | 7 | 2 | 10 | 7 | 10 | 6 | 9 | 8 | 8 | 10 | 7 | 3 | 10 | 10 | 8 | 10 | 10 | 0 | 10 | 10 | 8 | 10 | 0 | 10 |
| Redroot pigweed | 10 | 10 | 10 | 10 | 10 | 6 | 0 | 10 | 10 | 2 | 9 | 10 | 4 | 9 | 10 | 8 | 9 | 10 | 10 | 10 | 10 | 10 | 1 | 10 | 10 | 10 | 10 | 0 | 10 |
| Soybean | 5 | 5 | 2 | 3 | 3 | 3 | 1 | 10 | 3 | 2 | 3 | 3 | 1 | 4 | 9 | 0 | 0 | 4 | 2 | 0 | 1 | 0 | 0 | 1 | 8 | 10 | 2 | 0 | 4 |
| Sugarbeets | 10 | 10 | 10 | 10 | 10 | 10 | 0 | 10 | 10 | 10 | 10 | 10 | 9 | 8 | 10 | 9 | 9 | 10 | 10 | 10 | 10 | 10 | 0 | 8 | 10 | 10 | 10 | 2 | 10 |
| Velvetleaf | 10 | 10 | 6 | 7 | 9 | 3 | 1 | 9 | 8 | 3 | 4 | 10 | 7 | 1 | 10 | 8 | 1 | 10 | 7 | 0 | 10 | 8 | 1 | 8 | 10 | 8 | 8 | 0 | 10 |
| Wheat | 9 | 3 | 0 | 5 | 3 | 0 | 0 | 6 | 6 | 3 | 4 | 1 | 0 | 0 | 6 | 1 | 1 | 5 | 4 | 4 | 2 | 0 | 0 | 3 | 4 | 4 | 9 | 0 | 5 |
| Wild oats | 10 | 10 | 9 | 9 | 8 | 3 | 0 | 8 | 9 | 6 | 4 | 9 | 2 | 3 | 10 | 4 | 4 | 9 | 8 | 8 | 9 | 9 | 0 | 5 | 8 | 10 | 10 | 0 | 9 |

| Rate 250 g/ha | | | | | | | | | | | | | | COMPOUND | | | | | | |
|---|---|---|---|---|---|---|---|---|---|---|---|---|---|---|---|---|---|---|---|---|
| Postemergence | 1 | 2 | 3 | 7 | 9 | 10 | 11 | 12 | 13 | 14 | 15 | 16 | 17 | 18 | 19 | 20 | 21 | 22 | 23 | 24 | 25 |
| B. signalgrass | 8 | — | 3 | 6 | 1 | 3 | 4 | 7 | 7 | 7 | 8 | 1 | 7 | 3 | 2 | 3 | 7 | 7 | 9 | 3 | 3 |

TABLE B-continued

| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 49 | 50 |
|---|---|---|---|---|---|---|---|---|---|---|---|---|---|---|---|---|---|---|---|---|---|---|---|---|
| Barnyardgrass | — | 5 | 6 | 8 | 3 | 2 | 1 | 7 | 3 | — | 3 | 3 | 5 | 9 | 4 | 6 | 2 | 3 | 0 | 4 | 6 | 6 | 4 | 5 |
| Bedstraw | 9 | 9 | 8 | 9 | 9 | 7 | 3 | 10 | 10 | 10 | 10 | 10 | 8 | 9 | 4 | 9 | 9 | 3 | 4 | 9 | 8 | 9 | 10 | 10 |
| Blackgrass | 9 | 7 | 3 | 6 | 5 | 2 | — | 8 | 3 | 7 | 4 | 5 | 3 | 9 | 2 | 7 | 2 | 1 | 3 | 6 | 9 | 9 | 4 | 8 |
| Cocklebur | 8 | 8 | 5 | 7 | 8 | 7 | — | 10 | 9 | 9 | 8 | 9 | 7 | 10 | 5 | 8 | 8 | 3 | 7 | 8 | 8 | 8 | 10 | 9 |
| Corn | 4 | 6 | 3 | 3 | 2 | 3 | 2 | 5 | 3 | 3 | 3 | 3 | 2 | 5 | 1 | 3 | 4 | 2 | 3 | 4 | 4 | 4 | 10 | 3 |
| Crabgrass | 9 | 9 | 9 | 9 | 4 | 8 | 3 | 10 | 4 | 4 | 3 | 7 | 2 | 9 | 2 | 5 | 3 | 3 | 3 | 8 | 9 | 3 | 1 | 6 |
| Ducksalad | — | 2 | 3 | 2 | 1 | 2 | 2 | 5 | 6 | 6 | 1 | 2 | 2 | 2 | 1 | 1 | 2 | 2 | 0 | 5 | 6 | 6 | 8 | 10 |
| Giant foxtail | 9 | 9 | 3 | 7 | 4 | 0 | 0 | 10 | 8 | — | 3 | 4 | 2 | 7 | 2 | 5 | 1 | 7 | 3 | 9 | 8 | 8 | 3 | 6 |
| Morningglory | 10 | 9 | 7 | 8 | 3 | 5 | 1 | 9 | 4 | 5 | 1 | 9 | 1 | 8 | 1 | 8 | 5 | 1 | 6 | 9 | 8 | 9 | 3 | 8 |
| Nutsedge | 1 | — | 0 | 0 | 0 | 8 | 2 | 10 | 7 | 10 | 3 | 9 | 6 | 2 | 0 | 1 | 0 | 6 | 4 | 9 | 10 | 9 | 10 | 10 |
| Rape | 9 | 9 | 6 | 10 | 10 | 9 | 0 | 10 | 9 | 10 | 9 | 9 | 6 | 9 | 2 | 8 | 0 | 0 | 3 | 9 | 10 | 10 | 10 | 10 |
| Redroot pigweed | 10 | 9 | 9 | 10 | 9 | 8 | 6 | 10 | 9 | 10 | 9 | 10 | 9 | 7 | 8 | 10 | 9 | 3 | 5 | 10 | 10 | 10 | 10 | 5 |
| Rice | — | 5 | 4 | 6 | 2 | 5 | 7 | 7 | 2 | — | 3 | 0 | 5 | 7 | 3 | 6 | 5 | 7 | 8 | 5 | 5 | 5 | 3 | 7 |
| S. Flatsedge | — | 8 | 9 | 7 | 5 | 5 | 0 | 9 | 9 | — | 8 | 4 | 5 | 9 | 2 | 8 | 2 | 2 | 0 | 9 | 9 | 9 | 6 | 7 |
| Soybean | 9 | 8 | 7 | 8 | 5 | 7 | 2 | 10 | 8 | 8 | 5 | 5 | 8 | 9 | 4 | 4 | 6 | 6 | 6 | 6 | 8 | 8 | 10 | 10 |
| Sugarbeets | 10 | 9 | 9 | 9 | 10 | 6 | 3 | 10 | 9 | 10 | 8 | 10 | 4 | 10 | 9 | 10 | 9 | 9 | 7 | 10 | 10 | 10 | 10 | 9 |
| Velvetleaf | 9 | 9 | 3 | 8 | 7 | 8 | 8 | 10 | 8 | 8 | 8 | 8 | 8 | 8 | 2 | 7 | 7 | 2 | 7 | 9 | 9 | 9 | 5 | 4 |
| Wheat | 3 | 3 | 2 | 2 | 3 | 4 | 1 | 4 | 3 | 3 | 3 | 3 | 4 | 6 | 0 | 8 | 4 | 0 | 2 | 5 | 6 | 6 | 3 | 4 |
| Wild oats | 7 | 6 | 2 | 3 | 4 | 3 | 0 | 6 | 2 | 3 | 4 | 4 | 3 | 9 | 1 | 5 | 5 | 2 | 3 | 6 | 8 | 9 | 4 | 4 |

Rate 250 g/ha

Postemergence

COMPOUND

| | 51 | 52 | 53 | 54 | 59 | 60 | 61 | 62 | 63 | 64 | 65 | 66 | 67 | 68 | 70 | 71 | 72 | 73 | 74 | 75 | 76 | 77 | 78 |
|---|---|---|---|---|---|---|---|---|---|---|---|---|---|---|---|---|---|---|---|---|---|---|---|
| B. signalgrass | 2 | 5 | 9 | 4 | 2 | 3 | 4 | 2 | 4 | 6 | 1 | 4 | 7 | 3 | 1 | — | 6 | 6 | 5 | 0 | 5 | 8 | 2 |
| Barnyardgrass | 2 | 3 | 5 | 2 | 4 | 2 | 2 | 3 | 3 | 4 | 0 | 4 | 5 | 4 | 0 | 3 | 6 | 5 | 4 | 4 | 4 | 6 | 4 |
| Bedstraw | 6 | 9 | 10 | 9 | 6 | 3 | 9 | 3 | 5 | 7 | 7 | 6 | 10 | 9 | 1 | — | 4 | 9 | 9 | 9 | 10 | — | — |
| Blackgrass | 1 | 5 | 3 | 5 | 1 | 3 | — | 9 | 7 | 8 | 2 | 3 | — | 4 | 2 | 6 | — | 10 | 9 | 0 | 6 | 6 | 8 |
| Cocklebur | 3 | 9 | 8 | 9 | 8 | 8 | 5 | 2 | 6 | 1 | 2 | 1 | 0 | 1 | 5 | 8 | 7 | 8 | 7 | 0 | 9 | 8 | 7 |
| Corn | 1 | 5 | 8 | 5 | 2 | 3 | 9 | 2 | 8 | 2 | 3 | 3 | 3 | 5 | 2 | 9 | 9 | 9 | 9 | 0 | 6 | 4 | 2 |
| Crabgrass | 1 | 3 | 8 | 3 | 8 | 8 | 2 | 6 | 1 | 1 | 2 | 1 | 1 | 1 | 5 | 3 | 8 | 5 | 5 | 0 | 3 | 4 | 6 |
| Ducksalad | 6 | 6 | 4 | 9 | 2 | 7 | 6 | 1 | 1 | 2 | 1 | 1 | 1 | 0 | 1 | 10 | 8 | 10 | 10 | 0 | 8 | 10 | 8 |
| Giant foxtail | 0 | 2 | 10 | 4 | 5 | 6 | 4 | 2 | 1 | 1 | 2 | 1 | 0 | 1 | 3 | 5 | 9 | 9 | 9 | 0 | 4 | 7 | 10 |
| Morningglory | 1 | 4 | 6 | 4 | 2 | 3 | 2 | 1 | 1 | 2 | 1 | 1 | 1 | 0 | 7 | 9 | 9 | 9 | 9 | 0 | 7 | 7 | 2 |
| Nutsedge | 3 | 8 | 9 | 10 | 9 | 4 | 10 | 5 | 0 | 1 | 2 | 2 | 0 | 1 | 2 | 8 | 9 | 10 | 9 | 0 | 10 | 8 | 6 |
| Rape | — | — | 3 | — | 2 | — | 1 | 0 | 0 | 0 | 0 | 1 | 1 | 0 | — | — | 2 | 3 | 3 | — | — | — | 2 |
| Redroot pigweed | 6 | 9 | 10 | 9 | 10 | 9 | 8 | 7 | 3 | 9 | 5 | 4 | 4 | 4 | 8 | 10 | 10 | 10 | 10 | 0 | 9 | 10 | 10 |
| Rice | 8 | 10 | 10 | 10 | 9 | 9 | 9 | 7 | 6 | 5 | 8 | 0 | 7 | 3 | 6 | 6 | 9 | 7 | 7 | 0 | 10 | 9 | 9 |
| S. Flatsedge | 0 | 1 | 3 | 3 | 2 | 3 | 9 | 3 | 1 | 1 | 1 | 0 | 5 | 0 | 2 | 2 | 9 | 9 | 7 | 0 | 4 | 6 | 4 |
| Soybean | 2 | 5 | 8 | 8 | 8 | 8 | 6 | 3 | 3 | 2 | 6 | 0 | 0 | 2 | 5 | 5 | 9 | 9 | 6 | 0 | 7 | 7 | 9 |
| Sugarbeets | 5 | 7 | 7 | 7 | 6 | 6 | 6 | 8 | 3 | 2 | 0 | 0 | 4 | 1 | 2 | 7 | 9 | 9 | 9 | 0 | 9 | 7 | 7 |
| Velvetleaf | 8 | 10 | 10 | 10 | 10 | 10 | 10 | 10 | 9 | 10 | 9 | 5 | 9 | 10 | 10 | 10 | 10 | 10 | 10 | 0 | 10 | 9 | 10 |
| Wheat | 2 | 7 | 8 | 4 | 8 | 4 | 9 | 6 | 1 | 1 | 2 | 1 | 2 | 1 | 2 | 8 | 9 | 9 | 9 | 0 | 4 | 8 | 8 |
| Wild oats | 0 | 4 | 5 | 5 | 4 | 2 | 4 | 1 | 6 | 1 | 6 | 2 | 0 | 1 | 1 | 7 | 4 | 5 | 3 | 0 | 6 | 5 | 4 |
| Wild oats | 0 | 5 | 6 | 4 | 2 | 4 | 3 | 3 | 5 | 3 | 2 | 2 | 1 | 1 | 1 | 7 | 6 | 6 | 5 | 0 | 4 | 7 | 4 |

Rate 250 g/ha

Postemergence

COMPOUND

| | 51 | 52 | 53 | | | | | | | | | | | | | | | | | 75 | 76 | 77 | 78 |
|---|---|---|---|---|---|---|---|---|---|---|---|---|---|---|---|---|---|---|---|---|---|---|---|
| B. signalgrass | 9 | 9 | 2 | | | | | | | | | | | | | | | | | 3 | 0 | 1 | 1 |
| Barnyardgrass | 7 | 7 | 2 | | | | | | | | | | | | | | | | | 3 | 0 | 0 | 0 |
| Bedstraw | 10 | 10 | 10 | | | | | | | | | | | | | | | | | 9 | 0 | 4 | 0 |

TABLE B-continued

Rate 250 g/ha

Preemergence

| | 1 | 2 | 3 | 4 | 5 | 6 | 7 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| Blackgrass | 9 | 9 | 1 | 2 | 5 | 2 | 6 | 2 | 3 | 7 | 0 | 5 | 9 | 4 | 0 | — | 5 | 9 | 4 | 0 | 8 | 0 | 2 | 6 |
| Cocklebur | 9 | — | 6 | 7 | 7 | 4 | 8 | 7 | — | 7 | 1 | 4 | 8 | 7 | 2 | — | 4 | 9 | 1 | 5 | 7 | 4 | 3 | 2 |
| Corn | 6 | 9 | 1 | 3 | 3 | 3 | 3 | 2 | 2 | 4 | 1 | 2 | 6 | 2 | 2 | — | 5 | 3 | 4 | 1 | 3 | 1 | 1 | 8 |
| Crabgrass | 10 | 10 | 4 | 5 | 8 | 4 | 7 | 5 | 4 | 9 | 1 | 8 | 10 | 8 | 1 | — | 8 | 9 | — | 1 | — | 1 | 2 | 8 |
| Ducksalad | 9 | 9 | 5 | 1 | 1 | 2 | 3 | 0 | 5 | 3 | 1 | 5 | 6 | 2 | 0 | 2 | 3 | 2 | 0 | 1 | 2 | — | 2 | 0 |
| Giant foxtail | 10 | 9 | 1 | 4 | 6 | 2 | 3 | 2 | 2 | 4 | 1 | 2 | 6 | 2 | 0 | — | 7 | 7 | — | 1 | 4 | 1 | 0 | 1 |
| Morningglory | 10 | 10 | — | 3 | 8 | 2 | 5 | 3 | 3 | 8 | 0 | 9 | 10 | 10 | 2 | — | 4 | 9 | 1 | 7 | 10 | 1 | 1 | 0 |
| Nutsedge | — | — | 0 | 0 | 10 | 9 | — | — | 10 | 0 | 8 | 1 | 4 | 0 | 0 | 2 | — | — | 0 | 0 | 0 | — | 4 | — |
| Rape | 10 | 9 | 8 | 9 | 0 | 4 | 0 | 2 | 0 | 4 | 2 | 7 | 8 | 10 | 1 | — | 7 | 10 | 2 | 1 | 9 | 2 | 2 | 0 |
| Redroot pigweed | 10 | 10 | 7 | 6 | 7 | 7 | 8 | 9 | 8 | 10 | 6 | 10 | 10 | 10 | 3 | 2 | 9 | 10 | 8 | 0 | 10 | 2 | 3 | 4 |
| Rice | 8 | 7 | 1 | 3 | 8 | 1 | 9 | 0 | 9 | 2 | 0 | 1 | 2 | 3 | 0 | — | 2 | 6 | 0 | 1 | 1 | 0 | 0 | 0 |
| S. Flatsedge | 9 | 9 | 9 | 9 | 4 | 6 | 2 | 7 | 1 | 8 | 0 | 8 | 9 | 7 | 3 | 4 | 4 | 6 | 0 | 0 | 3 | 1 | 1 | 0 |
| Soybean | 10 | 10 | 7 | 4 | 8 | 2 | 8 | — | 8 | 5 | 2 | 6 | 8 | 7 | 3 | — | 5 | 9 | 0 | 2 | 10 | 2 | 3 | 0 |
| Sugarbeets | 10 | 10 | 10 | 9 | 9 | 9 | 10 | 9 | 9 | 10 | 8 | 10 | 10 | 10 | 2 | — | 9 | 9 | 2 | 6 | 9 | 3 | 3 | 0 |
| Velvetleaf | 9 | 8 | 7 | 3 | 7 | 2 | 8 | 5 | 8 | 8 | 2 | 6 | 8 | 7 | 1 | — | 5 | 8 | 2 | 1 | 10 | 1 | 3 | 0 |
| Wheat | 9 | 7 | 1 | 2 | 2 | 3 | 3 | 2 | 2 | 3 | 2 | 2 | 5 | 2 | 0 | — | 4 | 5 | 1 | 3 | 3 | 0 | 1 | 0 |
| Wild oats | 9 | 8 | 3 | 3 | 3 | 2 | 3 | 1 | 2 | 5 | 1 | 5 | 9 | 2 | 0 | — | 4 | 9 | 1 | 1 | 3 | 0 | 1 | 0 |

COMPOUND

Rate 250 g/ha

Postemergence

| | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 49 | 50 |
|---|---|---|---|---|---|---|---|---|---|---|---|---|---|---|---|---|---|---|---|---|---|---|---|---|
| B. signalgrass | 1 | 3 | 9 | 4 | 6 | 9 | 7 | 1 | 1 | 0 | 0 | 0 | 1 | 0 | 1 | 7 | 10 | 9 | 8 | 0 | 9 | 9 | 5 | 1 |
| Bedstraw | 0 | — | 8 | 3 | 10 | — | 10 | 2 | 0 | 1 | 0 | 0 | 2 | 0 | — | 8 | 8 | 10 | 10 | 0 | 10 | 8 | 8 | 9 |
| Blackgrass | 0 | 4 | 6 | 3 | 2 | 2 | 4 | 0 | 0 | 0 | 1 | 0 | 0 | 0 | 2 | 10 | 10 | 8 | 9 | 0 | — | 10 | 6 | 10 |
| Cocklebur | 0 | — | — | 0 | 0 | 3 | 0 | 0 | 0 | 0 | 0 | 0 | 0 | 0 | 0 | 0 | 8 | 2 | 2 | 0 | 3 | 2 | 2 | 0 |
| Corn | 0 | 0 | 1 | 0 | 0 | — | 0 | 0 | 0 | 0 | 0 | 0 | — | 0 | 0 | 1 | 1 | 1 | 1 | 0 | 1 | 3 | 1 | 1 |
| Crabgrass | 1 | 5 | 10 | 7 | 8 | 1 | 0 | 1 | 1 | 1 | 0 | 0 | 0 | 0 | 0 | 9 | 2 | 10 | 9 | 0 | 10 | 3 | 9 | 0 |
| Giant foxtail | 1 | 9 | 10 | 3 | 9 | 10 | 3 | 5 | 1 | 0 | 0 | 0 | 0 | 0 | 3 | 10 | 10 | 9 | 9 | 0 | 10 | 10 | 9 | 9 |
| Morningglory | 0 | 2 | 3 | 3 | 3 | 10 | 5 | 1 | 1 | 0 | 0 | 0 | 1 | 0 | 2 | 2 | 10 | 10 | 10 | 0 | 10 | 6 | 4 | 8 |
| Nutsedge | — | 0 | 0 | — | 0 | 0 | 0 | — | 0 | 0 | 0 | 0 | 0 | 0 | 0 | 0 | 5 | — | — | 0 | 0 | — | — | 4 |

TABLE B-continued

| | | | | | | | | | | | | | | | | | | | | | | | | | |
|---|---|---|---|---|---|---|---|---|---|---|---|---|---|---|---|---|---|---|---|---|---|---|---|---|---|
| Rape | 0 | 3 | 4 | 1 | 3 | 1 | 10 | 2 | 0 | 0 | 2 | 10 | 10 | 10 | 0 | 10 | 10 | 10 | 10 | 10 |
| Redroot pigweed | 4 | 7 | 7 | 3 | 0 | 3 | 10 | 2 | 2 | 5 | 2 | 10 | 10 | 10 | 0 | 10 | 10 | 10 | 10 | 9 |
| Soybean | 0 | 0 | 1 | 0 | 10 | 0 | 1 | 0 | 0 | 0 | 0 | 4 | 7 | 7 | 0 | 2 | 7 | 2 | 1 |
| Sugarbeets | 0 | 8 | 3 | 4 | 6 | 3 | 10 | 4 | 4 | 1 | 6 | 10 | 10 | 10 | 0 | 10 | 10 | 9 | 10 |
| Velvetleaf | 0 | 1 | 2 | 0 | 0 | 0 | 0 | 1 | 0 | 0 | 1 | 8 | 2 | 10 | 0 | 2 | 5 | 8 | 9 |
| Wheat | 0 | 1 | 0 | 0 | 0 | 0 | 0 | 0 | 0 | 0 | 0 | 2 | 0 | 4 | 0 | 3 | 9 | 4 | 2 |
| Wild oats | 0 | 3 | 4 | 1 | 2 | 2 | 4 | 0 | 0 | 1 | 1 | 9 | 9 | 9 | 0 | 9 | 8 | 7 | 8 |

Rate 250 g/ha

| Preemergence | 51 | 52 | 53 | 54 | 59 | 60 | 61 | 62 | 63 | 64 | 65 | 66 | 67 | 68 | 70 | 72 | 73 | 74 | 75 | 76 | 77 | 78 |
|---|---|---|---|---|---|---|---|---|---|---|---|---|---|---|---|---|---|---|---|---|---|---|
| B. signalgrass | 9 | 10 | 2 | 3 | 9 | 3 | 8 | 8 | 8 | 10 | 1 | 9 | 10 | 9 | 0 | 7 | 9 | 0 | 9 | 0 | 0 | 0 |
| Bedstraw | 9 | 9 | 7 | 1 | 6 | 1 | 6 | 5 | 4 | 8 | 8 | 3 | 9 | 6 | 0 | 5 | 9 | 0 | 6 | — | 0 | 0 |
| Blackgrass | 10 | 10 | 1 | 3 | 7 | 2 | 5 | 1 | 8 | 6 | 1 | 8 | 8 | 7 | 0 | 4 | 10 | 0 | 9 | 0 | 0 | 0 |
| Cocklebur | 10 | 7 | 0 | 0 | — | 0 | 1 | — | — | — | 2 | 0 | 2 | 2 | 0 | 0 | 7 | 0 | 2 | 0 | 0 | 0 |
| Corn | 8 | 7 | 3 | 1 | 1 | 0 | 1 | 1 | 1 | 4 | 0 | 1 | 4 | 1 | 0 | 5 | 2 | 0 | 1 | 0 | 0 | 0 |
| Crabgrass | 10 | 10 | 6 | 3 | 10 | 6 | 8 | 9 | 8 | 10 | 0 | 9 | 10 | 9 | 0 | 9 | 10 | 0 | 9 | 0 | 1 | 0 |
| Giant foxtail | 10 | 10 | 6 | 8 | 10 | 5 | 10 | 4 | 6 | 5 | 0 | 2 | 10 | 9 | 0 | 9 | 10 | 0 | 5 | 0 | — | 0 |
| Morningglory | 10 | 10 | 2 | 2 | 10 | 5 | 10 | 4 | 10 | 10 | 0 | 3 | 10 | 5 | 0 | 7 | 9 | 0 | 10 | 0 | 1 | 0 |
| Nutsedge | — | — | 0 | 0 | 0 | — | 0 | 0 | 0 | — | 0 | — | — | 0 | — | 8 | 0 | 0 | 0 | 0 | — | 0 |
| Rape | 10 | 10 | 7 | 3 | 7 | 1 | 9 | 2 | 4 | 8 | 0 | 4 | 10 | 4 | 0 | 9 | 6 | 0 | 4 | 0 | 0 | 0 |
| Redroot pigweed | 10 | 10 | 7 | 7 | 10 | 10 | 9 | 10 | 10 | 10 | 0 | 9 | 10 | 10 | 0 | 9 | 10 | 0 | 10 | 0 | 0 | 0 |
| Soybean | 9 | 8 | 0 | 0 | 0 | 0 | 1 | 0 | 0 | 1 | 0 | 0 | 3 | 2 | — | 3 | 1 | 0 | 0 | 0 | 0 | 0 |
| Sugarbeets | 10 | 10 | 9 | 7 | 10 | 9 | 10 | 10 | 10 | 10 | 0 | 10 | 10 | 10 | 0 | 10 | 10 | 0 | 10 | 0 | 0 | 0 |
| Velvetleaf | 10 | 10 | 4 | 1 | 9 | 1 | 10 | 2 | 2 | 6 | 0 | 2 | 10 | 7 | 0 | 7 | 7 | 0 | 9 | 0 | 3 | 0 |
| Wheat | 5 | 3 | 0 | 0 | 3 | 0 | 4 | 0 | 3 | 1 | 0 | 2 | 3 | 2 | 0 | 3 | 3 | 0 | 4 | 0 | 0 | 0 |
| Wild oats | 8 | 9 | 1 | 3 | 9 | 0 | 7 | 4 | 5 | 5 | 0 | 5 | 6 | 7 | 0 | 3 | 10 | 0 | 7 | 0 | 0 | 0 |

Rate 125 g/ha

| Postemergence | 1 | 2 | 3 | 4 | 5 | 6 | 7 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|---|---|---|---|---|
| B. signalgrass | 6 | — | 3 | 2 | 4 | — | 1 | 8 | 3 | 3 | 5 | 5 | 2 | 4 | 1 | 5 | 2 | 2 | 2 | 4 | 7 | 5 | 2 | 3 |
| Barnyardgrass | — | 4 | 4 | 8 | 2 | 1 | 1 | 5 | 2 | — | 2 | 2 | 5 | 8 | 3 | 4 | 1 | 2 | 0 | 4 | 5 | 5 | 3 | 4 |
| Bedstraw | 9 | 9 | 8 | 8 | 9 | 7 | 3 | 10 | 9 | 9 | 9 | 9 | 4 | 9 | 4 | 9 | 8 | 3 | 4 | 9 | 8 | 9 | 10 | 10 |
| Blackgrass | 7 | 6 | 2 | 4 | 4 | 7 | 0 | 8 | 1 | 3 | 3 | 3 | 2 | 9 | 1 | 6 | 2 | 1 | 2 | 4 | 8 | 7 | 3 | 4 |
| Cocklebur | 8 | 8 | 3 | 4 | 7 | 2 | — | 9 | 8 | 8 | 8 | 9 | 7 | 9 | 4 | 8 | 7 | 3 | 5 | 8 | 8 | 10 | 9 | 9 |
| Corn | 4 | 4 | 2 | 6 | 2 | 6 | 1 | 4 | 2 | 3 | 2 | 3 | 2 | 4 | 1 | 4 | 2 | 2 | 3 | 3 | 3 | 3 | 3 | 2 |
| Crabgrass | 9 | 9 | 2 | 2 | 2 | 3 | 1 | 9 | 2 | 4 | 3 | 4 | 2 | 9 | 2 | 5 | 2 | 2 | 0 | 6 | 9 | 9 | 1 | 2 |
| Ducksalad | — | 0 | 3 | 7 | 3 | 8 | — | 6 | 1 | — | 1 | 1 | 1 | 6 | 0 | 4 | 2 | 1 | 2 | 4 | 4 | 4 | 8 | 8 |
| Giant foxtail | 7 | 9 | 2 | 3 | 0 | 0 | 0 | 5 | 2 | 4 | 3 | 3 | 2 | 7 | 1 | 4 | 1 | 0 | 2 | 4 | 6 | 5 | 2 | 7 |
| Morningglory | 8 | 9 | 7 | 8 | 2 | 4 | 0 | 5 | 7 | — | 3 | 7 | 1 | 8 | 8 | 8 | 8 | 3 | 0 | 8 | 6 | 9 | 10 | 4 |
| Nutsedge | — | 0 | 0 | 0 | 0 | — | 1 | 10 | 0 | 10 | 0 | 0 | 0 | 2 | 1 | 0 | 0 | 0 | 4 | 2 | 10 | 0 | 1 | 10 |
| Rape | 9 | 9 | 6 | 10 | 9 | 8 | 0 | 10 | 9 | 9 | 9 | 8 | 6 | 9 | 0 | 8 | 7 | 0 | 4 | 10 | 10 | 10 | 10 | 10 |
| Redroot pigweed | 9 | 9 | 0 | 9 | 9 | 7 | 5 | 10 | 9 | 10 | 9 | 9 | 4 | 9 | 2 | 10 | 6 | 5 | 7 | 9 | 10 | 10 | 1 | 1 |
| Rice | — | 4 | 4 | 2 | 1 | 3 | 3 | 6 | 2 | — | 2 | 2 | 8 | 7 | 6 | 4 | 0 | 0 | 0 | 4 | 4 | 4 | 10 | 10 |
| S. Flatsedge | — | 5 | 9 | 6 | 3 | 5 | 0 | 9 | 9 | 7 | 6 | 4 | 4 | 8 | 1 | 8 | 1 | 2 | 5 | 8 | 8 | 8 | 1 | 4 |
| Soybean | 8 | 7 | 7 | 7 | 3 | 6 | — | 6 | 6 | — | 5 | 5 | 8 | 9 | 2 | 3 | 3 | 4 | 0 | 6 | 7 | 7 | 6 | 5 |
| Sugarbeets | 10 | 9 | 9 | 9 | 10 | 8 | 4 | 10 | 8 | 10 | 8 | 10 | 4 | 8 | 8 | 10 | 4 | 2 | 5 | 9 | 8 | 10 | 10 | 10 |
| Velvetleaf | 8 | 9 | 2 | 6 | 7 | 7 | 3 | 10 | 7 | 8 | 7 | 7 | 4 | 8 | 2 | 4 | 6 | 6 | 6 | 8 | 7 | 9 | 6 | 9 |
| Wheat | 2 | 2 | 2 | 2 | 2 | 2 | 0 | 3 | 3 | 2 | 3 | 3 | 0 | 4 | 0 | 3 | 3 | 0 | 3 | 4 | 4 | 4 | 2 | 4 |

TABLE B-continued

| Postemergence | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 49 | 50 |
|---|---|---|---|---|---|---|---|---|---|---|---|---|---|---|---|---|---|---|---|---|---|---|---|---|
| Rate 125 g/ha | 7 | 3 | 2 | 2 | 4 | 3 | 0 | 4 | 2 | 3 | 3 | 3 | 1 | 7 | 0 | 4 | 5 | 1 | 3 | 5 | 6 | 6 | 3 | 3 |
| B. signalgrass | 1 | 5 | 5 | 3 | 2 | 3 | 2 | 2 | 1 | 1 | 1 | 0 | 1 | 1 | 1 | 3 | 7 | 4 | 4 | 0 | 4 | 5 | 3 | 1 |
| Barnyardgrass | 0 | 2 | 4 | 3 | 3 | 3 | 3 | 2 | 0 | 2 | 0 | 0 | 0 | 0 | 2 | 5 | 4 | 4 | 4 | 0 | 3 | 3 | 5 | 4 |
| Bedstraw | 3 | 9 | 8 | 9 | 6 | 6 | 6 | 9 | 3 | 6 | 7 | 1 | 7 | 3 | 4 | 9 | 9 | 10 | 9 | 0 | 9 | — | — | 10 |
| Blackgrass | 1 | 4 | 5 | 3 | 1 | 2 | 2 | 1 | 1 | 1 | 1 | 0 | 0 | 1 | 1 | 6 | 6 | 6 | 5 | 0 | 5 | 5 | 6 | 5 |
| Cocklebur | 2 | 7 | 8 | 6 | 8 | 6 | 8 | 6 | 2 | 2 | 2 | 2 | 7 | 2 | 2 | 8 | 9 | 7 | 9 | 0 | 9 | 8 | 7 | 4 |
| Corn | 1 | 3 | 3 | 2 | 2 | 2 | 1 | 1 | 1 | 2 | 1 | 0 | 1 | 1 | 1 | 2 | 3 | 4 | 3 | 0 | 2 | 3 | 3 | 2 |
| Crabgrass | 1 | 4 | 9 | 6 | 1 | 8 | 2 | 0 | 1 | 2 | 0 | 0 | 0 | 0 | 1 | 9 | 7 | 8 | 4 | 0 | 6 | 9 | 6 | 2 |
| Ducksalad | 0 | 1 | 4 | 3 | 4 | 2 | 3 | 3 | 0 | 0 | 0 | 0 | 0 | 0 | 5 | 3 | 8 | 9 | 7 | 0 | 1 | 3 | 4 | 5 |
| Giant foxtail | 1 | 4 | 4 | 4 | 1 | 3 | 1 | 1 | 1 | 1 | 1 | 1 | 1 | 0 | 0 | 6 | 7 | 9 | 7 | 0 | 4 | 4 | 5 | 2 |
| Morningglory | 3 | 8 | 3 | 10 | 5 | 3 | 8 | 5 | 1 | 1 | 2 | 2 | 1 | 0 | 2 | 8 | 9 | 9 | 7 | 0 | 10 | 6 | 6 | 3 |
| Nutsedge | 0 | — | 3 | 0 | 0 | 3 | 0 | 1 | 0 | 0 | 0 | 0 | 1 | 0 | — | 0 | 0 | 2 | — | 0 | — | — | — | 2 |
| Rape | 6 | 8 | 9 | 9 | 8 | 8 | 8 | 7 | 3 | 6 | 5 | 3 | 4 | 3 | 6 | 10 | 10 | 10 | 10 | 0 | 9 | 10 | 9 | 10 |
| Redroot pigweed | 6 | 9 | 9 | 10 | 9 | 9 | 9 | 2 | 3 | 3 | 4 | 1 | 0 | 1 | 3 | 10 | 9 | 10 | 10 | 0 | 9 | 9 | 9 | 8 |
| Rice | 0 | 1 | 2 | 2 | 1 | 2 | 1 | 1 | 1 | 1 | 0 | 0 | 3 | 2 | 1 | 5 | 6 | 6 | 6 | 0 | 2 | 5 | 4 | 3 |
| S. Flatsedge | 1 | 5 | 8 | 6 | 6 | 6 | 5 | 7 | 1 | 2 | 5 | 0 | 0 | 0 | 4 | 7 | 9 | 9 | 9 | 0 | 5 | 7 | 4 | 8 |
| Soybean | 3 | 5 | 7 | 4 | 3 | 7 | 4 | 2 | 2 | 2 | 2 | 1 | 1 | 2 | 2 | 7 | 7 | 9 | 6 | 0 | 8 | 8 | 7 | 7 |
| Sugarbeets | 8 | 9 | 9 | 9 | 10 | 10 | 10 | 10 | 8 | 10 | 8 | 5 | 9 | 9 | 10 | 10 | 10 | 10 | 10 | 0 | 10 | 9 | 9 | 8 |
| Velvetleaf | 1 | 7 | 4 | 3 | 6 | 2 | 8 | 4 | 1 | 1 | 1 | 0 | 1 | 1 | 2 | 8 | 9 | 9 | 8 | 0 | 9 | 7 | 8 | 7 |
| Wheat | 0 | 4 | 4 | 3 | 2 | 3 | 2 | 2 | 1 | 0 | 1 | 0 | 0 | 1 | 1 | 3 | 3 | 4 | 3 | 0 | 3 | 5 | 5 | 3 |
| Wild oats | 0 | 4 | 5 | 2 | 2 | 2 | 3 | 2 | 1 | 1 | 1 | 0 | 1 | 1 | 0 | 5 | 6 | 5 | 4 | 0 | 4 | 8 | 6 | 3 |

| Postemergence | 51 | 52 | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|
| Rate 125 g/ha | | | | | | | | | | | | | | | | | | | | | | | | |
| B. signalgrass | 8 | 9 | 1 | 3 | 2 | 2 | 4 | 2 | 3 | 5 | 1 | 3 | 7 | 3 | 3 | 0 | 2 | 4 | 9 | 1 | 2 | 0 | 0 | 0 |
| Barnyardgrass | 6 | 6 | 2 | 3 | 4 | 1 | 3 | 2 | 3 | 3 | 0 | 3 | 3 | 3 | 2 | 0 | 2 | 3 | 5 | 0 | 2 | 0 | 0 | 0 |
| Bedstraw | 10 | 10 | 8 | 4 | 7 | 3 | 8 | 3 | 2 | 4 | 3 | 3 | 9 | 6 | 9 | 1 | — | — | 9 | 1 | 9 | 0 | 1 | 0 |
| Blackgrass | 9 | 9 | 1 | 1 | 3 | 1 | 4 | 4 | 1 | 5 | 0 | 3 | 8 | 3 | 3 | 0 | 3 | 5 | 7 | 0 | 6 | 3 | 0 | 0 |
| Cocklebur | 9 | 9 | 8 | 3 | 7 | 3 | 7 | 1 | 3 | 7 | 1 | 4 | 7 | 1 | 8 | 2 | 4 | 4 | 4 | 5 | 7 | 1 | 3 | 0 |
| Corn | 8 | 5 | 1 | 2 | 2 | 2 | 3 | 5 | 2 | 3 | 1 | 2 | 5 | — | 2 | 1 | 3 | 3 | 3 | 1 | 3 | 0 | 1 | 0 |
| Crabgrass | 10 | 8 | 2 | 4 | 6 | 3 | 3 | 3 | 3 | 5 | 1 | 7 | 9 | 1 | 4 | 1 | 0 | 6 | 6 | 1 | 4 | 0 | 2 | 0 |
| Ducksalad | 9 | 9 | 2 | 0 | 4 | 2 | 2 | 1 | 0 | 6 | 0 | 3 | 4 | 8 | 1 | 0 | 0 | 2 | 2 | 0 | 1 | 0 | 0 | 0 |
| Giant foxtail | 10 | 8 | 1 | 3 | 6 | 2 | 4 | 4 | 2 | 3 | 1 | 2 | 6 | 2 | 3 | 0 | 2 | 6 | 8 | 0 | 2 | 0 | 1 | 0 |
| Morningglory | 10 | 10 | 3 | 3 | — | 4 | 9 | 4 | 4 | 8 | 0 | 4 | 7 | 7 | 10 | 1 | 6 | 4 | 9 | 1 | 10 | 0 | 4 | 0 |
| Nutsedge | — | 3 | 0 | 0 | 0 | 0 | 0 | 0 | — | 0 | 0 | 1 | 2 | 0 | — | 0 | — | — | 0 | 0 | 0 | — | — | 0 |
| Rape | 9 | 9 | 8 | 8 | 7 | 3 | 7 | 2 | 4 | 4 | 1 | 3 | 8 | 6 | 8 | 0 | 7 | 7 | 10 | 1 | 7 | 2 | 1 | 0 |
| Redroot pigweed | 10 | 10 | 6 | 5 | 8 | 7 | 9 | 9 | 9 | 9 | 3 | 9 | 10 | 10 | 10 | 2 | 8 | 9 | 9 | 2 | 9 | 9 | 2 | 0 |
| Rice | 5 | 5 | 1 | 2 | 3 | 0 | 0 | 0 | 0 | 1 | 0 | 1 | 2 | 1 | 2 | 0 | 2 | 0 | 5 | 0 | 1 | 1 | 0 | 0 |
| S. Flatsedge | 9 | 9 | 8 | 8 | 7 | 5 | 5 | 6 | 7 | 8 | 2 | 8 | 8 | 7 | 4 | 0 | 2 | 3 | 3 | 0 | 2 | 0 | 0 | 0 |
| Soybean | 9 | 9 | 5 | 3 | 2 | 2 | 2 | 1 | 2 | 2 | 3 | 5 | 7 | 5 | 4 | 0 | 4 | 2 | 9 | 2 | 3 | 0 | 1 | 0 |
| Sugarbeets | 10 | 10 | 10 | 7 | 9 | 8 | 10 | 9 | 9 | 10 | 2 | 10 | 10 | 10 | 10 | 1 | 8 | 9 | 10 | 2 | 10 | 2 | 1 | 0 |
| Velvetleaf | 8 | 8 | 6 | 2 | 7 | 2 | 7 | 2 | 8 | 7 | 7 | 5 | 9 | 7 | 8 | 1 | 6 | 6 | 3 | 1 | 9 | 1 | 1 | 0 |
| Wheat | 9 | 7 | 1 | 2 | 2 | 3 | 3 | 2 | 2 | 3 | 1 | 2 | 4 | 2 | 4 | 0 | 4 | 3 | 4 | 1 | 2 | 0 | 0 | 0 |
| Wild oats | 9 | 8 | 1 | 2 | 1 | 2 | 3 | 1 | 2 | 4 | 1 | 2 | 7 | 2 | 3 | 0 | 2 | 2 | 7 | 1 | 3 | 0 | 0 | 0 |

TABLE B-continued

| Rate 125 g/ha | | | | | | | | | | | | | | | | | | | | | | | | | |
|---|---|---|---|---|---|---|---|---|---|---|---|---|---|---|---|---|---|---|---|---|---|---|---|---|---|
| | | | | | | | | | | | | | COMPOUND | | | | | | | | | | | | |
| Preemergence | 1 | 2 | 3 | 4 | 5 | 6 | 7 | 9 | 10 | 11 | 12 | 13 | 14 | 15 | 16 | 17 | 18 | 19 | 20 | 21 | 22 | 23 | 24 | 25 |
| B. signalgrass | 9 | — | 2 | — | 8 | 4 | 0 | 9 | 1 | 3 | 8 | 8 | 0 | 9 | 2 | 7 | 1 | 0 | 1 | 3 | 9 | 9 | 3 | 2 |
| Bedstraw | 8 | 10 | 0 | 3 | 4 | 0 | 0 | 7 | 7 | 8 | 4 | 2 | 0 | 8 | 0 | 3 | 2 | 0 | 0 | 1 | 7 | 8 | 1 | 1 |
| Blackgrass | 9 | 7 | 3 | 9 | 3 | 0 | 0 | 9 | 2 | 3 | 4 | 4 | 0 | 10 | 0 | 6 | 0 | 0 | 2 | 3 | 9 | 9 | 2 | 5 |
| Cocklebur | 2 | 1 | 0 | 0 | 0 | 0 | 0 | 2 | 0 | — | 0 | — | — | 1 | 0 | 0 | — | — | 0 | 0 | 1 | 1 | 0 | 0 |
| Corn | 1 | 1 | 0 | 0 | 0 | 0 | 0 | 1 | 0 | 0 | 0 | 1 | 0 | 1 | 0 | 0 | 0 | 0 | 0 | 0 | 0 | 0 | 0 | 0 |
| Crabgrass | 10 | 10 | 1 | 6 | 9 | 2 | 0 | 10 | 7 | 7 | 4 | 10 | 0 | 10 | 0 | 8 | 0 | 0 | 0 | 6 | 10 | 10 | 3 | 0 |
| Giant foxtail | 10 | 10 | 8 | 10 | 9 | 6 | 0 | 10 | 7 | 7 | 7 | 10 | 1 | 10 | 3 | 10 | 4 | 0 | 1 | 8 | 10 | 10 | 6 | 4 |
| Morningglory | 10 | 9 | 3 | 7 | 4 | 1 | 0 | 10 | 3 | 9 | 6 | 10 | 4 | 7 | 0 | 1 | 0 | 0 | 0 | 1 | 10 | 8 | 4 | 3 |
| Nutsedge | 0 | 0 | 0 | 0 | 0 | 0 | 0 | 0 | 0 | 8 | 0 | 0 | 0 | 0 | 0 | 0 | 4 | — | — | 0 | 1 | 0 | 0 | 0 |
| Rape | 10 | 10 | 1 | 4 | 10 | 2 | 0 | 9 | 4 | 9 | 5 | 6 | 1 | 9 | 0 | 2 | 0 | 0 | 0 | 3 | 10 | 7 | 2 | 7 |
| Redroot pigweed | 10 | 10 | 0 | 8 | 0 | 3 | 0 | 10 | 6 | 9 | 9 | 9 | 2 | 10 | 0 | 9 | 3 | 0 | 0 | 8 | 10 | 9 | 8 | 3 |
| Soybean | 1 | 1 | 0 | 0 | 1 | 0 | 0 | 0 | 0 | 1 | 2 | 0 | 0 | 0 | 0 | 0 | 0 | 0 | 0 | 0 | 1 | 1 | 0 | 0 |
| Sugarbeets | 10 | 10 | 8 | 8 | 8 | 2 | 0 | 10 | — | 10 | 8 | 10 | 5 | 10 | 1 | 8 | 6 | 0 | 0 | 8 | 9 | 8 | 3 | 8 |
| Velvetleaf | 10 | 6 | 1 | 6 | 7 | 0 | 0 | 8 | 7 | 6 | 4 | 7 | 0 | 7 | 0 | 0 | 0 | 0 | 0 | 0 | 8 | 3 | 0 | 1 |
| Wheat | 5 | 2 | 0 | 0 | 2 | 0 | 0 | 2 | 0 | 1 | 0 | 0 | 1 | 4 | 0 | 1 | 0 | 0 | 0 | 0 | 2 | 3 | 3 | 0 |
| Wild oats | 9 | 9 | 4 | 7 | 5 | 0 | 0 | 8 | 1 | 4 | 2 | 5 | 0 | 9 | 1 | 5 | 3 | 0 | 2 | 5 | 8 | 8 | 1 | 3 |

| Rate 125 g/ha | | | | | | | | | | | | | | | | | | | | | | | | | |
|---|---|---|---|---|---|---|---|---|---|---|---|---|---|---|---|---|---|---|---|---|---|---|---|---|---|
| | | | | | | | | | | | | | COMPOUND | | | | | | | | | | | | |
| Preemergence | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 49 | 50 |
| B. signalgrass | 0 | 1 | 5 | 3 | 4 | 9 | 6 | 1 | 0 | 0 | 0 | 9 | 0 | 0 | 0 | 6 | 9 | 9 | 8 | 0 | 9 | 6 | 1 | 1 |
| Bedstraw | 0 | 0 | 4 | 1 | 10 | — | 8 | 1 | 0 | 0 | 0 | 2 | 1 | 0 | — | 2 | 8 | 9 | 5 | 0 | 9 | 8 | 7 | 7 |
| Blackgrass | 0 | 2 | 5 | 1 | 2 | 2 | 2 | 0 | 0 | 0 | 0 | 3 | 4 | 0 | 1 | 9 | 10 | 5 | 6 | 0 | 8 | 8 | 4 | 5 |
| Cocklebur | 0 | — | 0 | 0 | 0 | 0 | 0 | 0 | 0 | 0 | 0 | 0 | — | 0 | 0 | 0 | 3 | 2 | 2 | 0 | — | 2 | 0 | 0 |
| Corn | 0 | 0 | 0 | 0 | 0 | 0 | 0 | 0 | 0 | 0 | 0 | 1 | 0 | 0 | 0 | 1 | 1 | 1 | 1 | 0 | 1 | 1 | 1 | 0 |
| Crabgrass | 0 | 2 | 2 | 4 | 0 | 4 | 1 | 0 | 0 | 0 | 0 | 0 | 0 | 0 | 0 | 9 | 10 | 10 | 4 | 0 | 9 | 10 | 7 | 9 |
| Giant foxtail | 1 | 5 | 9 | 4 | 3 | 5 | 2 | 2 | 0 | 1 | 0 | 1 | 1 | 0 | 1 | 9 | 10 | 9 | 5 | 0 | 10 | 10 | 8 | 7 |
| Morningglory | 0 | 2 | 2 | 2 | 5 | 2 | 2 | 1 | 0 | 0 | 0 | 10 | 0 | 0 | 1 | 1 | 10 | 10 | 9 | 0 | 10 | 6 | 3 | 3 |
| Nutsedge | 0 | 0 | 0 | 0 | 0 | 0 | 0 | 0 | 0 | 0 | 0 | 0 | 0 | 0 | — | 0 | 0 | 0 | — | 0 | 0 | — | — | — |
| Rape | 0 | 2 | 2 | 1 | 2 | 2 | 10 | 0 | 0 | 0 | 0 | 0 | 0 | 0 | 1 | 3 | 10 | 10 | 8 | 0 | 9 | 9 | 8 | 10 |
| Redroot pigweed | 0 | 6 | 6 | 3 | 7 | 0 | 10 | 0 | 0 | 0 | 0 | 2 | 0 | 0 | 1 | 10 | 10 | 10 | 9 | 0 | 10 | 9 | 8 | 9 |
| Soybean | 0 | 0 | 0 | 0 | 0 | 0 | 0 | 0 | 0 | 0 | 0 | 3 | 0 | 0 | 0 | 0 | 4 | 5 | 2 | 0 | 3 | 0 | 1 | 1 |
| Sugarbeets | 0 | 1 | 2 | 3 | 9 | 0 | 10 | 0 | 0 | 0 | 0 | 0 | 0 | 0 | 6 | 6 | 10 | 10 | 10 | 0 | 10 | 7 | 6 | 6 |
| Velvetleaf | 0 | 0 | 0 | 0 | 2 | 0 | 0 | 0 | 0 | 0 | 0 | 1 | 0 | 0 | 1 | 3 | 7 | 7 | 1 | 0 | 10 | 10 | 8 | 7 |
| Wheat | 0 | 0 | 0 | 0 | 1 | 1 | 0 | 0 | 0 | 0 | 0 | 0 | — | 0 | 0 | 1 | 2 | 2 | 1 | 0 | 3 | 3 | 4 | 2 |
| Wild oats | 0 | 1 | 3 | 0 | 1 | 1 | 3 | 0 | 0 | 0 | 0 | 9 | 0 | 0 | 2 | 9 | 8 | 9 | 7 | 0 | 8 | 9 | 6 | 4 |

| Rate 125 g/ha | | | | | | | | | | | | | | | | | | | | | | | | | |
|---|---|---|---|---|---|---|---|---|---|---|---|---|---|---|---|---|---|---|---|---|---|---|---|---|---|
| | | | | | | | | | | | | | COMPOUND | | | | | | | | | | | | |
| Preemergence | 51 | 52 | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
| B. signalgrass | 9 | 9 | 1 | 1 | 9 | 3 | 7 | 4 | 7 | 9 | 0 | 9 | 9 | 8 | 9 | 0 | 2 | 2 | 9 | 0 | 9 | 0 | 0 | 0 |
| Bedstraw | 10 | 8 | 3 | 0 | 6 | 0 | 4 | 1 | 4 | 8 | 0 | 2 | 9 | 5 | 9 | 0 | 1 | — | 8 | 0 | 6 | — | — | 0 |
| Blackgrass | 9 | 8 | 0 | 1 | 3 | 1 | 1 | 1 | 3 | 6 | 0 | 3 | 4 | 5 | 4 | 0 | 2 | 1 | 9 | 0 | 8 | 0 | 0 | 0 |
| Cocklebur | 10 | — | 0 | 0 | 2 | 0 | 3 | 0 | — | 1 | 0 | 0 | — | — | 2 | 0 | 0 | 0 | 0 | 0 | 0 | 0 | 0 | 0 |
| Corn | 8 | 3 | 0 | 0 | 1 | 0 | 1 | 1 | 1 | 3 | 0 | 1 | 4 | 1 | 0 | 0 | 1 | 4 | 1 | 0 | 0 | 0 | 0 | 0 |
| Crabgrass | 10 | 10 | 4 | 0 | 9 | 2 | 5 | 3 | 6 | 10 | 0 | 9 | 9 | 4 | 9 | 0 | 2 | 9 | 10 | 0 | 9 | 0 | 0 | 0 |

TABLE B-continued

| | 1 | 2 | 4 | 5 | 6 | 9 | 10 | 11 | 12 | 13 |
|---|---|---|---|---|---|---|---|---|---|---|
| Giant foxtail | 10 | 9 | 5 | 1 | 10 | 2 | 9 | 2 | 3 | 2 |
| Morningglory | 10 | 10 | 2 | 1 | 6 | 2 | 3 | 2 | 7 | 10 |
| Nutsedge | 9 | — | 0 | 0 | 0 | 0 | 0 | 0 | 0 | — |
| Rape | 10 | 10 | 5 | 2 | 7 | 0 | 8 | 1 | 3 | 4 |
| Redroot pigweed | 10 | 10 | 2 | 0 | 10 | 0 | 9 | 9 | 9 | 9 |
| Soybean | 9 | 7 | 0 | 0 | 2 | 0 | 1 | 0 | 0 | 0 |
| Sugarbeets | 10 | 10 | 8 | 1 | 10 | 8 | 10 | 10 | 10 | 10 |
| Velvetleaf | 10 | 10 | 2 | 0 | 7 | 1 | 10 | 2 | 2 | 6 |
| Wheat | 3 | 2 | 0 | 0 | 2 | 0 | 3 | 0 | 2 | 0 |
| Wild oats | 7 | 5 | 0 | 1 | 8 | 0 | 5 | 3 | 3 | 4 |

Rate 62 g/ha

COMPOUND

| Postemergence | 1 | 2 | 4 | 5 | 6 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|
| B. signalgrass | 3 | — | 1 | 3 | — | 5 | 2 | 3 | 4 | 5 | 2 | 4 | 1 | 4 | 2 | 1 | 2 | 3 | 5 | 4 | 2 | 2 | 1 | 3 |
| Barnyardgrass | — | 3 | 4 | 2 | 0 | 5 | 1 | — | 2 | 2 | 4 | 6 | 2 | 4 | 2 | 0 | 0 | 3 | 4 | 4 | 2 | 3 | 0 | 1 |
| Bedstraw | 9 | 9 | 6 | 6 | 5 | 10 | 8 | 8 | 7 | 7 | 4 | 9 | 3 | 8 | 7 | 2 | 4 | 5 | — | 9 | 4 | 9 | — | 8 |
| Blackgrass | 7 | 3 | 3 | 3 | 0 | 3 | 1 | 2 | 2 | 3 | 1 | 6 | — | 3 | 2 | 1 | 2 | 3 | 5 | 6 | 2 | 3 | 0 | 4 |
| Cocklebur | 7 | 8 | 5 | 5 | 5 | 9 | 6 | 7 | — | 6 | 4 | 9 | 4 | 4 | 6 | 2 | 4 | 7 | 8 | 9 | 9 | 9 | 2 | 7 |
| Corn | 4 | 2 | 2 | 2 | 3 | 3 | 2 | 3 | 2 | 3 | 2 | 3 | 1 | 2 | 2 | 1 | 2 | 3 | 3 | 2 | 1 | 1 | 1 | 7 |
| Crabgrass | 4 | 8 | 4 | 2 | 5 | 9 | 2 | 2 | 2 | 3 | 2 | 9 | 2 | 4 | 4 | 0 | 2 | 3 | 3 | 7 | 8 | 7 | 1 | 3 |
| Ducksalad | — | 0 | 0 | 0 | 0 | 4 | 1 | — | 0 | 0 | 2 | 6 | 0 | 3 | 1 | 1 | 0 | 3 | 3 | 2 | 0 | 3 | 0 | 3 |
| Giant foxtail | 3 | 7 | 2 | 2 | — | 4 | 2 | 2 | 2 | 2 | 1 | 6 | — | 3 | 3 | 0 | 2 | 1 | 6 | 2 | 2 | 3 | 1 | 0 |
| Morningglory | 4 | 8 | 8 | 3 | 3 | 10 | 5 | 7 | 9 | 7 | 2 | 7 | 1 | 7 | 0 | 3 | 0 | 8 | 10 | 6 | 8 | 10 | 3 | 3 |
| Nutsedge | — | 0 | 0 | 0 | 2 | 0 | 0 | — | 0 | 0 | 2 | 8 | — | 2 | 0 | 3 | 3 | 2 | 10 | 0 | 0 | 10 | 0 | 5 |
| Rape | 9 | 9 | 9 | 8 | 8 | 9 | 8 | 9 | 7 | 6 | 5 | 9 | — | 0 | 4 | 2 | 3 | 9 | 10 | 6 | 8 | 10 | 3 | 8 |
| Redroot pigweed | 9 | 7 | 8 | 9 | 5 | 10 | 9 | 9 | 9 | 9 | 8 | 9 | 1 | 7 | 6 | 2 | 5 | 8 | 10 | 9 | 9 | 10 | 6 | 7 |
| Rice | — | 3 | 2 | 1 | 1 | 5 | 0 | — | 1 | 0 | 4 | 6 | 5 | 9 | 1 | 0 | 0 | 3 | 3 | 3 | 1 | 3 | 0 | 0 |
| S. Flatsedge | — | 3 | 5 | 3 | 3 | 8 | 6 | — | 4 | 2 | 8 | 7 | 1 | 4 | 6 | 1 | 4 | 6 | 6 | 4 | 0 | 4 | 3 | 5 |
| Soybean | 8 | 6 | 6 | 3 | 6 | 8 | 6 | 5 | 5 | 4 | 4 | 9 | 3 | 3 | 2 | 3 | 3 | 6 | 6 | 8 | 3 | 10 | 5 | 5 |
| Sugarbeets | 10 | 9 | 9 | 9 | 7 | 10 | 8 | 9 | 9 | 9 | 7 | 9 | 8 | 9 | 9 | 2 | 4 | 9 | 10 | 10 | 10 | 10 | 9 | 9 |
| Velvetleaf | 7 | 8 | 5 | 6 | 7 | 10 | 6 | 8 | 7 | 4 | 5 | 5 | 1 | 2 | 7 | 1 | 4 | 7 | 8 | 9 | 2 | 8 | 1 | 5 |
| Wheat | 2 | 2 | 1 | 2 | 1 | 3 | 2 | 2 | 3 | 2 | 3 | 4 | 0 | 3 | 5 | 1 | 4 | 4 | 4 | 3 | 2 | 2 | 0 | 3 |
| Wild oats | 4 | 3 | 2 | 3 | 0 | 3 | 2 | 2 | 3 | 3 | 0 | 6 | 0 | 3 | 3 | 0 | 2 | 4 | 5 | 5 | 7 | 3 | 3 | 3 |

Rate 62 g/ha

COMPOUND

| Postemergence | 28 | 29 | 30 | 31 | 32 | 33 | 34 | 35 | 36 | 37 | 38 | 39 | 40 | 41 | 42 | 43 | 44 | 45 | 46 | 47 | 49 | 50 | 51 | 52 |
|---|---|---|---|---|---|---|---|---|---|---|---|---|---|---|---|---|---|---|---|---|---|---|---|---|
| B. signalgrass | 4 | 3 | 1 | 3 | 1 | 1 | 1 | 1 | 1 | 0 | 1 | 1 | 1 | 2 | 6 | 4 | 3 | 0 | 3 | 4 | 2 | 1 | 2 | 4 |
| Barnyardgrass | 3 | 2 | 3 | 2 | 2 | 1 | 0 | 0 | 0 | 0 | 0 | 0 | 2 | 5 | 4 | 4 | 3 | 0 | 2 | 2 | 5 | 3 | 5 | 5 |
| Bedstraw | 2 | 2 | 1 | 4 | 6 | 9 | 2 | 6 | 6 | 6 | 7 | 3 | 4 | 9 | 9 | 9 | 8 | 0 | 8 | 9 | 9 | 9 | 9 | 9 |
| Blackgrass | 4 | 2 | 0 | 2 | 1 | 0 | 0 | 0 | 0 | 1 | 0 | 1 | 2 | 5 | 6 | 6 | 4 | 0 | 4 | 5 | 5 | 5 | 2 | 5 |
| Cocklebur | 7 | 6 | 5 | 6 | 8 | 3 | 2 | 1 | 1 | 0 | 4 | 2 | 5 | 7 | 9 | — | 8 | 0 | 8 | 7 | 7 | 7 | 6 | 8 |
| Corn | 2 | 2 | 2 | 2 | 1 | 1 | 1 | 2 | 0 | 1 | 1 | 1 | 1 | 2 | 3 | 3 | 3 | 0 | 2 | 3 | 3 | 4 | 6 | 8 |
| Crabgrass | 3 | 4 | 4 | 4 | 4 | 1 | 0 | 0 | 1 | 1 | 0 | 1 | 1 | 7 | 4 | 7 | 7 | 0 | 6 | 6 | 7 | 1 | 1 | 4 |
| Ducksalad | 2 | 1 | 1 | 1 | 1 | 1 | 0 | 2 | 2 | 0 | 0 | 0 | 1 | 2 | 1 | 8 | 3 | 0 | 1 | 3 | 5 | 4 | 9 | 6 |
| Giant foxtail | 3 | 3 | 3 | 2 | 2 | 0 | 0 | 0 | 0 | 0 | 1 | 0 | 0 | 2 | 6 | 8 | 4 | 0 | 3 | 4 | 4 | 4 | 8 | 9 |
| Morningglory | 3 | 8 | 1 | 3 | 7 | 2 | 0 | 1 | 1 | 1 | 1 | 1 | 2 | 8 | 8 | 9 | 2 | 0 | 9 | 6 | 2 | 1 | 8 | 7 |
| Nutsedge | 0 | 0 | 0 | 0 | 0 | 2 | 0 | 0 | 0 | 0 | 1 | 0 | — | 0 | 0 | 0 | 10 | 0 | 2 | — | — | 3 | 10 | 10 |
| Rape | 9 | 8 | 4 | 8 | 8 | 6 | 2 | 6 | 4 | 1 | 3 | 1 | 6 | 10 | 10 | 9 | 9 | 0 | 9 | 10 | 9 | 9 | 7 | 1 |

TABLE B-continued

| | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|
| Redroot pigweed | 8 | 8 | 7 | 8 | 6 | 1 | 1 | 3 | 0 | 1 | 2 | 2 | 2 | 9 | 10 | 9 | 0 | 9 | 9 | 8 | 10 | 9 |
| Rice | 2 | 1 | 1 | 1 | 1 | 1 | 1 | 0 | 0 | 0 | 0 | 0 | 1 | 4 | 4 | 5 | 0 | 1 | 3 | 2 | 3 | 3 |
| S. Flatsedge | 5 | 3 | 4 | 4 | 2 | 3 | 2 | 1 | 2 | 0 | 1 | 1 | 2 | 9 | 9 | 9 | 0 | 4 | 4 | 6 | 9 | 9 |
| Soybean | 4 | 3 | 3 | 4 | 4 | 1 | 1 | 1 | 1 | 1 | 9 | 2 | 5 | 10 | 8 | 5 | 0 | 8 | 6 | 6 | 10 | 9 |
| Sugarbeets | 9 | 9 | 10 | 10 | 9 | 10 | 8 | 9 | 8 | 0 | 7 | 7 | 10 | 10 | 10 | 10 | 0 | 10 | 8 | 8 | 10 | 9 |
| Velvetleaf | 3 | 3 | 5 | 2 | 4 | 1 | 1 | 1 | 1 | 0 | 1 | 0 | 1 | 8 | 8 | 8 | 0 | 9 | 9 | 7 | 7 | 8 |
| Wheat | 3 | 2 | 1 | 1 | 1 | 0 | 0 | 0 | 1 | 0 | 0 | 1 | 1 | 2 | 3 | 3 | 0 | 3 | 7 | 6 | 6 | 4 |
| Wild oats | 4 | 1 | 1 | 2 | 1 | 1 | 1 | 1 | 0 | 0 | 1 | 1 | 1 | 6 | 4 | 4 | 0 | 3 | 6 | 2 | 8 | 6 |

Rate 62 g/ha

| | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|
| Postemergence | | | | | | | | | | | | | | | | | | | | | | |

COMPOUND

| | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|
| B. signalgrass | 1 | 3 | 2 | 2 | 3 | 2 | 4 | 4 | 1 | 2 | 5 | 2 | 3 | 0 | 2 | 2 | 8 | 1 | 2 | 0 | 0 | 0 |
| Barnyardgrass | 1 | 2 | 3 | 1 | 2 | 1 | 1 | 2 | 0 | 3 | 3 | 2 | 1 | 1 | 2 | 2 | 4 | 0 | 2 | 0 | 0 | 0 |
| Bedstraw | 5 | 3 | 7 | 2 | 8 | 3 | 2 | 3 | 0 | 2 | 9 | 5 | 9 | 1 | — | — | 9 | 1 | 5 | 0 | 1 | 0 |
| Blackgrass | 1 | 1 | 1 | 1 | 3 | 1 | 2 | 4 | 0 | 1 | 5 | 2 | 2 | 1 | 4 | 4 | 7 | 0 | 3 | 0 | 0 | 0 |
| Cocklebur | 5 | 3 | 2 | 4 | 3 | 1 | 2 | 6 | 1 | 3 | 7 | 3 | 8 | 0 | 2 | 3 | 9 | 1 | 7 | 1 | 1 | 0 |
| Corn | 1 | 1 | 1 | 2 | 2 | 1 | 1 | 1 | 1 | 1 | 4 | 1 | 2 | 1 | 2 | 2 | 2 | 2 | 2 | 0 | 0 | 0 |
| Crabgrass | 1 | 2 | 6 | 2 | 2 | 2 | 0 | 1 | 0 | 2 | 7 | 5 | 3 | 0 | 2 | 4 | 7 | 1 | — | 0 | 1 | 0 |
| Ducksalad | 0 | 0 | 3 | 3 | 3 | 0 | 3 | 4 | 1 | 1 | 3 | 0 | 0 | 0 | 0 | 2 | 1 | 0 | 0 | 0 | 0 | 0 |
| Giant foxtail | 1 | 2 | 6 | 2 | 2 | 2 | 0 | 4 | 0 | 2 | 5 | 1 | 2 | 0 | 0 | 2 | 6 | 0 | 1 | 0 | 1 | 0 |
| Morningglory | — | 2 | 2 | 2 | 5 | 3 | 2 | 1 | — | 2 | 7 | 2 | 9 | 1 | 1 | 5 | 9 | 1 | 10 | 0 | 2 | 0 |
| Nutsedge | 0 | 0 | 0 | 0 | 0 | 0 | 0 | 2 | 0 | 2 | 0 | 0 | 2 | 0 | — | — | 0 | 0 | 0 | — | 1 | — |
| Rape | 8 | 7 | 6 | 3 | 6 | 2 | 3 | 0 | 0 | 0 | 6 | 0 | 6 | 0 | 5 | 3 | 10 | 1 | 5 | 1 | 1 | 1 |
| Redroot pigweed | 2 | 4 | 8 | 5 | 8 | 8 | 8 | 8 | 2 | 3 | 9 | 9 | 10 | 0 | 8 | 8 | 9 | 2 | 9 | 1 | 0 | 0 |
| Rice | 1 | 1 | 1 | 0 | 0 | 0 | 0 | 1 | 0 | 0 | 1 | 0 | 2 | 1 | 2 | 0 | 2 | 0 | 1 | 0 | 0 | 0 |
| S. Flatsedge | 5 | 6 | 2 | 4 | 3 | 3 | 4 | 8 | 0 | 6 | 5 | 5 | 5 | 0 | 0 | 3 | 5 | 1 | 0 | 0 | 2 | 0 |
| Soybean | 5 | 0 | 7 | 2 | 4 | 1 | 0 | 2 | 0 | 5 | 7 | 3 | 2 | 1 | 3 | 2 | 3 | 2 | 3 | 0 | 0 | 0 |
| Sugarbeets | 9 | 9 | 6 | 8 | 9 | 9 | 10 | 9 | 1 | 10 | 9 | 10 | 10 | 0 | 10 | 8 | 10 | 1 | 10 | 0 | 0 | 0 |
| Velvetleaf | 6 | 2 | 6 | 2 | 7 | 2 | 2 | 2 | 1 | 4 | 8 | 6 | 6 | 1 | 3 | 2 | 2 | 1 | 8 | 1 | 1 | 0 |
| Wheat | 1 | 1 | 1 | 1 | 3 | 1 | 2 | 2 | 1 | 2 | 3 | 2 | 8 | 0 | 4 | 3 | 4 | 1 | 2 | 0 | 0 | 0 |
| Wild oats | 1 | 1 | 1 | 2 | 3 | 1 | 3 | 3 | 1 | 2 | 5 | 2 | 3 | 0 | 2 | 2 | 6 | 1 | 3 | 0 | 0 | 0 |

Rate 62 g/ha

| | 1 | 2 | 4 | 5 | 6 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|
| Preemergence | | | | | | | | | | | | | | | | | | | | | | | | |

COMPOUND

| | 1 | 2 | 4 | 5 | 6 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|
| B. signalgrass | 9 | — | — | 3 | 1 | 8 | 1 | 2 | 3 | 7 | 0 | 9 | 0 | 3 | 0 | 0 | 0 | 2 | 5 | 9 | 2 | 1 | 0 | 0 |
| Bedstraw | 8 | 10 | — | 2 | 0 | 4 | 3 | 5 | 2 | 2 | 0 | 6 | 0 | 1 | 0 | 0 | 0 | 0 | 6 | — | 0 | 1 | 0 | 0 |
| Blackgrass | 8 | 3 | 6 | 2 | 0 | 4 | 1 | 3 | 1 | 1 | 0 | 9 | 0 | 2 | 0 | 0 | 1 | 1 | 8 | 6 | 0 | 1 | 0 | 0 |
| Cocklebur | 2 | 0 | 0 | 0 | 0 | 0 | — | 0 | 0 | 2 | 0 | — | 0 | 0 | — | 0 | 0 | 0 | 1 | 0 | 0 | 0 | 0 | 0 |
| Corn | 1 | 0 | 0 | 0 | 0 | 0 | 0 | 0 | 0 | 0 | 0 | 1 | 0 | 0 | 0 | 0 | 0 | 0 | 0 | 1 | 0 | 0 | 0 | 1 |
| Crabgrass | 10 | 9 | 3 | 7 | 1 | 9 | 5 | 7 | 4 | 1 | 0 | 9 | 0 | 3 | 0 | 0 | 0 | 3 | 7 | 0 | 1 | 0 | 0 | 2 |
| Giant foxtail | 10 | 10 | 9 | 7 | 1 | 10 | 3 | 6 | 5 | 9 | 0 | 10 | 0 | 5 | 0 | 0 | 0 | 5 | 9 | 9 | 0 | 1 | 0 | 1 |
| Morningglory | 10 | 7 | 1 | 2 | 2 | 8 | 2 | 3 | 3 | 9 | 0 | 4 | 0 | 0 | 0 | 0 | 0 | 1 | 3 | 10 | 2 | 3 | 0 | 0 |
| Nutsedge | 0 | 0 | 0 | 0 | 1 | 0 | 0 | — | 4 | 9 | 0 | 0 | 0 | 4 | 1 | 0 | 0 | 0 | 1 | 4 | 0 | 0 | 0 | 1 |
| Rape | 10 | 10 | 0 | 5 | 0 | 9 | 3 | 9 | 0 | 0 | 0 | 6 | 0 | 0 | 0 | 0 | 0 | 2 | 5 | 5 | 0 | 2 | 0 | 2 |
| Redroot pigweed | 10 | 10 | 2 | 8 | 0 | 9 | 3 | 9 | 7 | 5 | 0 | 0 | 0 | 4 | 0 | 0 | 0 | 7 | 7 | 1 | 0 | 1 | 0 | 1 |
| Soybean | 1 | 0 | 0 | 1 | 0 | 1 | 0 | 1 | 0 | 7 | 0 | 0 | 0 | 0 | 3 | 0 | 0 | 0 | 1 | 9 | 2 | 0 | 0 | 0 |
| Sugarbeets | 10 | 10 | 1 | 8 | 0 | 9 | 6 | 10 | 6 | 1 | 0 | 10 | 0 | 1 | 0 | 0 | 0 | 7 | 9 | 8 | 2 | 6 | 0 | 0 |
| Velvetleaf | 6 | 6 | — | 2 | 1 | 7 | 5 | 3 | 3 | 6 | 0 | 4 | 0 | 0 | 0 | 0 | 0 | 4 | 8 | 1 | 0 | 0 | 0 | 0 |

TABLE B-continued

| | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|
| Wheat | 1 | 1 | 0 | 1 | 0 | 1 | 0 | 0 | 0 | 1 | 0 | 0 | 0 | 0 | 0 | 0 | 0 | 0 | 0 | 2 | 0 | 0 | 0 | 0 | 0 |
| Wild oats | 8 | 6 | 2 | 3 | 0 | 5 | 0 | 0 | 1 | 3 | 0 | 2 | 0 | 2 | 2 | 0 | 1 | 4 | 7 | 7 | 0 | 0 | 1 | 0 | 0 |

Rate 62 g/ha

COMPOUND

| Preemergence | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|---|---|---|---|---|---|---|---|---|---|
| B. signalgrass | 2 | 1 | 1 | 3 | 2 | 4 | 0 | 0 | 0 | 0 | 0 | 0 | 0 | 2 | 9 | 5 | 6 | 0 | 9 | 5 | 0 | 0 | 0 | 4 | 8 |
| Bedstraw | 2 | 0 | 3 | — | 3 | 0 | 0 | 0 | 0 | 0 | 0 | 0 | — | 2 | 7 | 8 | 4 | 0 | 8 | 7 | 4 | 4 | 2 | 8 | 7 |
| Blackgrass | 2 | 1 | 0 | 1 | 1 | 1 | 0 | 0 | 0 | 0 | 0 | 0 | 0 | 7 | 6 | 2 | 5 | 0 | 8 | 3 | 4 | 3 | 3 | 7 | 5 |
| Cocklebur | 0 | 0 | 0 | 0 | 0 | 0 | 0 | 0 | 0 | 0 | 0 | 0 | 0 | 0 | 1 | 1 | 2 | 0 | 10 | 1 | 0 | 0 | 0 | 3 | 1 |
| Corn | 0 | 0 | 0 | 0 | 0 | 0 | 0 | 0 | 0 | 0 | 0 | 0 | 0 | 0 | 0 | 1 | 0 | 0 | 0 | 1 | 0 | 0 | 0 | 4 | 3 |
| Crabgrass | 2 | 2 | 1 | 1 | 1 | 0 | 0 | 0 | 0 | 0 | 0 | 0 | 0 | 8 | 9 | 8 | 4 | 0 | 9 | 8 | 5 | 5 | 6 | 10 | 9 |
| Giant foxtail | 4 | 1 | 1 | 2 | 1 | 0 | 0 | 0 | 0 | 0 | 0 | 0 | 0 | 6 | 10 | 7 | 4 | 0 | 9 | 9 | 5 | 5 | 2 | 8 | 9 |
| Morningglory | 2 | 0 | 0 | 0 | 1 | 0 | 0 | 0 | 0 | 0 | 0 | 0 | 0 | 1 | 9 | 9 | 8 | 0 | 10 | 1 | 1 | 1 | 1 | 10 | 9 |
| Nutsedge | 0 | 1 | 0 | 0 | 0 | 0 | 0 | 0 | 0 | 0 | 0 | 0 | 0 | — | 0 | 0 | 2 | 0 | — | — | — | — | — | — | 0 |
| Rape | 1 | 1 | 0 | 0 | 2 | 0 | 0 | 0 | 0 | 0 | 0 | 0 | 0 | 3 | 7 | 8 | 4 | 0 | 9 | 7 | 7 | 7 | 6 | 3 | 9 |
| Redroot pigweed | 5 | 0 | 2 | 1 | 8 | 0 | 0 | 0 | 0 | 0 | 0 | 0 | 0 | 4 | 9 | 10 | 7 | 0 | 10 | 8 | 8 | 8 | 7 | 10 | 10 |
| Soybean | 0 | 0 | 0 | 0 | 0 | 0 | 0 | 0 | 0 | 0 | 0 | 0 | 0 | 0 | 2 | 1 | 0 | 0 | 1 | 0 | 0 | 0 | 1 | 9 | 4 |
| Sugarbeets | 0 | 0 | 6 | 0 | 8 | 0 | 0 | 0 | 0 | 0 | 0 | 0 | 2 | 3 | 10 | 10 | 9 | 0 | 10 | 7 | 6 | 6 | 6 | 10 | 10 |
| Velvetleaf | 1 | 0 | 1 | 0 | 6 | 0 | 0 | 0 | 0 | 0 | 0 | 0 | 0 | 1 | 10 | 10 | 8 | 0 | 10 | 8 | 3 | 3 | 4 | 10 | 10 |
| Wheat | 0 | 0 | 0 | 0 | 0 | 0 | 0 | 0 | 0 | 0 | 0 | 0 | 0 | 1 | 1 | 1 | 0 | 0 | 1 | 2 | 1 | 1 | 1 | 0 | 2 |
| Wild oats | 3 | 0 | 1 | 0 | 2 | 0 | 0 | 0 | 0 | 0 | 0 | 0 | 0 | 4 | 4 | 6 | 6 | 0 | 6 | 9 | 2 | 2 | 3 | 4 | 3 |

Rate 62 g/ha

COMPOUND

| Preemergence | 53 | 54 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|
| B. signalgrass | 0 | 0 | 7 | 2 | 5 | 4 | 4 | 8 | 0 | 9 | 8 | 5 | 8 | 0 | 0 | 1 | 9 | 0 | 8 | 0 | 0 | 0 |
| Bedstraw | 1 | 0 | 3 | 0 | 3 | 0 | 2 | 3 | 0 | 1 | 7 | 3 | 7 | 0 | — | 0 | 2 | 0 | 3 | — | — | 0 |
| Blackgrass | 0 | 0 | 2 | 1 | 1 | 1 | 2 | 5 | 0 | 3 | 3 | 3 | 1 | 0 | 1 | 1 | 8 | 0 | 3 | 0 | 0 | 0 |
| Cocklebur | 0 | — | 0 | 0 | 0 | 0 | 1 | 1 | 0 | 0 | — | 0 | 0 | 0 | — | 0 | 0 | 0 | 0 | 0 | 0 | 0 |
| Corn | 0 | 0 | 0 | 0 | 1 | 0 | 0 | 0 | 0 | 0 | 4 | 0 | 0 | 0 | 1 | 3 | 1 | 0 | 0 | 0 | 0 | 0 |
| Crabgrass | — | 0 | 8 | 0 | 3 | 2 | 3 | 9 | 0 | 6 | 6 | 3 | 6 | 0 | 2 | 6 | 10 | 0 | 6 | 0 | 0 | 0 |
| Giant foxtail | 1 | 1 | 8 | 2 | 8 | 1 | 2 | 1 | 0 | 0 | 7 | 3 | 4 | 0 | 1 | 5 | 10 | 0 | 1 | 0 | 0 | 0 |
| Morningglory | 1 | 0 | 6 | 1 | — | 1 | 2 | 4 | 0 | 2 | 8 | 3 | 8 | 0 | 2 | 2 | 3 | 0 | 6 | 0 | 0 | 0 |
| Nutsedge | 0 | 0 | 0 | 0 | 0 | 0 | 0 | 0 | 0 | 0 | — | 0 | 0 | 0 | — | — | 0 | 0 | 0 | 0 | 0 | 0 |
| Rape | 2 | 0 | 5 | 0 | 4 | 0 | 3 | 3 | 0 | 7 | 7 | 2 | 0 | 0 | 2 | 4 | 0 | 0 | 2 | 0 | 0 | 0 |
| Redroot pigweed | 0 | 1 | 8 | 6 | 8 | 8 | 8 | 9 | 0 | 0 | 9 | 8 | 7 | 0 | 6 | 7 | 9 | 0 | 9 | 0 | 0 | 0 |
| Soybean | 0 | 0 | 0 | 0 | 0 | 0 | 0 | 0 | 0 | 0 | 1 | 0 | 0 | 0 | 0 | 0 | 0 | 0 | 0 | 0 | 0 | 0 |
| Sugarbeets | 4 | 0 | 10 | 6 | 10 | 8 | 10 | 9 | 0 | 9 | 9 | 9 | 9 | 0 | 2 | 8 | 9 | 0 | 9 | 0 | 0 | 0 |
| Velvetleaf | 0 | 0 | 7 | 1 | 9 | 1 | 2 | 4 | 0 | 1 | 8 | 2 | 0 | 0 | 0 | 3 | 2 | 0 | 2 | 0 | 0 | 0 |
| Wheat | 0 | 0 | 1 | 0 | 1 | 0 | 2 | 2 | 0 | 0 | 3 | 1 | 1 | 0 | — | 0 | 2 | 0 | 0 | 0 | 0 | 0 |
| Wild oats | 0 | 0 | 7 | 0 | 4 | 1 | 3 | 3 | 0 | 2 | 3 | 4 | 4 | 0 | 0 | 1 | 7 | 0 | 5 | 0 | 0 | 0 |

Test C

Compounds evaluated in this test were formulated in a non-phytotoxic solvent mixture which included a surfactant and applied to plants that were grown for various periods of time before treatment (postemergence application) using a sandy loam soil mixture.

Plantings of these crops and weed species were adjusted to produce plants of appropriate size for the postemergence test. All plant species were grown using normal greenhouse practices. Crop and weed species include arrowleaf sida (*Sida rhombifolia*), barnyardgrass (*Echinochloa crus-galli*), cocklebur (*Xanthium strumarium*), common ragweed (*Ambrosia elatior*), corn (*Zea mays*), cotton (*Gossypium hirsutum*), eastern black nightshade (*Solanum ptycanthum*), fall panicum (*Panicum dichotomiflorum*), field bindweed (*Convolvulus arvensis*), giant foxtail (*Setaria faberii*), hairy beggarticks (*Bidens pilosa*), ivyleaf morningglory (*Ipomoea hederacea*), johnsongrass (*Sorghum halepense*), ladysthumb smartweed (*Polygonum persicaria*), lambsquarters (*Chenopodium album*), large crabgrass (*Digitaria sanguinalis*), purple nutsedge (*Cyperus rotundus*), redroot pigweed (*Amaranthus retroflexus*), soybean (*Glycine max*), surinam grass (*Brachiaria decumbens*), velvetleaf (*Abutilon theophrasti*) and wild poinsettia (*Euphorbia heterophylla*).

Treated plants and untreated controls were maintained in a greenhouse for approximately 14 to 21 days, after which all treated plants were compared to untreated controls and visually evaluated. Plant response ratings, summarized in Table C, were based upon a 0 to 100 scale where 0 was no effect and 100 was complete control. A dash response (−) means no test result.

TABLE C

| PREEMERGENCE | COMPOUND | | | | | | | | | | | |
|---|---|---|---|---|---|---|---|---|---|---|---|---|
| | 1 | 2 | 3 | 9 | 15 | 21 | 23 | 42 | 43 | 46 | 52 | 66 |
| Rate 140 g/ha | | | | | | | | | | | | |
| Arrowleaf sida | 100 | 100 | 0 | 95 | 85 | 90 | 100 | 100 | 100 | 100 | 100 | 100 |
| Barnyardgrass | 100 | 30 | 0 | 50 | 85 | 5 | 10 | 100 | 50 | 50 | 40 | 5 |
| Cocklebur | 0 | 10 | 0 | 0 | 5 | 0 | 5 | 60 | — | 5 | 20 | 0 |
| Common ragweed | 100 | 50 | 0 | 75 | 75 | 20 | 90 | 85 | 50 | 80 | 100 | 30 |
| Corn | 10 | 30 | 0 | 10 | 10 | 0 | 5 | 5 | 55 | 5 | 50 | 0 |
| Cotton | 100 | 15 | 0 | 50 | 10 | 20 | 75 | 60 | 10 | 40 | 70 | 0 |
| E. blacknightsh | 95 | 90 | 0 | 95 | 95 | 85 | 100 | 95 | 100 | 100 | 100 | 30 |
| Fall panicum | 95 | 100 | 0 | 100 | 100 | 90 | 100 | 100 | 100 | 100 | 100 | 100 |
| Field bindweed | 50 | 100 | 0 | 90 | 100 | 40 | 100 | 100 | 100 | 100 | 100 | 90 |
| Giant foxtail | 100 | 100 | 0 | 100 | 100 | 100 | 100 | 100 | 100 | 100 | 100 | 0 |
| H. beggarticks | 100 | 100 | 0 | 85 | — | 40 | 100 | 90 | 100 | 100 | 30 | 0 |
| I. morningglory | 20 | 5 | 0 | 50 | 65 | 0 | 40 | 100 | 100 | 50 | 100 | 10 |
| Johnsongrass | 100 | 60 | 0 | 95 | 100 | 5 | 80 | 85 | 30 | 50 | 80 | 10 |
| Ladysthumb | 95 | — | — | 90 | 90 | 5 | 80 | 95 | — | 50 | — | 70 |
| Lambsquarters | 100 | 100 | 0 | 100 | 60 | 90 | 100 | 100 | 100 | 100 | 100 | 100 |
| Large crabgrass | 100 | 100 | 0 | 100 | 100 | 100 | 100 | 100 | 100 | 100 | 100 | 100 |
| Purple nutsedge | 0 | 0 | 0 | 0 | 0 | 0 | 0 | 0 | 0 | — | 10 | 0 |
| Redroot pigweed | 100 | 100 | 0 | 100 | 100 | 100 | 100 | 100 | 100 | 100 | 100 | 100 |
| Soybean | 0 | 40 | 0 | 25 | 10 | 5 | 10 | 35 | 55 | 20 | 70 | 0 |
| Surinam grass | 95 | 35 | 0 | 90 | 80 | 10 | 60 | 70 | 10 | 25 | 70 | 20 |
| Velvetleaf | 100 | 50 | 0 | 100 | 70 | 50 | 50 | 95 | 100 | 80 | 100 | 0 |
| Wild poinsettia | 50 | 45 | 0 | 50 | 20 | 5 | 10 | 85 | 60 | 20 | 100 | 0 |
| Rate 70 g/ha | | | | | | | | | | | | |
| Arrowleaf sida | 95 | 20 | 0 | 95 | 85 | 85 | 100 | 95 | 100 | 90 | 100 | 5 |
| Barnyardgrass | 75 | 5 | 0 | 50 | 35 | 0 | 5 | 10 | 30 | 10 | 40 | 5 |
| Cocklebur | 0 | — | 0 | 0 | 0 | 0 | — | — | — | 10 | 0 | 0 |
| Common ragweed | 100 | 0 | 0 | 95 | 20 | 0 | 30 | 85 | 40 | 20 | 60 | 0 |
| Corn | 10 | 0 | 0 | 5 | 5 | 0 | 0 | 5 | 30 | 0 | 45 | 0 |
| Cotton | 60 | 5 | 0 | 35 | 10 | 5 | 75 | 60 | 0 | 5 | 0 | 0 |
| E. blacknightsh | 90 | 5 | 0 | 100 | 95 | 80 | 100 | 95 | 100 | 100 | 80 | 10 |
| Fall panicum | 90 | 5 | 0 | 90 | 80 | 0 | 100 | 85 | 100 | 100 | 100 | 80 |
| Field bindweed | 50 | 30 | 0 | 100 | 100 | 40 | 100 | 100 | 100 | 70 | 100 | 80 |
| Giant foxtail | 100 | 5 | 0 | 100 | 100 | 100 | 100 | 80 | 100 | 100 | 85 | 0 |
| H. beggarticks | 100 | 40 | 0 | 85 | — | 0 | 50 | — | 5 | 100 | 0 | 0 |
| I. morningglory | 15 | 5 | 0 | 50 | 20 | 0 | — | 70 | 100 | 50 | 100 | 10 |
| Johnsongrass | 95 | 5 | 0 | 85 | 85 | 0 | 20 | 70 | 30 | 45 | 50 | 5 |
| Ladysthumb | 90 | 30 | — | 85 | 20 | — | 80 | 85 | — | 10 | — | — |
| Lambsquarters | 100 | — | 0 | 100 | 20 | 5 | 100 | 100 | 100 | 100 | 100 | 0 |
| Large crabgrass | 100 | 5 | 0 | 100 | 100 | 100 | 100 | 100 | 100 | 100 | 100 | 100 |
| Purple nutsedge | 0 | 0 | 0 | 0 | 0 | 0 | 0 | 0 | 0 | — | 5 | 0 |
| Redroot pigweed | 100 | 5 | 0 | 100 | 85 | 80 | 100 | 100 | 100 | 100 | 100 | 100 |
| Soybean | 0 | 0 | 0 | 20 | 10 | 0 | 5 | 5 | 5 | 0 | 55 | 0 |
| Surinam grass | 90 | 10 | 0 | 80 | 50 | 5 | 45 | 55 | 5 | 5 | 40 | 5 |
| Velvetleaf | 75 | 5 | 0 | 95 | 20 | 50 | — | 80 | 100 | 80 | 100 | 0 |
| Wild poinsettia | 10 | 5 | 0 | 50 | 0 | 5 | 5 | 30 | 50 | 15 | 40 | 0 |
| Rate 35 g/ha | | | | | | | | | | | | |
| Arrowleaf sida | 85 | 10 | 0 | 90 | 80 | 70 | 80 | 95 | 100 | 100 | 100 | 5 |

TABLE C-continued

| | | | | | | | | | | | | |
|---|---|---|---|---|---|---|---|---|---|---|---|---|
| Barnyardgrass | 20 | 0 | 0 | 10 | 10 | 0 | 0 | 5 | 10 | 5 | 30 | 0 |
| Cocklebur | 0 | 0 | 0 | 0 | 0 | 0 | — | 0 | 0 | 0 | — | 0 |
| Common ragweed | 80 | 0 | 0 | 80 | 10 | 0 | 10 | 20 | 0 | 10 | 40 | 0 |
| Corn | 5 | 0 | 0 | 0 | 0 | 0 | 0 | 5 | 0 | 0 | 0 | 0 |
| Cotton | 30 | 0 | 0 | 10 | 5 | 0 | 5 | 30 | 0 | 0 | 0 | 0 |
| E. blacknightsh | 90 | 5 | 0 | 95 | 70 | 40 | 95 | 90 | 100 | 80 | 40 | 0 |
| Fall panicum | 90 | 0 | 0 | 85 | 40 | 10 | 55 | 50 | 100 | 60 | 100 | 80 |
| Field bindweed | 65 | 0 | 0 | 50 | 65 | — | 20 | 95 | 100 | 10 | 100 | 40 |
| Giant foxtail | 100 | 0 | 0 | 90 | 70 | 85 | 85 | 70 | 100 | 100 | 70 | 0 |
| H. beggarticks | 20 | 40 | 0 | 85 | — | 0 | 50 | 0 | 0 | 0 | 0 | 0 |
| I. morningglory | 15 | 0 | 0 | 20 | 15 | 0 | 5 | 30 | 20 | 45 | 5 | 5 |
| Johnsongrass | 50 | 5 | 0 | 65 | 35 | 0 | 5 | 70 | 10 | 5 | 40 | 0 |
| Ladysthumb | 25 | — | — | 35 | 0 | 0 | 5 | 90 | — | 25 | — | 0 |
| Lambsquarters | 100 | 0 | 0 | 95 | 0 | 0 | 60 | 85 | 100 | 60 | 100 | 0 |
| Large crabgrass | 100 | 0 | 0 | 95 | 100 | 80 | 100 | 80 | 100 | 80 | 100 | 80 |
| Purple nutsedge | 0 | 0 | 0 | 0 | 0 | 0 | 0 | 0 | 0 | — | 0 | 0 |
| Redroot pigweed | 100 | 5 | 0 | 100 | 60 | — | 100 | 100 | 100 | 70 | 100 | 100 |
| Soybean | 0 | 0 | 0 | 20 | 0 | 0 | 5 | 0 | 0 | 0 | 0 | 0 |
| Surinam grass | 50 | 0 | 0 | 35 | 20 | 0 | 5 | 50 | 0 | 0 | 5 | 5 |
| Velvetleaf | 20 | 0 | 0 | 75 | 5 | 0 | 50 | 40 | 100 | 50 | 70 | 0 |
| Wild poinsettia | 0 | 0 | 0 | 10 | 0 | 0 | 5 | 25 | 10 | 0 | — | 0 |

| | COMPOUND | | |
|---|---|---|---|
| POSTEMERGENCE | Rate 140 g/ha 9 | Rate 70 g/ha 9 | Rate 35 g/ha 9 |
| Arrowleaf sida | 90 | 90 | 80 |
| Barnyardgrass | 25 | 25 | 10 |
| Cocklebur | 80 | 80 | 60 |
| Common ragweed | 10 | 30 | — |
| Corn | 15 | 15 | 10 |
| Cotton | 90 | 80 | 70 |
| E. blacknightsh | 100 | — | 100 |
| Fall panicum | 30 | 20 | 5 |
| Field bindweed | 80 | 70 | 60 |
| Giant foxtail | 30 | 15 | 15 |
| H. beggarticks | 80 | 70 | 65 |
| I. morningglory | 100 | 60 | 50 |
| Johnsongrass | 50 | — | 10 |
| Ladysthumb | 30 | 30 | 20 |
| Lambsquarters | 100 | 80 | 75 |
| Large crabgrass | 50 | 40 | 20 |
| Purple nutsedge | 5 | 5 | 5 |
| Redroot pigweed | — | 70 | 60 |
| Soybean | 50 | 50 | 40 |
| Surinam grass | 20 | 5 | 5 |
| Velvetleaf | 90 | 70 | 10 |
| Wild poinsettia | 100 | 90 | 90 |

Test D

Compounds evaluated in this test were formulated in a non-phytotoxic solvent mixture which included a surfactant and applied to plants that were in the 1- to 4-leaf stage (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grown using normal greenhouse practices. Crop and weed species include alfalfa (*Medicago sativa*), annual bluegrass (*Poa annua*), blackgrass (*Alopecurus myosuroides*), black nightshade (*Solanum nigra*), chickweed (*Stellaria media*), common poppy (*Papaver rhoeas*), deadnettle (*Lamium amplexicaule*), downy brome (*Bromus tectorum*), field violet (*Viola arvensis*), galium 2 (*Galium aparine*), green foxtail (*Setaria viridis*), Italian ryegrass (*Lolium multiflorum*), jointed goatgrass (*Aegilops cylindrica*), kochia (*Kochia scoparia*), lambsquarters (*Chenopodium album*), lentil (*Lens culinaris*), littleseed canarygrass (*Phalaris minor*), pea (*Pisum sativum*), potato (*Solanum tuberosum*), rape (*Brassica napus*), redroot pigweed (*Amaranthus retroflexus*), Russian thistle (*Salsola kali*), scentless chamomile (*Matricaria inodora*), sorghum (*Sorghum vulgare*), spring barley (*Hordeum vulgare*), sugar beet (*Beta vulgaris*), sunflower (*Helianthus annuus*), ivyleaf speedwell (*Veronica hederaefolia*), spring wheat (*Triticum aestivum*), winter wheat (*Triticum aestivum*), wild buckwheat (*Polygonum convolvulus*), wild mustard (*Sinapis arvensis*), wild oat (*Avena fatua*), windgrass (*Apera spica-venti*) and winter barley (*Hordeum vulgare*).

Treated plants and untreated controls were maintained in a greenhouse for approximately 21 to 28 days, after which all treated plants were compared to untreated controls and visually evaluated. Plant response ratings, summarized in Table D, are based upon a 0 to 100 scale where 0 is no effect and 100 is complete control. A dash response (–) means no test result.

TABLE D

| | COMPOUND | | | | | | | | | | | | | |
|---|---|---|---|---|---|---|---|---|---|---|---|---|---|---|
| | Rate 250 g/ha | | Rate 125 g/ha | | | Rate 62 g/ha | | | | | Rate 31 g/ha | | | |
| PREEMERGENCE | 1 | 22 | 1 | 22 | 52 | 1 | 22 | 46 | 51 | 52 | 1 | 46 | 51 | 52 |
| Alfalfa | — | — | — | — | — | — | — | — | — | — | — | — | — | — |
| Annual bluegras | 85 | 50 | 100 | 100 | 100 | 60 | 20 | 90 | 100 | 100 | 75 | 60 | 85 | 50 |
| Barley (winter) | 40 | 10 | 30 | 20 | 60 | 20 | 0 | 2 | 90 | 50 | 10 | 50 | 50 | 50 |
| Blackgrass | 70 | 40 | 60 | 60 | 90 | 50 | 30 | 60 | 80 | 80 | 30 | 10 | 60 | 50 |
| Blk nightshade | 100 | 50 | 100 | 60 | 90 | 90 | 10 | 50 | 95 | 40 | 55 | 50 | 100 | 10 |
| Chickweed | 90 | 30 | 85 | 70 | 85 | 85 | 40 | 70 | 90 | 80 | 55 | 70 | 80 | 30 |
| Common poppy | 100 | 70 | 100 | 70 | — | 100 | 60 | 100 | 100 | — | 80 | 100 | 100 | — |
| Deadnettle | 90 | 10 | 85 | 70 | 90 | 65 | 0 | 90 | 80 | 70 | 60 | 90 | 80 | 50 |
| Downy brome | 100 | 10 | 60 | 100 | 50 | 50 | 0 | 70 | 80 | 40 | 30 | 70 | 80 | 30 |
| Field violet | 85 | — | 85 | — | — | 70 | — | 100 | 65 | — | 20 | 85 | 65 | — |
| Galium | 100 | 30 | 100 | 100 | — | 100 | 20 | 60 | 100 | — | 20 | 60 | 100 | — |
| Green foxtail | 100 | 100 | 100 | 100 | 100 | 100 | 10 | 100 | 100 | 80 | 60 | 80 | 100 | 50 |
| I. Ryegrass | 100 | 75 | 100 | 65 | 70 | 40 | 0 | 60 | 90 | 70 | 10 | 60 | 60 | 30 |
| Jointed goatgra | 50 | 10 | 70 | 20 | 40 | 20 | 0 | 60 | 90 | 40 | 10 | 50 | 60 | 30 |
| Kochia | 85 | 60 | 100 | 65 | 100 | 100 | 10 | 60 | 80 | 80 | 40 | 60 | 85 | 50 |
| Lambsquarters | 70 | 70 | 70 | 70 | 100 | 70 | 60 | 70 | 70 | 90 | 10 | 65 | 70 | 90 |
| Lentil | — | — | — | — | — | — | — | — | — | — | — | — | — | — |
| LS canarygrass | 70 | 50 | 85 | 60 | 90 | 60 | 20 | 90 | 90 | 60 | 20 | 70 | 80 | 30 |
| Pea | — | — | — | — | — | — | — | — | — | — | — | — | — | — |
| Potato | — | — | — | — | — | — | — | — | — | — | — | — | — | — |
| Rape | 100 | 50 | 100 | 100 | 100 | 75 | 20 | 100 | 100 | 60 | 30 | 50 | 100 | 50 |
| Redroot pigweed | 70 | 70 | 75 | 100 | 100 | 70 | 60 | 70 | 70 | 90 | 75 | 70 | 70 | 90 |
| Russian thistle | 100 | — | — | — | 85 | 100 | — | 30 | 70 | 85 | 10 | 30 | 60 | 30 |
| Scentless chamo | 85 | 70 | 75 | 70 | — | 70 | 60 | 70 | 70 | — | 30 | 65 | 65 | — |
| Sorghum | — | — | — | — | — | — | — | — | — | — | — | — | — | — |
| Spring Barley | 40 | 2 | 20 | 10 | 80 | 20 | 0 | 5 | 80 | 60 | 10 | 30 | 70 | 50 |
| Spring Wheat | — | 5 | 0 | 10 | 70 | 0 | 0 | 10 | 70 | 70 | 0 | 30 | 60 | 60 |
| Sugar beet | 100 | 80 | 85 | 100 | 100 | 100 | 30 | 100 | 100 | 100 | 30 | 70 | 100 | 100 |
| Sunflower | 30 | 30 | 50 | 10 | 0 | 35 | 20 | 30 | 40 | 0 | 10 | 10 | 40 | 0 |
| Ivyleaf speedwe | 100 | — | 100 | — | — | 100 | — | 100 | 100 | — | 50 | 100 | 100 | — |
| Wheat (spring) | 30 | — | 50 | — | — | 10 | — | — | — | — | 10 | — | — | — |
| Wheat (winter) | 40 | 5 | 20 | 10 | 60 | 10 | 0 | 2 | 55 | 60 | 10 | 40 | 30 | 50 |
| Wild buckwheat | 85 | 30 | 85 | 55 | 100 | 80 | 0 | 40 | 90 | 60 | 40 | 40 | 90 | 40 |
| Wild mustard | 98 | 30 | 100 | 60 | 100 | 100 | 30 | 100 | 100 | 90 | 60 | 90 | 100 | 90 |
| Wild oat | 90 | 30 | 60 | 30 | 60 | 60 | 0 | 70 | 95 | 50 | 20 | 50 | 80 | 40 |
| Windgrass | 100 | 30 | 100 | 70 | 100 | 100 | 20 | 100 | 100 | 100 | 60 | 40 | 100 | 80 |

| | COMPOUND | | | | | | | | | |
|---|---|---|---|---|---|---|---|---|---|---|
| | Rate 125 g/ha | | | Rate 62 g/ha | | | Rate 31 g/ha | | Rate 16 g/ha | |
| POSTEMERGENCE | 1 | 22 | 52 | 1 | 22 | 52 | 1 | 52 | 1 | 52 |
| Annual bluegras | — | 70 | 50 | 50 | 30 | 20 | 50 | 20 | 20 | 10 |
| Barley (winter) | 10 | 10 | 10 | 10 | 10 | 10 | 10 | 10 | 5 | 10 |
| Blackgrass | 30 | 20 | 10 | 10 | 10 | 10 | 10 | 10 | 10 | 10 |
| Blk nightshade | 50 | 100 | 65 | 50 | 90 | 65 | — | 60 | 60 | 55 |
| Chickweed | 70 | 100 | 80 | 80 | 60 | 70 | — | 50 | 80 | 30 |
| Common poppy | 100 | 100 | 100 | 100 | 100 | 100 | 100 | 100 | 50 | 60 |
| Deadnettle | 70 | 90 | 98 | 70 | 50 | 100 | 70 | 100 | 85 | 45 |
| Downy brome | 10 | 20 | 20 | 10 | 10 | 20 | 10 | 20 | 2 | 10 |
| Field violet | 80 | 100 | — | 100 | 100 | — | 100 | — | 20 | — |
| Galium | 70 | 90 | 60 | 70 | 70 | 65 | 60 | 50 | 0 | 40 |
| Green foxtail | 20 | 35 | 30 | 20 | 10 | 10 | 10 | 10 | 5 | 10 |
| I. Ryegrass | 10 | 10 | 10 | 10 | 10 | 10 | 10 | 10 | 5 | 5 |
| Jointed goatgra | 10 | 15 | 10 | 10 | 10 | 10 | 10 | 10 | 5 | 10 |
| Kochia | 70 | 70 | 70 | 80 | 50 | 70 | 60 | 70 | 0 | 70 |
| Lambsquarters | 50 | 60 | 80 | 60 | 60 | 80 | 60 | 80 | 0 | 70 |
| LS canarygrass | 20 | 60 | 20 | 20 | 20 | 10 | 10 | 10 | 10 | 10 |
| Rape | 85 | 90 | 85 | 100 | 90 | 98 | 100 | 65 | 65 | 65 |
| Redroot pigweed | 50 | 70 | 70 | 70 | 50 | 60 | 70 | 60 | 0 | 45 |
| Russian thistle | 50 | 80 | — | 60 | 80 | — | — | — | 40 | — |
| Scentless chamo | 60 | 80 | 70 | 60 | 50 | 60 | 60 | 50 | 30 | 30 |
| Spring Barley | 10 | 20 | 10 | 10 | 10 | 10 | 10 | 10 | 5 | 10 |
| Spring Wheat | 20 | 20 | 10 | 10 | 10 | 10 | 10 | 10 | 5 | 10 |
| Sugar beet | 100 | 100 | 100 | 90 | 100 | 100 | 75 | 100 | 45 | 100 |
| Sunflower | 20 | 20 | 70 | 20 | 10 | 50 | 10 | 20 | 5 | 40 |
| Wheat (winter) | 10 | 10 | 10 | 10 | 10 | 10 | 10 | 10 | 5 | 10 |
| Wild buckwheat | 20 | 20 | 80 | 0 | 20 | 70 | 0 | 50 | 0 | 60 |
| Wild mustard | 100 | 100 | 100 | 100 | 100 | 98 | 100 | 70 | 85 | 60 |
| Wild oat | 30 | 65 | 10 | 20 | 20 | 10 | 20 | 10 | 5 | 10 |
| Windgrass | 30 | — | 50 | — | 30 | 20 | 20 | 10 | 5 | 10 |

Test E

Seeds, tubers, or plant parts of alexandergrass (*Brachiaria plantaginea*), annual bluegrass (*Poa annua*), arrowleaf sida (*Sida rhombifolia*), barnyardgrass (*Echinochloa crus-galli*), bermudagrass (*Cynodon dactylon*), citrus (*Citrus sinensis*), common chickweed (*Stellaria media*), common purslane (*Portulaca oleracea*), common ragweed (*Ambrosia elatior*), common groundsel (*Senecio vulgaris*), dallisgrass (*Paspalum dilatatum*), goosegrass (*Eleusine indica*), green foxtail (*Setaria viridis*), guineagrass (*Panicum maximum*), itchgrass (*Rottboellia exaltata*), johnson grass (*Sorghum halepense*), kochia (*Kochia scoparia*), large crabgrass (*Digitaria sanguinalis*), leafy spurge (*Euphorbia esula*), pitted morningglory (*Ipomoea lacunosa*), purple nutsedge (*Cyperus rotundus*), quackgrass (*Agropyron repens*), Russian thistle (*Salsola kali*), sandbur (*Cenchrus echinatus*), sourgrass (*Trichachne insularis*), Spanishneedles (*Bidens bipinnata*), sugarcane (*Saccharum officinarum*), surinam grass (*Brachiaria decumbens*) and tall mallow (*Malva sylvestris*) were planted into greenhouse pots of flats containing greenhouse planting medium. Plant species were grown grown in separate pots or individual compartments. Preemergence applications were made within one day of planting the seed or plant part. Postemergence applications were applied when the plants were in the two to four leaf stage (three to twenty cm).

Test chemicals were formulated in a non-phytotoxic solvent mixture which included a surfactant and applied preemergence to the soil surface, postemergence to the plants or as a post directed spray to plants and soil at the base of the target species. Untreated control plants and treated plants were placed in the greenhouse and visually evaluated for injury 13 to 21 days after herbicide application. Plant response ratings, summarized in Table E, are based on a 0 to 100 scale where 0 is no injury and 100 is complete control. A dash (–) response means no test result.

TABLE E

| | COMPOUND | | | | | | | | | |
|---|---|---|---|---|---|---|---|---|---|---|
| | Rate 500 g/ha | Rate 250 g/ha | | | | | | | | |
| PREEMERGENCE | 2 | 1 | 2 | 9 | 15 | 23 | 42 | 44 | 46 | 67 |
| A. bluegrass | — | — | 100 | — | 100 | — | — | — | — | — |
| Alexandergrass | 100 | 100 | 100 | 100 | 100 | 98 | 90 | 50 | 60 | 95 |
| Arrowleaf sida | — | — | 100 | — | 100 | — | — | — | — | — |
| B. signalgrass | — | — | 100 | — | 98 | — | — | — | — | — |
| Barnyardgrass | — | — | 100 | — | 75 | — | — | — | — | — |
| Bermudagrass | 100 | 100 | 100 | 100 | 98 | 98 | 98 | 100 | 100 | 100 |
| Com. purslane | 100 | 100 | 100 | 100 | 100 | 100 | 100 | 100 | 100 | 100 |
| Com. ragweed | 100 | 100 | 100 | 100 | 100 | 100 | 90 | 100 | 100 | 100 |
| Com. chickweed | — | — | 100 | — | 100 | — | — | — | — | — |
| Com. groundsel | 100 | 100 | 100 | 100 | 100 | 100 | 100 | 100 | 100 | 100 |
| Dallisgrass | 100 | 100 | 100 | 100 | 100 | 100 | 100 | 100 | 100 | 100 |
| Goosegrass | 100 | 100 | 100 | 100 | 100 | 100 | 100 | 100 | 100 | 100 |
| Green foxtail | — | — | 100 | — | 100 | — | — | — | — | — |
| Guineagrass | — | 100 | 100 | 100 | 100 | 100 | 100 | 100 | 98 | 100 |
| Itchgrass | 100 | 95 | 95 | 100 | 80 | 70 | 70 | 40 | 40 | 80 |
| Johnsongrass | 100 | 100 | 100 | 90 | 100 | 90 | 95 | 75 | 0 | 80 |
| Kochia | — | — | — | — | 100 | — | — | — | — | — |
| Large crabgrass | 100 | 100 | 100 | 100 | 100 | 100 | 100 | 60 | 100 | 100 |
| Leafy spurge | — | — | 100 | — | 98 | — | — | — | — | — |
| P. morninglory | 100 | 100 | 100 | 100 | 90 | 80 | 75 | 50 | 65 | 90 |
| Purple nutsedge | 0 | 50 | 0 | 0 | 0 | 0 | 30 | 0 | 0 | 10 |
| Quackgrass | — | — | 100 | — | 95 | — | — | — | — | — |
| Russian Thistle | — | — | — | — | 95 | — | — | — | — | — |
| Sandbur | 100 | 100 | 100 | 20 | 100 | 98 | 70 | 80 | 30 | 75 |
| Sourgrass | 100 | 100 | 100 | 100 | 100 | 100 | 100 | 100 | 100 | 100 |
| Spanishneedles | 100 | 100 | 100 | 60 | 100 | 100 | 90 | 98 | 90 | 50 |
| Sugarcane | — | — | — | — | 10 | — | — | — | — | — |
| Surinam grass | 100 | 100 | 100 | 100 | 100 | — | 100 | — | 55 | 100 |
| Tall Mallow | 100 | 100 | 100 | 100 | 98 | 90 | 100 | 98 | 100 | 98 |

| | COMPOUND | | | | | | | | | |
|---|---|---|---|---|---|---|---|---|---|---|
| | Rate 125 g/ha | | | | | | | | | |
| PREEMERGENCE | 1 | 2 | 9 | 15 | 23 | 42 | 44 | 46 | 52 | 67 |
| A. bluegrass | 100 | 100 | — | 100 | — | — | — | — | — | — |
| Alexandergrass | 90 | 100 | 65 | 100 | 85 | 90 | 40 | 60 | 75 | 70 |
| Arrowleaf sida | 100 | 100 | — | 100 | — | — | — | — | — | — |
| B. signalgrass | 100 | 100 | — | 95 | — | — | — | — | — | — |
| Barnyardgrass | 80 | 100 | — | 40 | — | — | — | — | — | — |
| Bermudagrass | 100 | 100 | 100 | 98 | 98 | 98 | 98 | 100 | 100 | 90 |
| Com. purslane | 100 | 100 | 100 | 100 | 100 | 100 | 100 | 100 | 100 | 100 |
| Com. ragweed | 100 | 100 | 98 | 98 | 100 | 90 | 98 | 98 | 100 | 100 |
| Com. chickweed | 100 | 100 | — | 98 | — | — | — | — | — | — |
| Com. groundsel | 100 | 100 | 100 | 100 | 100 | 100 | 100 | 100 | 100 | 95 |
| Dallisgrass | 100 | 100 | 100 | 100 | 90 | 100 | 90 | 100 | 90 | 80 |
| Goosegrass | 100 | 100 | 100 | 98 | 98 | 100 | 98 | 98 | 100 | 100 |
| Green foxtail | 100 | 100 | — | 100 | — | — | — | — | 100 | — |
| Guineagrass | 100 | 100 | 90 | 100 | 98 | 100 | 100 | 100 | 100 | 100 |

TABLE E-continued

| | | | | | | | | | | |
|---|---|---|---|---|---|---|---|---|---|---|
| Itchgrass | 50 | 75 | 100 | 60 | 70 | 80 | 30 | 40 | 80 | 65 |
| Johnsongrass | 90 | 85 | 85 | 90 | 80 | 90 | 60 | 0 | 75 | 50 |
| Kochia | 100 | — | — | 95 | — | — | — | — | — | — |
| Large crabgrass | 100 | 100 | 100 | 100 | 100 | 100 | 70 | 100 | 100 | 98 |
| Leafy spurge | 100 | 100 | — | — | — | — | — | — | — | — |
| P. morninglory | 100 | 100 | 75 | 75 | 50 | 65 | 50 | 65 | 100 | 90 |
| Purple nutsedge | 0 | 0 | 0 | 0 | 0 | 30 | 0 | 0 | 50 | 5 |
| Quackgrass | 100 | 100 | — | 95 | — | — | — | — | — | — |
| Russian Thistle | — | — | — | 95 | — | — | — | — | — | — |
| Sandbur | 95 | 90 | 10 | 50 | 80 | 70 | 70 | 10 | 50 | 65 |
| Sourgrass | 100 | 100 | 100 | 100 | 100 | 100 | 100 | 100 | 100 | 100 |
| Spanishneedles | 90 | 100 | 30 | 98 | 100 | 100 | 70 | 90 | 35 | 50 |
| Sugarcane | — | — | — | 10 | — | — | — | — | — | — |
| Surinam grass | 98 | 100 | 20 | 100 | — | 100 | — | 40 | 80 | 75 |
| Tall Mallow | 100 | 100 | 100 | 100 | 85 | 98 | 98 | 100 | 100 | 90 |

| | COMPOUND Rate 64 g/ha | | | | | | | | | |
|---|---|---|---|---|---|---|---|---|---|---|
| PREEMERGENCE | 1 | 2 | 9 | 15 | 23 | 42 | 44 | 46 | 52 | 67 |
| A. bluegrass | 100 | 100 | — | 100 | — | — | — | — | — | — |
| Alexandergrass | 75 | 90 | 65 | 80 | 0 | 40 | 40 | 0 | 75 | 40 |
| Arrowleaf sida | 98 | 100 | — | 50 | — | — | — | — | — | — |
| B. signalgrass | 90 | 100 | — | 60 | — | — | — | — | — | — |
| Barnyardgrass | 70 | 95 | — | 0 | — | — | — | — | — | — |
| Bermudagrass | 100 | 100 | 98 | 98 | 98 | 95 | 80 | 98 | 90 | 90 |
| Com. purslane | 100 | 100 | 100 | 100 | 100 | 100 | 100 | 100 | 100 | 100 |
| Com. ragweed | 100 | 100 | 100 | 100 | 70 | 75 | 85 | 98 | 80 | 95 |
| Com. chickweed | 95 | 100 | — | 85 | — | — | — | — | — | — |
| Com. groundsel | 100 | 100 | 100 | 98 | 100 | 100 | 100 | 100 | 98 | 50 |
| Dallisgrass | 100 | 100 | 100 | 100 | 85 | 95 | 80 | 98 | 80 | 70 |
| Goosegrass | 100 | 100 | 100 | 98 | 98 | 100 | 98 | 90 | 100 | 90 |
| Green foxtail | 100 | 100 | — | 100 | — | — | — | — | — | — |
| Guineagrass | 100 | 50 | 85 | 100 | 98 | 95 | 80 | 85 | 80 | 100 |
| Itchgrass | 20 | 75 | 85 | 30 | 60 | 65 | 0 | 0 | 70 | 40 |
| Johnsongrass | 40 | 98 | 75 | 90 | 80 | 90 | 0 | 0 | 50 | 35 |
| Kochia | 100 | — | — | 75 | — | — | — | — | — | — |
| Large crabgrass | 100 | 100 | 100 | 100 | 98 | 90 | 60 | 98 | 100 | 95 |
| Leafy spurge | 95 | 98 | — | 65 | — | — | — | — | — | — |
| P. morninglory | 80 | 100 | 60 | 40 | 0 | 30 | 30 | 65 | 100 | 75 |
| Purple nutsedge | 0 | 0 | 0 | 0 | 0 | 30 | 0 | 0 | 30 | 5 |
| Quackgrass | 80 | 90 | — | 65 | — | — | — | — | — | — |
| Russian Thistle | — | — | — | 90 | — | — | — | — | — | — |
| Sandbur | 65 | 65 | 0 | 20 | 80 | 40 | 60 | 10 | 10 | 60 |
| Sourgrass | 100 | 100 | 100 | 100 | 98 | 100 | 100 | 100 | 100 | 100 |
| Spanishneedles | 80 | 100 | 20 | 30 | 70 | 20 | 60 | 85 | 20 | 0 |
| Sugarcane | — | 0 | — | 0 | — | — | — | — | — | — |
| Surinam grass | 35 | 90 | 10 | 20 | — | 50 | — | 0 | 70 | 75 |
| Tall Mallow | 100 | 100 | 100 | 100 | 85 | 98 | 80 | 100 | 98 | 90 |

| | COMPOUND Rate 32 g/ha | | | | | | | | | |
|---|---|---|---|---|---|---|---|---|---|---|
| PREEMERGENCE | 1 | 2 | 9 | 15 | 23 | 42 | 44 | 46 | 52 | 67 |
| A. bluegrass | 90 | 80 | — | 100 | — | — | — | — | — | — |
| Alexandergrass | 10 | 50 | 30 | 75 | 0 | 20 | 0 | 0 | 20 | 25 |
| Arrowleaf sida | 98 | 98 | — | 65 | — | — | — | — | — | — |
| B. signalgrass | 20 | 65 | — | 35 | — | — | — | — | — | — |
| Barnyardgrass | 5 | 20 | — | 0 | — | — | — | — | — | — |
| Bermudagrass | 100 | 98 | 70 | 98 | 90 | 90 | 30 | 70 | 70 | 70 |
| Com. purslane | 98 | 100 | 100 | 100 | 100 | 100 | 80 | 100 | 100 | 80 |
| Com. ragweed | 90 | 100 | 10 | 100 | 50 | 50 | 40 | 0 | 35 | 90 |
| Com. chickweed | 30 | 100 | — | 65 | — | — | — | — | — | — |
| Com. groundsel | 98 | 100 | 98 | 100 | 100 | 90 | 98 | 100 | 35 | 0 |
| Dallisgrass | 98 | 90 | 85 | 95 | 80 | 70 | 65 | 65 | 35 | 40 |
| Goosegrass | 100 | 95 | 90 | 98 | 98 | 98 | 98 | 85 | 20 | 80 |
| Green foxtail | 100 | 90 | — | 100 | — | — | — | — | — | — |
| Guineagrass | 90 | 50 | 20 | 90 | 80 | 95 | 20 | 60 | 60 | 80 |
| Itchgrass | 20 | 70 | 100 | 10 | 30 | 35 | 0 | 0 | 35 | 40 |
| Johnsongrass | 5 | 65 | 55 | 60 | 70 | 10 | 30 | 0 | — | 35 |
| Kochia | 95 | — | — | 60 | — | — | — | — | — | — |
| Large crabgrass | 100 | 98 | 70 | 98 | 98 | 50 | 0 | 90 | 98 | 90 |
| Leafy spurge | 75 | 60 | — | 35 | — | — | — | — | — | — |
| P. morninglory | 70 | 100 | 45 | 5 | 0 | — | 20 | 65 | 50 | 60 |
| Purple nutsedge | 0 | 0 | 0 | 0 | 0 | 20 | 0 | 0 | 5 | 0 |
| Quackgrass | 65 | 20 | — | 65 | — | — | — | — | — | — |
| Russian Thistle | — | — | — | 70 | — | — | — | — | — | — |

TABLE E-continued

| | | | | | | | | | | |
|---|---|---|---|---|---|---|---|---|---|---|
| Sandbur | 20 | 20 | 0 | 10 | 85 | 0 | 0 | 0 | 0 | 60 |
| Sourgrass | 100 | 100 | 85 | 100 | 98 | 100 | 80 | 98 | 95 | 98 |
| Spanishneedles | 40 | 80 | 0 | 50 | 60 | 20 | 20 | 65 | 20 | 0 |
| Sugarcane | — | — | — | 0 | — | — | — | — | — | — |
| Surinam grass | 65 | 50 | 0 | 20 | — | 40 | — | 0 | 30 | 35 |
| Tall Mallow | 100 | 98 | 100 | 98 | 80 | 98 | 80 | 100 | 60 | 80 |

| | COMPOUND | | | | | | | | | | | | | |
|---|---|---|---|---|---|---|---|---|---|---|---|---|---|---|
| | Rate 500 g/ha | Rate 250 g/ha | | | | | | | Rate 125 g/ha | | | | | Rate 64 g/ha | Rate 32 g/ha |
| POSTEMERGENCE | 2 | 1 | 2 | 9 | 15 | 23 | 44 | 52 | 2 | 9 | 15 | 44 | 52 | 2 | 2 |
| Alexandergrass | 95 | 90 | 80 | 10 | 20 | 80 | 10 | 75 | 30 | 10 | 10 | 10 | 10 | 30 | 20 |
| Bermudagrass | 75 | 30 | 50 | 10 | 20 | 10 | 0 | 35 | 35 | 10 | 20 | 0 | 35 | 20 | 10 |
| Com. purslane | 70 | 40 | 70 | 80 | 80 | 50 | 70 | 75 | 65 | 80 | 75 | 70 | 50 | 65 | 65 |
| Com. ragweed | 75 | 70 | 75 | 10 | 10 | 40 | 20 | 80 | 75 | 10 | 5 | 10 | 50 | — | 50 |
| Com. groundsel | 75 | 75 | 40 | 30 | 20 | 40 | 10 | 100 | 20 | 25 | 0 | 10 | 100 | 20 | 0 |
| Dallisgrass | 95 | 90 | 90 | 20 | 50 | 40 | 10 | 75 | 70 | 10 | 5 | 10 | 5 | 40 | 10 |
| Goosegrass | 95 | 70 | 90 | 10 | 30 | 75 | 20 | 75 | — | 5 | 20 | 10 | 5 | 75 | 60 |
| Guineagrass | 90 | 70 | 50 | 35 | 40 | 75 | 85 | 85 | 50 | 35 | 20 | 85 | 80 | — | 5 |
| Itchgrass | 95 | 85 | 90 | 30 | 85 | 80 | 10 | 40 | 75 | 30 | 80 | 5 | 35 | 40 | 40 |
| Johnsongrass | 95 | 90 | 80 | 85 | 100 | 65 | 10 | 20 | 60 | 85 | 98 | 5 | 35 | 60 | 10 |
| Large crabgrass | 90 | 85 | 80 | 10 | 40 | 40 | 10 | 80 | 75 | 5 | 10 | 10 | 5 | 35 | 35 |
| P. morninglory | 90 | 80 | 90 | 50 | 5 | 40 | 40 | 80 | 80 | 40 | 5 | 30 | 80 | 80 | 80 |
| Purple nutsedge | 0 | 0 | 0 | 0 | 0 | 0 | 0 | 50 | 0 | 0 | 0 | 0 | 40 | 0 | 0 |
| Sandbur | 80 | 10 | 50 | 0 | 0 | 20 | 0 | 60 | 10 | 0 | 0 | 0 | 5 | 10 | 0 |
| Sourgrass | 80 | 30 | 40 | 30 | 25 | 30 | 20 | 50 | 20 | 10 | 20 | 10 | 10 | 20 | 10 |
| Spanishneedles | 70 | 10 | — | 15 | 10 | 10 | 10 | 60 | 40 | 10 | 5 | 10 | 65 | 60 | 60 |
| Sugarcane | 25 | — | 25 | — | — | — | — | — | 20 | — | — | — | — | 20 | 20 |
| Surinam grass | 80 | 30 | 70 | 10 | 40 | — | — | 75 | 50 | 10 | 35 | — | 75 | 50 | 35 |
| Tall Mallow | 100 | 90 | 100 | 90 | 98 | 90 | 90 | 75 | 100 | 90 | 85 | 85 | 90 | 95 | 98 |

What is claimed is:

1. A compound selected from Formula I, geometric or stereoisomers thereof, N-oxides thereof and agriculturally suitable salts thereof,

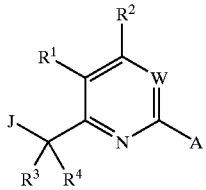

wherein J is

-continued

J-1

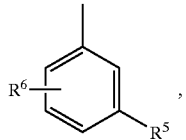

J-2

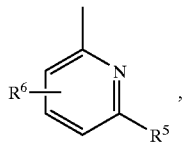

J-3

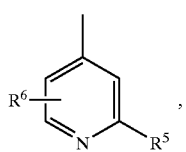

J-4

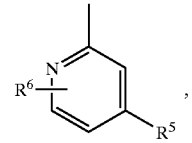

J-5

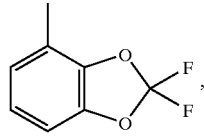

J-6

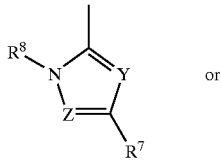

or

J-7

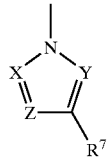

-continued

A is 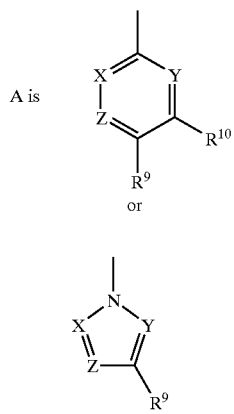

W is N;
X, Y and Z are independently N or $CR^{12}$;
$R^1$ and $R^2$ are independently H, $C_1$–$C_4$ alkyl or $C_1$–$C_4$ alkoxy;
$R^3$ is H, F, Cl, Br, cyano, $C_1$–$C_4$ alkyl, $C_1$–$C_4$ haloalkyl or $CO_2R^{14}$;
$R^4$ is H, F, $C_1$–$C_4$ alkyl, OH or $OR^{14}$;
$R^3$ and $R^4$ can be taken together with the carbon to which they are attached to form C(=O) or C(=$NOR^{14}$);
$R^5$ and $R^7$ are independently $C_1$–$C_4$ haloalkyl or $C_1$–$C_4$ haloalkoxy;
$R^6$ is H or F;
$R^8$ is $C_1$–$C_4$ alkyl;
$R^9$ is halogen, $C_1$–$C_4$ haloalkoxy, $C_1$–$C_4$ haloalkyl or $S(O)_nR^{13}$;
$R^{10}$ is H, halogen, cyano or $C_1$–$C_4$ haloalkyl;
$R^{11}$ is H, halogen, cyano or $C_1$–$C_4$ haloalkyl;
$R^{12}$ is H, halogen, cyano or $C_1$–$C_4$ haloalkyl;
each $R^{13}$ is independently $C_1$–$C_4$ alkyl or $C_1$–$C_4$ haloalkyl;
each $R^{14}$ is independently $C_1$–$C_4$ alkyl; and
n is 0.

2. A compound of claim 1 wherein
$R^1$ is $C_1$–$C_4$ alkyl or $C_1$–$C_4$ alkoxy;
$R^2$ is H;
$R^3$ and $R^4$ are independently H, F or methyl;
$R^5$ and $R^7$ are independently $C_1$–$C_2$ haloalkyl or $C_1$–$C_2$ haloalkoxy; and
$R^9$ is $C_1$–$C_2$ haloalkoxy, $C_1$–$C_2$ haloalkyl or $S(O)_nR^{13}$.

3. A compound of claim 2 wherein
J is J-1, J-5 or J-7.

4. A compound of claim 1 wherein
$R^3$ and $R^4$ can be taken together with the carbon to which they are attached to form C(=O).

5. A compound of claim 4 wherein
$R^1$ is $C_1$–$C_4$ alkyl or $C_1$–$C_4$ alkoxy;
$R^2$ is H;
$R^5$ and $R^7$ are independently $C_1$–$C_2$ haloalkyl or $C_1$–$C_2$ haloalkoxy; and
$R^9$ is $C_1$–$C_2$ haloalkoxy, $C_1$–$C_2$ haloalkyl or $S(O)_nR^{13}$.

6. A compound of claim 5 wherein
J is J-1 or J-5.

7. The compound of claim 1 selected from the group consisting of (a) 5-ethyl-4-[[3-(trifluoromethoxy)phenyl]methyl]-2-[3-trifluoromethyl)-1H-pyrazol-1-yl]pyrmidine;
(b) 5-ethyl-4-[[3-(trifluoromethyl)phenyl]methyl]-2-[3 (trifluoromethyl)-1H-pyrazol-1-yl]pyrimidine;
(c) 5-methyl-2-[4-(trifluoromethyl)phenyl]-4-[[3-(trifluoromethyl)phenyl]methyl]pyrimidine;
(d) 5-methyl-4-[[3-(trifluoromethoxy)phenyl]methyl]-2-[4-trifluoromethyl)phenyl]pyrimidine;
(e) 5-methyl-4-[[3-(trifluoromethoxy)phenyl]methyl]-2-[3-(trifluoromethyl)-1H-pyrazol-1-yl]pyrimidine;
(f) [5-methyl-2-[4-(trifluoromethyl)phenyl]-4-pyrimidinyl] [3-(trifluoromethyl)phenyl]methanone;
(g) [5-methyl-2-[3-(trifluoromethyl)-1H-pyrazol-1-yl]-4-pyrimidinyl][3-(trifluoromethyl)phenyl]methanone; and
(h) 5-methyl-4-[[3-(trifluoromethyl)phenyl]methyl]-2-[3-(trifluoromethyl-1H-pyrazol-1-yl]pyrimidine.

8. A herbicidal composition comprising a herbicidally effective amount of a compound of claim 1 and at least one of a surfactant, a solid diluent or a liquid diluent.

9. A method for controlling the growth of undesired vegetation comprising contacting the vegetation or its environment with a herbicidally effective amount of a compound of claim 1.

* * * * *